(12) United States Patent
Din Belle et al.

(10) Patent No.: US 8,697,723 B2
(45) Date of Patent: Apr. 15, 2014

(54) 2,3-DIHYDROBENZO(1,4) DIOXIN-2-YLMETHYL DERIVATIVES AS ALPHA2C ANTAGONISTS FOR USE IN THE TREATMENT OF PERIPHERIC AND CENTRAL NERVOUS SYSTEM DISEASES

(71) Applicant: Orion Corporation, Espoo (FI)

(72) Inventors: David Din Belle, Espoo (FI); Patrik Holm, Lielahti (FI); Arto Karljalainen, Espoo (FI); Arto Tolvanen, Espoo (FI); Gerd Wohlfahrt, Helsinki (FI); Petteri Rummakko, Siuntio (FI)

(73) Assignee: Orion Corporation, Espoo (FI)

( * ) Notice: Subject to any disclaimer, the term of this patent is extended or adjusted under 35 U.S.C. 154(b) by 0 days.

(21) Appl. No.: 13/917,745

(22) Filed: Jun. 14, 2013

(65) Prior Publication Data

US 2013/0281486 A1    Oct. 24, 2013

Related U.S. Application Data

(62) Division of application No. 12/668,918, filed as application No. PCT/FI2008/000090 on Jul. 18, 2008, now Pat. No. 8,492,549.

(60) Provisional application No. 60/950,983, filed on Jul. 20, 2007.

(51) Int. Cl.
    *C07D 405/06*      (2006.01)
    *C07D 319/16*      (2006.01)

(52) U.S. Cl.
    USPC ............ 514/307; 514/338; 514/321; 514/422

(58) Field of Classification Search
None
See application file for complete search history.

(56) References Cited

U.S. PATENT DOCUMENTS

| | | | |
|---|---|---|---|
| 2,056,046 A | 9/1936 | Fourneau | |
| 3,644,414 A | 2/1972 | Helsley | |
| 3,944,549 A | 3/1976 | Lafon | |
| 4,140,781 A | 2/1979 | Huebner | |
| 4,329,348 A | 5/1982 | Huebner | |
| 4,957,928 A | 9/1990 | Fröstl et al. | |
| 5,767,116 A | 6/1998 | Kerrigan et al. | |
| 5,902,807 A | 5/1999 | Haapalinna et al. | |
| 5,935,973 A | 8/1999 | Birch et al. | |
| 8,492,549 B2 | 7/2013 | Din Belle et al. | |
| 2003/0050309 A1 | 3/2003 | Aquila et al. | |

FOREIGN PATENT DOCUMENTS

| | | |
|---|---|---|
| DE | 31 39 301 A1 | 6/1982 |
| DE | 250 930 A1 | 10/1987 |
| EP | 0 183 492 A1 | 6/1986 |
| FR | 2 525 600 | 10/1983 |
| JP | 51-63193 | 6/1976 |
| WO | WO 90/02122 | 3/1990 |
| WO | WO 92/14453 | 9/1992 |
| WO | WO 97/28157 | 8/1997 |
| WO | WO 98/50359 | 11/1998 |
| WO | WO 99/28300 | 6/1999 |
| WO | WO 01/64645 A2 | 9/2001 |
| WO | WO 02/22572 A2 | 3/2002 |
| WO | WO 03/082866 A1 | 10/2003 |
| WO | WO 2004/067513 A1 | 8/2004 |

OTHER PUBLICATIONS

Mayer, P., et al., "New Substituted 1-(2,3-Dihydrobenzo[1,4]dioxin-2-ylmethyl)piperidin-4-yl Derivatives with α2-Adrenoceptor Antagonist Activity," *J. Med. Chem.* (2000) 43:3653-3664.

Bolchi, C., et al., "Highly efficient resolutions of 1,4-benzodioxane-2-carboxylic acid with para substituted 1-phenylethylamines," *Tetrahedron: Asymmetry* (2005) 16:1639-1643.

CAPlus English Abstract for DD 250 930, accession No. 1988:406528.

CAPlus English Abstract for DE 31 39 301, accession No. 1982:544387.

CAPlus English Abstract for FR 2 525 600, accession No. 1984:156506.

CAPlus English Abstract for JP 51-63193, accession No. 1977:5454.

Colpaert, F. C. and Raeymaekers, L., "In Vivo Pharmacological Activity of R 47 243 in Rat: A Comparison With Putative $\alpha_2$-Adrenoceptor Antagonists," *Drug Development Research* (1986) 8:361-371.

Hacksell, U., et al., "3-Phenylpiperidines. Central Dopamine-Autoreceptor Stimulating Activity," *J. Med. Chem.* (1981) 24:1475-1482.

Henning, R., et at, "Synthesis and Neuroleptic Activity of a Series of 1-[1-(Benzo-1,4-dioxan-2-ylmethyl)-4-piperidinyl]benzimidazolone Derivatives," *J. Med. Chem.* (1987) 3:814-819.

Koo, J., "Derivatives of 1,4-Benzodioxan. II. 3-Methyl-1,4-benzodioxan-2-carboxamides and Corresponding Amines," *J. Org. Chem.* (1961) 26:339-343.

(Continued)

*Primary Examiner* — Janet L Andres
*Assistant Examiner* — Timothy R. Rozof
(74) *Attorney, Agent, or Firm* — Finnegan, Henderson, Farabow, Garrett & Dunner, LLP

(57) ABSTRACT

Compounds of formula I wherein X, Z, $R_1$-$R_4$, and m are as defined in the claims, exhibit alpha2C antagonistic activity, and are thus useful as alpha2C antagonists. Methods for the treatment of diseases and conditions of the peripheric system and the central nervous system are also disclosed.

2 Claims, No Drawings

(56) References Cited

OTHER PUBLICATIONS

Nelson, T. D., et al., "Synthesis of a Potent hNK-1 Receptor Antagonist via an $S_N2$ Reaction of an Enantiomerically Pure α-Alkoxy Sulfonate," *Organic Letters* (2005) 7(1):55-58.

Sonesson, C. and Lindberg, J.,"An Efficient Synthesis of the Novel Dopamine Autoreceptor Antagonist S-(−)-OSU6162, via Palladium Catalyzed Cross-Coupling Reaction," *Tetrahedron Letters* (1994) 35(48):9063-9066.

Wu, Y. and Feldkamp, R.F., "Pyrrolidines. I. 1-Substituted 3-Pyrrolidinylmethyl Alcohols and Chlorides," *J. Org. Chem.* (1961) 26:1519-1524.

International Search Report for International Application No. PCT/FI2008/000090 dated Dec. 15, 2008.

Written Opinion of the International Searching Authority for International Application No. PCT/FI2008/000090 dated Dec. 15, 2008.

2,3-DIHYDROBENZO(1,4) DIOXIN-2-YLMETHYL DERIVATIVES AS ALPHA2C ANTAGONISTS FOR USE IN THE TREATMENT OF PERIPHERIC AND CENTRAL NERVOUS SYSTEM DISEASES

This application is divisional application of U.S. patent application Ser. No. 12/668,918, which was a national stage filing under 35 U.S.C. §371 of International Application No. PCT/FI2008/000090 filed on Jul. 18, 2008, which claims the benefit of priority of U.S. Provisional Application No. 60/950,983 filed on Jul. 20, 2007, all of which are incorporated herein by reference.

FIELD OF THE INVENTION

The present invention relates to pharmacologically active 3-substituted 1-(2,3-dihydrobenzo[1,4]dioxin-2-ylmethyl) azacycles, or pharmaceutically acceptable salts and esters thereof, as well as to pharmaceutical compositions comprising them and to their use as alpha2C antagonists.

BACKGROUND OF THE INVENTION

It is generally known and accepted in the art that compounds exhibiting alpha adrenergic activity may be used for the treatment of a wide variety of diseases and conditions of the peripheric system and the central nervous system (CNS).

The alpha adrenergic receptors can be divided on a pharmacological basis into alpha1 and alpha2 adrenoceptors, which can both be further divided into subtypes. Three genetically encoded subtypes, namely alpha2A, alpha2B, and alpha2C adrenoceptors, have been discovered in human. A fourth pharmacologically defined subtype, namely alpha2D adrenoceptor, is known in some other mammals and in rodents. It corresponds to the genetically defined alpha2A adrenoceptor.

The alpha2 adrenoceptor subtypes have distinct tissue distributions and functional roles. For instance, while alpha2A adrenoceptors are widely expressed in various tissues, alpha2C adrenoceptors are concentrated in the CNS and appear to play a role in the modulation of specific CNS mediated behavioral and physiological responses.

Some compounds that are non-specific for any of the above-mentioned alpha2 subtypes and some compounds that are specific for certain alpha2 subtypes are known in the art. For example, atipamezole disclosed in EP 183 492 A1 (compound XV at page 13) is a non-specific alpha2 antagonist. Compounds that are selective antagonists for the alpha2C subtype and are useful for the treatment of mental illness, e.g. mental disturbance induced by stress, are described in U.S. Pat. No. 5,902,807. Such compounds are, for example, MK-912 and BAM-1303. Imidazole derivatives having agonist-like activity for alpha2B or 2B/2C adrenoceptors are disclosed in WO 99/28300. Quinoline derivatives useful as alpha2 antagonists are disclosed in WO 01/64645 and WO 2004/067513. Arylquinolizine derivatives useful as alpha2 antagonists are disclosed in WO 03/082866.

In order to be able to reduce the risk of adverse events during treatment, an enhanced selectivity of the alpha2 antagonists would be desirable. For example, the use of non-selective alpha2 antagonists is attributed with side effects, such as increases in blood pressure, heart rate, salivary secretion, gastrointestinal secretion, and anxiety. Also an enhanced potency of the alpha2C antagonists would be desirable, in order to be able to reduce the dose needed.

As to known 3-substituted 1-(2,3-dihydrobenzo[1,4]dioxin-2-ylmethyl)azacycles, 1-(6-tert-butyl-2,3-dihydrobenzo[1,4]dioxin-2-ylmethyl)-3,5-dimethyl-piperidine, 1-(7-tert-butyl-2,3-dihydrobenzo[1,4]dioxin-2-ylmethyl)-3,5-dimethyl-piperidine, 1-[1-(7-tert-butyl-2,3-dihydrobenzo[1,4]dioxin-2-yl)-ethyl]-3,5-dimethyl-piperidine, 1-(2,3-dihydrobenzo[1,4]dioxin-2-ylmethyl)-3,5-dimethyl-piperidine, 1-(7-tert-butyl-2,3-dihydrobenzo[1,4]dioxin-2-ylmethyl)-3,3-dimethyl-piperidine, 1-(6-tert-butyl-2,3-dihydrobenzo[1,4]dioxin-2-ylmethyl)-3,3-dimethyl-piperidine, 1-(7-tert-butyl-2,3-dihydrobenzo[1,4]dioxin-2-ylmethyl)-3-methyl-piperidine, 1-(6-tert-butyl-2,3-dihydrobenzo[1,4]dioxin-2-ylmethyl)-3-methyl-piperidine, and 1-[1-(6-tert-butyl-2,3-dihydrobenzo[1,4]dioxin-2-yl)-ethyl]-3,5-dimethyl-piperidine have been disclosed in WO 90/02122. 1-(2,3-Dihydrobenzo[1,4]dioxin-2-ylmethyl)-piperidine-3-carboxylic acid methyl ester, 1-(2,3-dihydrobenzo[1,4]dioxin-2-ylmethyl)-4-oxo-piperidine-3-carboxylic acid methyl ester, 1-(2,3-dihydrobenzo[1,4]dioxin-2-ylmethyl)-1,2,5,6-tetrahydro-pyridine-3-carboxylic acid methyl ester, and 1-(2,3-dihydrobenzo[1,4]dioxin-2-ylmethyl)-4-hydroxy-1,2,5,6-tetrahydro-pyridine-3-carboxylic acid methyl ester have been disclosed in U.S. Pat. No. 4,957,928. 2-(2,3-Dihydrobenzo[1,4]dioxin-2-ylmethyl)-6,7-dimethoxy-1-methyl-1,2,3,4-tetrahydro-isoquinoline and 2-(2,3-dihydrobenzo[1,4]dioxin-2-ylmethyl)-6,7-dimethoxy-1,2,3,4-tetrahydro-isoquinoline have been disclosed in DD 250 930 A1. 2-(2,3-Dihydrobenzo[1,4]dioxin-2-ylmethyl)-1,2,3,4-tetrahydro-isoquinoline has been disclosed in *J. Org. Chem.*, 26 (1961) 339. 1-(2,3-Dihydrobenzo[1,4]dioxin-2-ylmethyl-3-(3-trifluoromethyl-phenyl)-pyrrolidine has been disclosed in U.S. Pat. No. 3,644,414.

SUMMARY OF THE INVENTION

An object of the present invention is to provide further alpha2C antagonists that can be used for the treatment of diseases or conditions of the peripheric or central nervous system wherein alpha2C antagonists are indicated to be useful. Accordingly, an object of the present invention is to provide further compounds to be used as alpha2C antagonists in the treatment of mammals. Furthermore, pharmaceutical compositions comprising the present compounds are provided.

The alpha2 antagonists of the present invention have an improved selectivity for the alpha2C adrenoceptor subtype and/or an enhanced potency.

DETAILED DESCRIPTION OF THE INVENTION

The present invention relates to novel alpha2C antagonists having the general formula I,

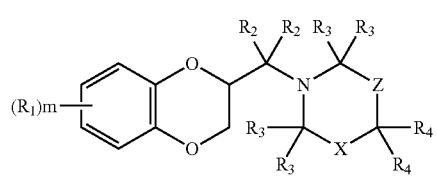

wherein
X is $C(R_5)(R_6)$ or $C(R_7)(R_8)$;
Z is $—[C(R_4)_2]_n—$ or a single bond;

$R_1$ is, independently at each occurrence, hydroxy, $(C_1-C_6)$alkyl, $(C_1-C_6)$alkoxy, halogen, halo$(C_1-C_6)$alkyl, phenyl$(C_1-C_6)$alkoxy, $(C_1-C_6)$alkoxy-(C=O)—, CN, NO$_2$, NH$_2$, mono- or di$(C_1-C_6)$alkylamino or carboxy;

$R_2$ is, independently at each occurrence, H or $(C_1-C_6)$alkyl;
$R_3$ is, independently at each occurrence, H or $(C_1-C_6)$alkyl;
$R_4$ is, independently at each occurrence, H, hydroxy, $(C_1-C_6)$alkyl, $(C_2-C_6)$alkenyl, hydroxy$(C_1-C_6)$alkyl, hydroxy$(C_2-C_6)$alkenyl, $(C_1-C_6)$alkoxy$(C_1-C_6)$alkyl, $(C_2-C_6)$alkenyloxy$(C_1-C_6)$alkyl, $(C_1-C_6)$alkyl-(C=O)—, $(C_1-C_6)$alkoxy-(C=O)—, hydroxy$(C_1-C_6)$alkoxy$(C_1-C_6)$alkyl or $(C_1-C_6)$alkoxy$(C_1-C_6)$alkoxy$(C_1-C_6)$alkyl;

or $R_4$ and $R_4$ both attached to the same carbon ring atom form, together with the carbon ring atom to which they are attached, a —(C=O)— group;

$R_5$ is H or hydroxy;

or $R_4$ and $R_5$ attached to adjacent carbon ring atoms form a bond between the carbon ring atoms to which they are attached;

$R_6$ is phenyl unsubstituted or substituted with 1 or 2 substituent(s) $R_9$;

$R_7$ is H, $(C_1-C_6)$alkyl, hydroxy$(C_1-C_6)$alkyl, $(C_1-C_6)$alkoxy$(C_1-C_6)$alkyl or $(C_1-C_6)$alkoxy-(C=O)—;

or $R_4$ and $R_7$ attached to adjacent carbon ring atoms form a bond between the carbon ring atoms to which they are attached;

$R_8$ is hydroxy, $(C_1-C_6)$alkyl, $(C_2-C_6)$alkenyl, $(C_1-C_6)$alkoxy, halogen, hydroxy$(C_1-C_6)$alkyl, halo$(C_1-C_6)$alkyl, hydroxy$(C_2-C_6)$alkenyl, hydroxy$(C_1-C_6)$alkoxy, halo$(C_1-C_6)$alkoxy, phenyl$(C_1-C_6)$alkoxy, $(C_1-C_6)$alkoxy$(C_1-C_6)$alkyl, $(C_2-C_6)$alkenyloxy$(C_1-C_6)$alkyl, $(C_1-C_6)$alkyl-(C=O)—, $(C_1-C_6)$alkoxy-(C=O)—, $(C_1-C_6)$alkoxy-(C=O)—$(C_1-C_6)$alkyl, $(C_1-C_6)$alkyl-S—, $(C_1-C_6)$alkyl-(C=O)—O—, $(C_1-C_6)$alkyl-(C=O)—O—$(C_1-C_6)$alkyl, hydroxy-(C=O)—$(C_1-C_6)$alkoxy, hydroxy-(C=O)—$(C_1-C_6)$alkoxy$(C_1-C_6)$alkyl, $(C_1-C_6)$alkoxy-(C=O)—$(C_1-C_6)$alkoxy$(C_1-C_6)$alkyl, $(C_1-C_6)$alkyl-S—$(C_1-C_6)$alkyl, hydroxy$(C_1-C_6)$alkyl-S—$(C_1-C_6)$alkyl, $(C_1-C_6)$alkoxy$(C_1-C_6)$alkyl-S—$(C_1-C_6)$alkyl, $(C_1-C_6)$alkyl-(C=O)—S—$(C_1-C_6)$alkyl, $(C_1-C_6)$alkoxy-(C=O)—$(C_1-C_6)$alkyl-S—$(C_1-C_6)$alkyl, $(C_1-C_6)$alkyl-S—$(C_1-C_6)$alkoxy$(C_1-C_6)$alkyl, hydroxy$(C_1-C_6)$alkyl-S—$(C_1-C_6)$alkoxy$(C_1-C_6)$alkyl, $(C_1-C_6)$alkoxy$(C_1-C_6)$alkyl-S—$(C_1-C_6)$alkoxy$(C_1-C_6)$alkyl, $(C_1-C_6)$alkyl-(O=S=O)—$(C_1-C_6)$alkyl, hydroxy$(C_1-C_6)$alkyl-(O=S=O)—$(C_1-C_6)$alkyl, $(C_1-C_6)$alkoxy$(C_1-C_6)$alkyl-(O=S=O)—$(C_1-C_6)$alkyl, $(C_1-C_6)$alkyl-(O=S=O)—$(C_1-C_6)$alkoxy$(C_1-C_6)$alkyl, hydroxy$(C_1-C_6)$alkyl-(O=S=O)—$(C_1-C_6)$alkoxy$(C_1-C_6)$alkyl, $(C_1-C_6)$alkoxy$(C_1-C_6)$alkyl-(O=S=O)—$(C_1-C_6)$alkoxy$(C_1-C_6)$alkyl, $(C_1-C_6)$alkyl-O—(O=S=O)—$(C_1-C_6)$alkyl, hydroxy$(C_1-C_6)$alkyl-O—(O=S=O)—$(C_1-C_6)$alkyl, $(C_1-C_6)$alkyl-(O=S=O)—O—$(C_1-C_6)$alkyl, hydroxy$(C_1-C_6)$alkyl-(O=S=O)—O—$(C_1-C_6)$alkyl, $(C_1-C_6)$alkyl-(O=S=O)—N(R$_{10}$)—$(C_1-C_6)$alkyl, hydroxy$(C_1-C_6)$alkoxy$(C_1-C_6)$alkyl, $(C_1-C_6)$alkoxy$(C_1-C_6)$alkoxy$(C_1-C_6)$alkyl, halo$(C_1-C_6)$alkoxy$(C_1-C_6)$alkyl, CN, NO$_2$, $(R_{10})_2$N—, $(R_{10})_2$N—$(C_1-C_6)$alkyl, $(R_{10})_2$N—(C=O)—, $(R_{10})_2$N—(C=O)—$(C_1-C_6)$alkoxy$(C_1-C_6)$alkyl, $(R_{10})_2$N—(C=O)—$(C_1-C_6)$alkyl-S—$(C_1-C_6)$alkyl, $(R_{10})_2$N—(C=O)—$(C_1-C_6)$alkyl-(O=S=O)—$(C_1-C_6)$alkyl, carboxy, $R_{11}$—(O=S=O)— or $R_{11}$—(O=S=O)—O—;

or $R_9$ and $R_9$ attached to adjacent carbon ring atoms form, together with the carbon ring atoms to which they are attached, a condensed phenyl ring, a condensed 5 or 6 membered unsaturated carbocyclic ring or a condensed 5 or 6 membered unsaturated heterocyclic ring containing 1 or 2 heteroatom(s) selected from O and S, wherein said phenyl, carbocyclic or heterocyclic ring is unsubstituted or substituted with 1 or 2 substituent(s) each independently being hydroxy, $(C_1-C_6)$alkyl, $(C_1-C_6)$alkoxy, hydroxy$(C_1-C_6)$alkyl, halo$(C_1-C_6)$alkyl, $(C_1-C_6)$alkoxy$(C_1-C_6)$alkyl, $(C_1-C_6)$alkyl-(C=O)— or $(C_1-C_6)$alkoxy-(C=O)—;

$R_{10}$ is, independently at each occurrence, H, $(C_1-C_6)$alkyl, hydroxy$(C_1-C_6)$alkyl, $(C_1-C_6)$alkyl-(C=O)— or $R_{11}$—(O=S=O)—;

$R_{11}$ is, independently at each occurrence, hydroxy, $(C_1-C_6)$alkyl, $(C_1-C_6)$alkoxy, halo$(C_1-C_6)$alkyl or mono- or di$(C_1-C_6)$alkylamino;

m is 0, 1 or 2; and n is 1 or 2;

or a pharmaceutically acceptable salt or ester thereof;

with the provisos that the compound is not 1-(6-tert-butyl-2,3-dihydrobenzo[1,4]dioxin-2-ylmethyl)-3,5-dimethyl-piperidine, 1-(7-tert-butyl-2,3-dihydrobenzo[1,4]dioxin-2-ylmethyl)-3,5-dimethyl-piperidine, 1-[1-(7-tert-butyl-2,3-dihydrobenzo[1,4]dioxin-2-yl)-ethyl]-3,5-dimethyl-piperidine, 1-(2,3-dihydrobenzo[1,4]dioxin-2-ylmethyl)-3,5-dimethyl-piperidine, 1-(7-tert-butyl-2,3-dihydrobenzo[1,4]dioxin-2-ylmethyl)-3,3-dimethyl-piperidine, 1-(6-tert-butyl-2,3-dihydrobenzo[1,4]dioxin-2-ylmethyl)-3,3-dimethyl-piperidine, 1-(7-tert-butyl-2,3-dihydrobenzo[1,4]dioxin-2-ylmethyl)-3-methyl-piperidine, 1-(6-tert-butyl-2,3-dihydrobenzo[1,4]dioxin-2-ylmethyl)-3-methyl-piperidine, 1-[1-(6-tert-butyl-2,3-dihydrobenzo[1,4]dioxin-2-yl)-ethyl]-3,5-dimethyl-piperidine, 1-(2,3-dihydrobenzo[1,4]dioxin-2-ylmethyl)-piperidine-3-carboxylic acid methyl ester, 1-(2,3-dihydrobenzo[1,4]dioxin-2-ylmethyl)-4-oxo-piperidine-3-carboxylic acid methyl ester, 1-(2,3-dihydrobenzo[1,4]dioxin-2-ylmethyl)-1,2,5,6-tetrahydro-pyridine-3-carboxylic acid methyl ester, 1-(2,3-dihydrobenzo[1,4]dioxin-2-ylmethyl)-4-hydroxy-1,2,5,6-tetrahydro-pyridine-3-carboxylic acid methyl ester, 2-(2,3-dihydrobenzo[1,4]dioxin-2-ylmethyl)-6,7-dimethoxy-1-methyl-1,2,3,4-tetrahydro-isoquinoline, 2-(2,3-dihydrobenzo[1,4]dioxin-2-ylmethyl)-6,7-dimethoxy-1,2,3,4-tetrahydro-isoquinoline, 2-(2,3-dihydrobenzo[1,4]dioxin-2-ylmethyl)-1,2,3,4-tetrahydro-isoquinoline or 1-(2,3-dihydro-benzo[1,4]dioxin-2-ylmethyl-3-(3-trifluoromethyl-phenyl)-pyrrolidine.

In a possible subgroup of the compounds of formula I, Z is —[C(R$_4$)$_2$]$_n$—.

In a further possible subgroup of the compounds of formula I, n is 1.

In another possible subgroup of the compounds of formula I, n is 2.

In a further possible subgroup of the compounds of formula I, Z is a single bond.

In a further possible subgroup of the compounds of formula I, $R_2$ is H.

In a further possible subgroup of the compounds of formula I, $R_3$ is H.

In a further possible subgroup of the compounds of formula I, $R_4$ is, independently at each occurrence, H, $(C_1-C_6)$alkyl, $(C_2-C_6)$alkenyl, hydroxy$(C_2-C_6)$alkenyl, $(C_1-C_6)$alkoxy$(C_1-C_6)$alkyl, $(C_2-C_6)$alkenyloxy$(C_1-C_6)$alkyl, $(C_1-C_6)$alkyl-(C=O)—, $(C_1-C_6)$alkoxy-(C=O)—, hydroxy$(C_1-C_6)$alkoxy$(C_1-C_6)$alkyl or $(C_1-C_6)$alkoxy$(C_1-C_6)$alkoxy$(C_1-C_6)$alkyl; for example, H.

In another possible subgroup of the compounds of formula I, $R_4$ is, independently at each occurrence, H, hydroxy or $(C_1-C_6)$alkyl; for example, H.

In a further possible subgroup of the compounds of formula I, m is 0.

In another possible subgroup of the compounds of formula I, m is 1.

In a further possible subgroup of the compounds of formula I, $R_1$ is, independently at each occurrence, hydroxy, phenyl$(C_1-C_6)$alkoxy, $(C_1-C_6)$alkoxy-(C=O)—, CN, NO$_2$, NH$_2$, mono- or di$(C_1-C_6)$alkylamino or carboxy.

In a further possible subgroup of the compounds of formula I, $R_1$ is, independently at each occurrence, hydroxy, halogen, phenyl$(C_1-C_6)$alkoxy or NO$_2$.

In another possible subgroup of the compounds of formula I, $R_1$ is, independently at each occurrence, hydroxy, $(C_1-C_6)$alkyl, $(C_1-C_6)$alkoxy or halogen; for example, hydroxy or halogen.

In a further possible subgroup of the compounds of formula I, X is C(R$_5$)(R$_6$).

In a further possible subgroup of the compounds of formula I, $R_5$ is H.

In another possible subgroup of the compounds of formula I, $R_5$ is hydroxy.

In another possible subgroup of the compounds of formula I, $R_4$ and $R_5$ attached to adjacent carbon ring atoms form a bond between the carbon ring atoms to which they are attached.

In a further possible subgroup of the compounds of formula I. $R_6$ is unsubstituted phenyl.

In another possible subgroup of the compounds of formula I, $R_6$ is phenyl substituted with 1 or 2 substituent(s) $R_9$;

$R_9$ is, independently at each occurrence, hydroxy, $(C_2-C_6)$alkenyl, hydroxy$(C_1-C_6)$alkyl, halo$(C_1-C_6)$alkyl, hydroxy$(C_2-C_6)$alkenyl, hydroxy$(C_1-C_6)$alkoxy, halo$(C_1-C_6)$alkoxy, phenyl$(C_1-C_6)$alkoxy, $(C_1-C_6)$alkoxy$(C_1-C_6)$alkyl, $(C_2-C_6)$alkenyloxy$(C_1-C_6)$alkyl, $(C_1-C_6)$alkyl-(C=O)—, $(C_1-C_6)$alkoxy-(C=O)—, $(C_1-C_6)$alkoxy-(C=O)—$(C_1-C_6)$alkyl, $(C_1-C_6)$alkyl-S—, $(C_1-C_6)$alkyl-(C=O)—O—, $(C_1-C_6)$alkyl-(C=O)—O—$(C_1-C_6)$alkyl, hydroxy-(C=O)—$(C_1-C_6)$alkoxy, hydroxy-(C=O)—$(C_1-C_6)$alkoxy$(C_1-C_6)$alkyl, $(C_1-C_6)$alkoxy-(C=O)—$(C_1-C_6)$alkoxy$(C_1-C_6)$alkyl, $(C_1-C_6)$alkyl-S—$(C_1-C_6)$alkyl, hydroxy$(C_1-C_6)$alkyl-S—$(C_1-C_6)$alkyl, $(C_1-C_6)$alkoxy$(C_1-C_6)$alkyl-S—$(C_1-C_6)$alkyl, $(C_1-C_6)$alkyl-(C=O)—S—$(C_1-C_6)$alkyl, $(C_1-C_6)$alkoxy-(C=O)—$(C_1-C_6)$alkyl-S—$(C_1-C_6)$alkyl, $(C_1-C_6)$alkyl-S—$(C_1-C_6)$alkoxy$(C_1-C_6)$alkyl, hydroxy$(C_1-C_6)$alkyl-S—$(C_1-C_6)$alkoxy$(C_1-C_6)$alkyl, $(C_1-C_6)$alkoxy$(C_1-C_6)$alkyl-S—$(C_1-C_6)$alkoxy$(C_1-C_6)$alkyl, $(C_1-C_6)$alkyl-(O=S=O)—$(C_1-C_6)$alkyl, hydroxy$(C_1-C_6)$alkyl-(O=S=O)—$(C_1-C_6)$alkyl, $(C_1-C_6)$alkoxy$(C_1-C_6)$alkyl-(O=S=O)—$(C_1-C_6)$alkyl, $(C_1-C_6)$alkyl-(O=S=O)—$(C_1-C_6)$alkoxy$(C_1-C_6)$alkyl, hydroxy$(C_1-C_6)$alkyl-(O=S=O)—$(C_1-C_6)$alkoxy$(C_1-C_6)$alkyl, $(C_1-C_6)$alkoxy$(C_1-C_6)$alkyl-(O=S=O)—$(C_1-C_6)$alkoxy$(C_1-C_6)$alkyl, $(C_1-C_6)$alkyl-O—(O=S=O)—$(C_1-C_6)$alkyl, hydroxy$(C_1-C_6)$alkyl-O—(O=S=O)—$(C_1-C_6)$alkyl, $(C_1-C_6)$alkyl-(O=S=O)—O—$(C_1-C_6)$alkyl, hydroxy$(C_1-C_6)$alkyl-(O=S=O)—O—$(C_1-C_6)$alkyl, $(C_1-C_6)$alkyl-(O=S=O)—N(R$_{10}$)—$(C_1-C_6)$alkyl, hydroxy$(C_1-C_6)$alkoxy$(C_1-C_6)$alkyl, $(C_1-C_6)$alkoxy$(C_1-C_6)$alkoxy$(C_1-C_6)$alkyl, halo$(C_1-C_6)$alkoxy$(C_1-C_6)$alkyl, CN, NO$_2$, (R$_{10}$)$_2$N—, (R$_{10}$)$_2$N—$(C_1-C_6)$alkyl, (R$_{10}$)$_2$N—(C=O)—, (R$_{10}$)$_2$N—(C=O)—$(C_1-C_6)$alkoxy$(C_1-C_6)$alkyl, (R$_{10}$)$_2$N—(C=O)—$(C_1-C_6)$alkyl-S—$(C_1-C_6)$alkyl, (R$_{10}$)$_2$N—(C=O)—$(C_1-C_6)$alkyl-(O=S=O)—$(C_1-C_6)$alkyl, carboxy, R$_{11}$—(O=S=O)— or R$_{11}$—(O=S=O)—O—;

or $R_9$ and $R_9$ attached to adjacent carbon ring atoms form, together with the carbon ring atoms to which they are attached, a condensed phenyl ring, a condensed 5 or 6 membered unsaturated carbocyclic ring or a condensed 5 or 6 membered unsaturated heterocyclic ring containing 1 or 2 heteroatom(s) selected from O and S, wherein said phenyl, carbocyclic or heterocyclic ring is unsubstituted or substituted with 1 or 2 substituent(s) each independently being hydroxy, $(C_1-C_6)$alkyl, $(C_1-C_6)$alkoxy, hydroxy$(C_1-C_6)$alkyl, halo($C_1$-$C_6$)alkyl, ($C_1$-$C_6$)alkoxy($C_1$-$C_6$)alkyl, ($C_1$-$C_6$)alkyl-(C=O)— or ($C_1$-$C_6$)alkoxy-(C=O)—.

In another possible subgroup of the compounds of formula I, $R_6$ is phenyl substituted with 1 or 2 substituent(s) $R_9$;

$R_9$ is, independently at each occurrence, hydroxy, ($C_1$-$C_6$)alkyl, ($C_1$-$C_6$)alkoxy, halogen, hydroxy($C_1$-$C_6$)alkyl, halo($C_1$-$C_6$)alkyl, hydroxy($C_1$-$C_6$)alkoxy, halo($C_1$-$C_6$)alkoxy, phenyl($C_1$-$C_6$)alkoxy, ($C_1$-$C_6$)alkoxy-(C=O)—, ($C_1$-$C_6$)alkyl-(C=O)—O—, hydroxy-(C=O)—($C_1$-$C_6$)alkoxy, CN, ($R_{10}$)$_2$N—, ($R_{10}$)$_2$N—(C=O)—, $R_{11}$—(O=S=O)— or $R_{11}$—(O=S=O)—O—;

or $R_9$ and $R_9$ attached to adjacent carbon ring atoms form, together with the carbon ring atoms to which they are attached, a condensed 5 membered unsaturated heterocyclic ring containing 2 heteroatoms selected from O, wherein said heterocyclic ring is unsubstituted;

for example, $R_6$ is phenyl substituted with 1 substituent $R_9$ and $R_9$ is hydroxy, ($C_1$-$C_6$)alkyl, ($C_1$-$C_6$)alkoxy, halogen, hydroxy($C_1$-$C_6$)alkoxy or ($R_{10}$)$_2$N—.

In another possible subgroup of the compounds of formula I, X is C($R_7$)($R_8$).

In a further possible subgroup of the compounds of formula I, $R_7$ is H, hydroxy($C_1$-$C_6$)alkyl, ($C_1$-$C_6$)alkoxy($C_1$-$C_6$)alkyl or ($C_1$-$C_6$)alkoxy-(C=O)—; for example, H.

In a further possible subgroup of the compounds of formula I, $R_7$ is ($C_1$-$C_6$)alkyl, hydroxy($C_1$-$C_6$)alkyl, ($C_1$-$C_6$)alkoxy($C_1$-$C_6$)alkyl or ($C_1$-$C_6$)alkoxy-(C=O)—; for example, ($C_1$-$C_6$)alkyl.

In another possible subgroup of the compounds of formula I, $R_4$ and $R_7$ attached to adjacent carbon ring atoms form a bond between the carbon ring atoms to which they are attached.

In a further possible subgroup of the compounds of formula I, $R_8$ is ($C_2$-$C_6$)alkenyl, halogen, halo($C_1$-$C_6$)alkyl, hydroxy($C_2$-$C_6$)alkenyl, hydroxy($C_1$-$C_6$)alkoxy, halo($C_1$-$C_6$)alkoxy, phenyl($C_1$-$C_6$)alkoxy, ($C_1$-$C_6$)alkoxy($C_1$-$C_6$)alkyl, ($C_2$-$C_6$)alkenyloxy($C_1$-$C_6$)alkyl, ($C_1$-$C_6$)alkyl-(C=O)—, ($C_1$-$C_6$)alkoxy-(C=O)—($C_1$-$C_6$)alkyl, ($C_1$-$C_6$)alkyl-S—, hydroxy-(C=O)—($C_1$-$C_6$)alkoxy, hydroxy-(C=O)—($C_1$-$C_6$)alkoxy($C_1$-$C_6$)alkyl, ($C_1$-$C_6$)alkoxy-(C=O)—($C_1$-$C_6$)alkoxy($C_1$-$C_6$)alkyl, ($C_1$-$C_6$)alkyl-S—($C_1$-$C_6$)alkyl, hydroxy($C_1$-$C_6$)alkyl-S—($C_1$-$C_6$)alkyl, ($C_1$-$C_6$)alkoxy($C_1$-$C_6$)alkyl-S—($C_1$-$C_6$)alkyl, ($C_1$-$C_6$)alkyl-(C=O)—S—($C_1$-$C_6$)alkyl, ($C_1$-$C_6$)alkoxy-(C=O)—($C_1$-$C_6$)alkyl-S—($C_1$-$C_6$)alkyl, ($C_1$-$C_6$)alkyl-S—($C_1$-$C_6$)alkoxy($C_1$-$C_6$)alkyl, hydroxy($C_1$-$C_6$)alkyl-S—($C_1$-$C_6$)alkoxy($C_1$-$C_6$)alkyl, ($C_1$-$C_6$)alkoxy($C_1$-$C_6$)alkyl-S—($C_1$-$C_6$)alkoxy($C_1$-$C_6$)alkyl, ($C_1$-$C_6$)alkyl-(O=S=O)—($C_1$-$C_6$)alkyl, hydroxy($C_1$-$C_6$)alkyl-(O=S=O)—($C_1$-$C_6$)alkyl, ($C_1$-$C_6$)alkoxy($C_1$-$C_6$)alkyl-(O=S=O)—($C_1$-$C_6$)alkyl, ($C_1$-$C_6$)alkyl-(O=S=O)—($C_1$-$C_6$)alkoxy($C_1$-$C_6$)alkyl, hydroxy($C_1$-$C_6$)alkyl-(O=S=O)—($C_1$-$C_6$)alkoxy($C_1$-$C_6$)alkyl, ($C_1$-$C_6$)alkoxy($C_1$-$C_6$)alkyl-(O=S=O)—($C_1$-$C_6$)alkoxy($C_1$-$C_6$)alkyl, ($C_1$-$C_6$)alkyl-O—(O=S=O)—($C_1$-$C_6$)alkyl, hydroxy($C_1$-$C_6$)alkyl-O—(O=S=O)—($C_1$-$C_6$)alkyl, ($C_1$-$C_6$)alkyl-(O=S=O)—O—($C_1$-$C_6$)alkyl, hydroxy($C_1$-$C_6$)alkyl-(O=S=O)—O—($C_1$-$C_6$)alkyl, ($C_1$-$C_6$)alkyl-(O=S=O)—N($R_{10}$)—($C_1$-$C_6$)alkyl, hydroxy($C_1$-$C_6$)alkoxy($C_1$-$C_6$)alkyl, ($C_1$-$C_6$)alkoxy($C_1$-$C_6$)alkoxy($C_1$-$C_6$)alkyl, halo($C_1$-$C_6$)alkoxy($C_1$-$C_6$)alkyl, CN, $NO_2$, ($R_{10}$)$_2$N—, ($R_{10}$)$_2$N—($C_1$-$C_6$)alkyl, ($R_{10}$)$_2$N—(C=O)—($C_1$-$C_6$)alkoxy($C_1$-$C_6$)alkyl, ($R_{10}$)$_2$N—(C=O)—($C_1$-$C_6$)alkyl-S—($C_1$-$C_6$)alkyl, ($R_{10}$)$_2$N—(C=O)—($C_1$-$C_6$)alkyl-(O=S=O)—($C_1$-$C_6$)alkyl, $R_{11}$—(O=S=O)— or $R_{11}$—(O=S=O)—O—; for example, ($C_2$-$C_6$)alkenyl, halogen, hydroxy($C_2$-$C_6$)alkenyl, hydroxy($C_1$-$C_6$)alkoxy, halo($C_1$-$C_6$)alkoxy, ($C_2$-$C_6$)alkenyloxy($C_1$-$C_6$)alkyl, hydroxy-(C=O)—($C_1$-$C_6$)alkoxy, hydroxy-(C=O)—($C_1$-$C_6$)alkoxy($C_1$-$C_6$)alkyl, ($C_1$-$C_6$)alkoxy-(C=O)—($C_1$-$C_6$)alkoxy($C_1$-$C_6$)alkyl, hydroxy($C_1$-$C_6$)alkyl-S—($C_1$-$C_6$)alkyl, ($C_1$-$C_6$)alkoxy($C_1$-$C_6$)alkyl-S—($C_1$-$C_6$)alkyl, ($C_1$-$C_6$)alkyl-S—($C_1$-$C_6$)alkoxy($C_1$-$C_6$)alkyl, hydroxy($C_1$-$C_6$)alkyl-S—($C_1$-$C_6$)alkoxy($C_1$-$C_6$)alkyl, ($C_1$-$C_6$)alkoxy($C_1$-$C_6$)alkyl-S—($C_1$-$C_6$)alkoxy($C_1$-$C_6$)alkyl, hydroxy($C_1$-$C_6$)alkyl-(O=S=O)—($C_1$-$C_6$)alkyl, ($C_1$-$C_6$)alkoxy($C_1$-$C_6$)alkyl-(O=S=O)—($C_1$-$C_6$)alkyl, ($C_1$-$C_6$)alkyl-(O=S=O)—($C_1$-$C_6$)alkoxy($C_1$-$C_6$)alkyl, hydroxy($C_1$-$C_6$)alkyl-(O=S=O)—($C_1$-$C_6$)alkoxy($C_1$-$C_6$)alkyl, ($C_1$-$C_6$)alkoxy($C_1$-$C_6$)alkyl-(O=S=O)—($C_1$-$C_6$)alkoxy($C_1$-$C_6$)alkyl, ($C_1$-$C_6$)alkyl-O—(O=S=O)—($C_1$-$C_6$)alkyl, hydroxy($C_1$-$C_6$)alkyl-O—(O=S=O)—($C_1$-$C_6$)alkyl, ($C_1$-$C_6$)alkyl-(O=S=O)—O—($C_1$-$C_6$)alkyl, hydroxy($C_1$-$C_6$)alkyl-(O=S=O)—O—($C_1$-$C_6$)alkyl, ($C_1$-$C_6$)alkyl-(O=S=O)—N($R_{10}$)—($C_1$-$C_6$)alkyl, hydroxy($C_1$-$C_6$)alkoxy($C_1$-$C_6$)alkyl, ($C_1$-$C_6$)alkoxy($C_1$-$C_6$)alkoxy($C_1$-$C_6$)alkyl, CN, $NO_2$, ($R_{10}$)$_2$N—(C=O)—($C_1$-$C_6$)alkoxy($C_1$-$C_6$)alkyl, ($R_{10}$)$_2$N—(C=O)—($C_1$-$C_6$)alkyl-S—($C_1$-$C_6$)alkyl, ($R_{10}$)$_2$N—(C=O)—($C_1$-$C_6$)alkyl-(O=S=O)—($C_1$-$C_6$)alkyl or $R_{11}$—(O=S=O)—O—.

In another possible subgroup of the compounds of formula I, $R_8$ is hydroxy, ($C_1$-$C_6$)alkyl, ($C_2$-$C_6$)alkenyl, halogen, hydroxy($C_1$-$C_6$)alkyl, halo($C_1$-$C_6$)alkyl, hydroxy($C_1$-$C_6$)alkoxy, ($C_1$-$C_6$)alkoxy($C_1$-$C_6$)alkyl, ($C_2$-$C_6$)alkenyloxy($C_1$-$C_6$)alkyl, ($C_1$-$C_6$)alkyl-(C=O)—, ($C_1$-$C_6$)alkoxy-(C=O)—, ($C_1$-$C_6$)alkoxy-(C=O)—($C_1$-$C_6$)alkyl, ($C_1$-$C_6$)alkyl-(C=O)—O—($C_1$-$C_6$)alkyl, hydroxy-(C=O)—($C_1$-$C_6$)alkoxy($C_1$-$C_6$)alkyl, ($C_1$-$C_6$)alkoxy-(C=O)—($C_1$-$C_6$)alkoxy($C_1$-$C_6$)alkyl, hydroxy($C_1$-$C_6$)alkyl-S—($C_1$-$C_6$)alkyl, ($C_1$-$C_6$)alkyl-(C=O)—S—($C_1$-$C_6$)alkyl, ($C_1$-$C_6$)alkyl-(O=S=O)—O—($C_1$-$C_6$)alkyl, hydroxy($C_1$-$C_6$)alkoxy($C_1$-$C_6$)alkyl, ($C_1$-$C_6$)alkoxy($C_1$-$C_6$)alkoxy($C_1$-$C_6$)alkyl, halo($C_1$-$C_6$)alkoxy($C_1$-$C_6$)alkyl, CN, ($R_{10}$)$_2$N—($C_1$-$C_6$)alkyl, ($R_{10}$)$_2$N—(C=O)— or carboxy; for example, hydroxy, ($C_2$-$C_6$)alkenyl, halogen, hydroxy($C_1$-$C_6$)alkyl, halo($C_1$-$C_6$)alkyl, hydroxy($C_1$-$C_6$)alkoxy, ($C_1$-$C_6$)alkoxy($C_1$-$C_6$)alkyl, ($C_2$-$C_6$)alkenyloxy($C_1$-$C_6$)alkyl, ($C_1$-$C_6$)alkyl-(C=O)—, ($C_1$-$C_6$)alkoxy-(C=O)—($C_1$-$C_6$)alkyl, ($C_1$-$C_6$)alkyl-(C=O)—O—($C_1$-$C_6$)alkyl, hydroxy-(C=O)—($C_1$-$C_6$)alkoxy($C_1$-$C_6$)alkyl, ($C_1$-$C_6$)alkoxy-(C=O)—($C_1$-$C_6$)alkoxy($C_1$-$C_6$)alkyl, hydroxy($C_1$-$C_6$)alkyl-S—($C_1$-$C_6$)alkyl, ($C_1$-$C_6$)alkyl-(C=O)—S—($C_1$-$C_6$)alkyl, ($C_1$-$C_6$)alkyl-(O=S=O)—O—($C_1$-$C_6$)alkyl, hydroxy($C_1$-$C_6$)alkoxy($C_1$-$C_6$)alkyl, ($C_1$-$C_6$)alkoxy($C_1$-$C_6$)alkoxy($C_1$-$C_6$)alkyl, halo($C_1$-$C_6$)alkoxy($C_1$-$C_6$)alkyl, CN, ($R_{10}$)$_2$N—($C_1$-$C_6$)alkyl, ($R_{10}$)$_2$N—(C=O)— or carboxy; such as hydroxy($C_1$-$C_6$)alkyl, hydroxy($C_1$-$C_6$)alkoxy, ($C_1$-$C_6$)alkoxy($C_1$-$C_6$)alkyl or hydroxy($C_1$-$C_6$)alkoxy($C_1$-$C_6$)alkyl.

In another possible subgroup of the compounds of formula I, $R_4$ and $R_8$ attached to adjacent carbon ring atoms form, together with the carbon ring atoms to which they are attached, a condensed phenyl ring, wherein said phenyl ring is unsubstituted or substituted with 1 or 2 substituent(s) each independently being hydroxy, ($C_1$-$C_6$)alkyl, ($C_1$-$C_6$)alkoxy, hydroxy($C_1$-$C_6$)alkyl, halo($C_1$-$C_6$)alkyl, ($C_1$-$C_6$)alkoxy($C_1$-$C_6$)alkyl, ($C_1$-$C_6$)alkyl-(C=O)— or ($C_1$-$C_6$)alkoxy-(C=O)—; for example, $R_4$ and $R_8$ attached to adjacent carbon ring atoms form, together with the carbon ring atoms to which they are attached, a condensed phenyl ring, wherein said phenyl ring is substituted with 1 substituent being hydroxy($C_1$-$C_6$)alkyl or ($C_1$-$C_6$)alkoxy-(C=O)—.

In another possible subgroup of the compounds of formula I, $R_4$ and $R_8$ attached to adjacent carbon ring atoms form, together with the carbon ring atoms to which they are attached, a condensed 5 or 6 membered saturated or unsaturated carbocyclic ring or a condensed 5 or 6 membered saturated or unsaturated heterocyclic ring containing 1 or 2 heteroatom(s) selected from N, O, and S, wherein said carbocyclic or heterocyclic ring is unsubstituted or substituted with 1 or 2 substituent(s) each independently being hydroxy, $(C_1\text{-}C_6)$alkyl, $(C_1\text{-}C_6)$alkoxy, hydroxy$(C_1\text{-}C_6)$alkyl, halo$(C_1\text{-}C_6)$alkyl, $(C_1\text{-}C_6)$alkoxy$(C_1\text{-}C_6)$alkyl, $(C_1\text{-}C_6)$alkyl-(C=O)—, $(C_1\text{-}C_6)$alkoxy-(C=O)— or oxo.

In yet another possible subgroup of the compounds of formula I, $R_4$ and $R_8$ attached to adjacent carbon ring atoms form, together with the carbon ring atoms to which they are attached, a condensed 6 membered saturated carbocyclic ring, wherein said carbocyclic ring is unsubstituted.

In yet another possible subgroup of the compounds of formula I, $R_4$ and $R_8$ attached to adjacent carbon ring atoms form, together with the carbon ring atoms to which they are attached, a condensed 5 or 6 membered saturated or unsaturated heterocyclic ring containing 1 or 2 heteroatom(s) selected from N, O, and S, wherein said heterocyclic ring is unsubstituted or substituted with 1 or 2 substituent(s) each independently being hydroxy, $(C_1\text{-}C_6)$alkyl, $(C_1\text{-}C_6)$alkoxy, hydroxy$(C_1\text{-}C_6)$alkyl, halo$(C_1\text{-}C_6)$alkyl, $(C_1\text{-}C_6)$alkoxy$(C_1\text{-}C_6)$alkyl, $(C_1\text{-}C_6)$alkyl-(C=O)—, $(C_1\text{-}C_6)$alkoxy-(C=O)— or oxo.

In another possible subgroup of the compounds of formula I, $R_7$ and $R_8$ form, together with the carbon ring atom to which they are attached, a 5 or 6 membered saturated carbocyclic ring or a 5 or 6 membered saturated heterocyclic ring containing 1 or 2 heteroatom(s) selected from N, O, and S, wherein said carbocyclic or heterocyclic ring is unsubstituted or substituted with 1 or 2 substituent(s) each independently being hydroxy, $(C_1\text{-}C_6)$alkyl or oxo; for example, $R_7$ and $R_8$ form, together with the carbon ring atom to which they are attached, a 5 or 6 membered saturated heterocyclic ring containing 1 or 2 heteroatom(s) selected from N, O, and S, wherein said heterocyclic ring is unsubstituted or substituted with 1 or 2 substituent(s) each independently being hydroxy, $(C_1\text{-}C_6)$alkyl or oxo.

In a further possible subgroup of the compounds of formula I, X is $C(R_5)(R_6)$ or $C(R_7)(R_8)$;

Z is —$[C(R_4)_2]_n$— or a single bond;

$R_1$ is, independently at each occurrence, hydroxy, $(C_1\text{-}C_6)$alkyl, $(C_1\text{-}C_6)$alkoxy, halogen, phenyl$(C_1\text{-}C_6)$alkoxy or $NO_2$;

$R_2$ is, independently at each occurrence, H;

$R_3$ is, independently at each occurrence, H;

$R_4$ is, independently at each occurrence, H, hydroxy or $(C_1\text{-}C_6)$alkyl;

or $R_4$ and $R_4$ both attached to the same carbon ring atom form, together with the carbon ring atom to which they are attached, a —(C=O)— group;

$R_5$ is H;

or $R_4$ and $R_1$ attached to adjacent carbon ring atoms form a bond between the carbon ring atoms to which they are attached;

$R_6$ is phenyl unsubstituted or substituted with 1 or 2 substituent(s) $R_9$;

$R_7$ is H, $(C_1\text{-}C_6)$alkyl, hydroxy$(C_1\text{-}C_6)$alkyl, $(C_1\text{-}C_6)$alkoxy$(C_1\text{-}C_6)$alkyl or $(C_1\text{-}C_6)$alkoxy-(C=O)—;

or $R_4$ and $R_7$ attached to adjacent carbon ring atoms form a bond between the carbon ring atoms to which they are attached;

$R_8$ is hydroxy, $(C_1\text{-}C_6)$alkyl, $(C_2\text{-}C_6)$alkenyl, $(C_1\text{-}C_6)$alkoxy, halogen, hydroxy$(C_1\text{-}C_6)$alkyl, halo$(C_1\text{-}C_6)$alkyl, hydroxy$(C_1\text{-}C_6)$alkoxy, $(C_1\text{-}C_6)$alkoxy$(C_1\text{-}C_6)$alkyl, $(C_2\text{-}C_6)$alkenyloxy$(C_1\text{-}C_6)$alkyl, $(C_1\text{-}C_6)$alkyl-(C=O)—, $(C_1\text{-}C_6)$alkoxy-(C=O)—, $(C_1\text{-}C_6)$alkoxy-(C=O)—$(C_1\text{-}C_6)$alkyl, $(C_1\text{-}C_6)$alkyl-(C=O)—O—$(C_1\text{-}C_6)$alkyl, hydroxy-(C=O)—$(C_1\text{-}C_6)$alkoxy$(C_1\text{-}C_6)$alkyl, $(C_1\text{-}C_6)$alkoxy-(C=O)—$(C_1\text{-}C_6)$alkoxy$(C_1\text{-}C_6)$alkyl, hydroxy$(C_1\text{-}C_6)$alkyl-S—$(C_1\text{-}C_6)$alkyl, $(C_1\text{-}C_6)$alkyl-(C=O)—S—$(C_1\text{-}C_6)$alkyl, $(C_1\text{-}C_6)$alkyl-(O=S=O)—O—$(C_1\text{-}C_6)$alkyl, hydroxy$(C_1\text{-}C_6)$alkoxy$(C_1\text{-}C_6)$alkyl, $(C_1\text{-}C_6)$alkoxy$(C_1\text{-}C_6)$alkoxy$(C_1\text{-}C_6)$alkyl, halo$(C_1\text{-}C_6)$alkoxy$(C_1\text{-}C_6)$alkyl, CN, $(R_{10})_2$N—$(C_1\text{-}C_6)$alkyl, $(R_{10})_2$N—(C=O)—, carboxy, or $(C_1\text{-}C_6)$alkoxy-$(C_1\text{-}C_6)$alkoxy;

or $R_4$ and $R_8$ attached to adjacent carbon ring atoms form, together with the carbon ring atoms to which they are attached, a condensed phenyl ring, wherein said phenyl ring is unsubstituted or substituted with 1 or 2 substituent(s) each independently being hydroxy$(C_1\text{-}C_6)$alkyl or $(C_1\text{-}C_6)$alkoxy-(C=O)—;

or $R_4$ and $R_8$ attached to adjacent carbon ring atoms form, together with the carbon ring atoms to which they are attached, a condensed 6 membered saturated carbocyclic ring, wherein said carbocyclic ring is unsubstituted;

$R_9$ is, independently at each occurrence, hydroxy, $(C_1\text{-}C_6)$alkyl, $(C_1\text{-}C_6)$alkoxy, halogen, hydroxy$(C_1\text{-}C_6)$alkyl, halo$(C_1\text{-}C_6)$alkyl, hydroxy$(C_1\text{-}C_6)$alkoxy, halo$(C_1\text{-}C_6)$alkoxy, phenyl$(C_1\text{-}C_6)$alkoxy, $(C_1\text{-}C_6)$alkoxy-(C=O)—, $(C_1\text{-}C_6)$alkyl-(C=O)—O—, hydroxy-(C=O)—$(C_1\text{-}C_6)$alkoxy, CN, $(R_{10})_2$N—, $(R_{10})_2$N—(C=O)—, $R_{11}$—(O=S=O)— or $R_{11}$—(O=S=O)—O—;

or $R_9$ and $R_9$ attached to adjacent carbon ring atoms form, together with the carbon ring atoms to which they are attached, a condensed 5 or 6 membered unsaturated heterocyclic ring containing 1 or 2 heteroatom(s) selected from O, wherein said phenyl, carbocyclic or heterocyclic ring is unsubstituted;

$R_{10}$ is, independently at each occurrence, H or $(C_1\text{-}C_6)$alkyl, $R_{11}$ is, independently at each occurrence, $(C_1\text{-}C_6)$alkyl or halo$(C_1\text{-}C_6)$alkyl;

m is 0, 1 or 2; and n is 1 or 2.

In another possible subgroup of the compounds of formula I, X is $C(R_5)(R_6)$ or $C(R_7)(R_8)$;

Z is —$[C(R_4)_2]_n$—;

$R_1$ is, independently at each occurrence, hydroxy, $(C_1\text{-}C_6)$alkyl, or halogen;

$R_2$ is, independently at each occurrence, H;

$R_3$ is, independently at each occurrence, H;

$R_4$ is, independently at each occurrence, H;

$R_5$ is H;

$R_6$ is phenyl unsubstituted or substituted with 1 or 2 substituent(s) $R_9$;

$R_7$ is $(C_1\text{-}C_6)$alkyl;

$R_8$ is hydroxy$(C_1\text{-}C_6)$alkyl, hydroxy$(C_1\text{-}C_6)$alkoxy, $(C_1\text{-}C_6)$alkoxy$(C_1\text{-}C_6)$alkyl or hydroxy$(C_1\text{-}C_6)$alkoxy$(C_1\text{-}C_6)$alkyl, $R_9$ is, independently at each occurrence, hydroxy, $(C_1\text{-}C_6)$alkyl, $(C_1\text{-}C_6)$alkoxy, halogen, hydroxy$(C_1\text{-}C_6)$alkoxy or $(R_{10})_2$N—;

$R_{10}$ is, independently at each occurrence, H or $(C_1\text{-}C_6)$alkyl, m is 0 or 1;

n is 1.

In yet another possible subgroup of the compounds of formula I,

X is $C(R_5)(R_6)$ or $C(R_7)(R_8)$;

Z is a single bond;

$R_1$ is, independently at each occurrence, hydroxy, $(C_1\text{-}C_6)$alkyl, or halogen;

$R_2$ is, independently at each occurrence, H;

$R_3$ is, independently at each occurrence, H;

$R_4$ is, independently at each occurrence, H;

R₅ is H;
R₆ is phenyl unsubstituted or substituted with 1 or 2 substituent(s) R₉;
R₇ is H or (C₁-C₆)alkyl;
R₈ is hydroxy(C₁-C₆)alkyl, hydroxy(C₁-C₆)alkoxy, (C₁-C₆)alkoxy(C₁-C₆)alkyl or hydroxy(C₁-C₆)alkoxy(C₁-C₆)alkyl,
R₉ is, independently at each occurrence, hydroxy, (C₁-C₆)alkyl, (C₁-C₆)alkoxy, halogen, hydroxy(C₁-C₆)alkoxy or (R₁₀)₂N—;
R₁₀ is, independently at each occurrence, H or (C₁-C₆)alkyl,
m is 0 or 1;
n is 1.

In a further possible subgroup of the compounds of formula I, the compound is 1-(2,3-dihydrobenzo[1,4]dioxin-2-ylmethyl)-5-phenyl-1,2,3,6-tetrahydropyridine, 1-(2,3-dihydrobenzo[1,4]dioxin-2-ylmethyl)-3-phenylpiperidine, 1-(2,3-dihydrobenzo[1,4]dioxin-2-ylmethyl)-3-(2-methoxyphenyl)piperidine, 3-(4-chlorophenyl)-1-(2,3-dihydrobenzo[1,4]dioxin-2-ylmethyl)piperidine, 1-(2,3-dihydrobenzo[1,4]dioxin-2-ylmethyl)-3-(3-methoxyphenyl)piperidine, 1-(2,3-dihydrobenzo[1,4]dioxin-2-ylmethyl)-3-p-tolylpiperidine, 1-(2,3-dihydrobenzo[1,4]dioxin-2-ylmethyl)-3-(4-methoxyphenyl)piperidine, 1-(2,3-dihydrobenzo[1,4]dioxin-2-ylmethyl)-3-o-tolylpiperidine, 4-[1-(2,3-dihydrobenzo[1,4]dioxin-2-ylmethyl)piperidin-3-yl]phenol, 1-(2,3-dihydrobenzo[1,4]dioxin-2-ylmethyl)-3-(3-fluorophenyl)piperidine, 3-[1-(2,3-dihydrobenzo[1,4]dioxin-2-ylmethyl)piperidin-3-yl]phenol, 2-[1-(2,3-dihydrobenzo[1,4]dioxin-2-ylmethyl)piperidin-3-yl]phenol, (R*)-1-[(S)-1-(2,3-dihydrobenzo[1,4]dioxin-2-yl)methyl]-3-(2-fluorophenyl)piperidine, (S*)-1-[(S)-1-(2,3-dihydrobenzo[1,4]dioxin-2-yl)methyl]-3-(2-fluorophenyl)piperidine, (R*)-1-[(S)-1-(2,3-dihydrobenzo[1,4]dioxin-2-yl)methyl]-3-(3-fluorophenyl)piperidine, (R*)-1-[(S)-1-(2,3-dihydrobenzo[1,4]dioxin-2-yl)methyl]-3-(3-fluorophenyl)piperidine.HCl, (S*)-1-[(S)-1-(2,3-dihydrobenzo[1,4]dioxin-2-yl)methyl]-3-(3-fluorophenyl)piperidine, (R*)-1-[(S)-1-(2,3-dihydrobenzo[1,4]dioxin-2-yl)methyl]-3-(4-fluorophenyl)piperidine, (S*)-1-[(S)-1-(2,3-dihydrobenzo[1,4]dioxin-2-yl)methyl]-3-(4-fluorophenyl)piperidine, (R*)-1-[(S)-1-(2,3-dihydrobenzo[1,4]dioxin-2-yl)methyl]-3-(3-trifluoromethyl-phenyl)piperidine, (S*)-1-[(S)-1-(2,3-dihydrobenzo[1,4]dioxin-2-yl)methyl]-3-(3-trifluoromethyl-phenyl)piperidine, (R*)-1-[(S)-1-(2,3-dihydrobenzo[1,4]dioxin-2-yl)methyl]-3-(4-trifluoromethylphenyl)piperidine, (S*)-1-[(S)-1-(2,3-dihydrobenzo[1,4]dioxin-2-yl)methyl]-3-(4-trifluoromethylphenyl)piperidine, (R*)-1-[(S)-1-(2,3-dihydrobenzo[1,4]dioxin-2-yl)methyl]-3-(3-methoxyphenyl)piperidine, (R*)-1-[(S)-1-(2,3-dihydrobenzo[1,4]dioxin-2-yl)methyl]-3-(3-methoxyphenyl)piperidine.HCl, (S*)-1-[(S)-1-(2,3-dihydrobenzo[1,4]dioxin-2-yl)methyl]-3-(3-methoxyphenyl)piperidine, (R*)-3-{1-[(S)-1-(2,3-dihydrobenzo[1,4]dioxin-2-yl)methyl]piperidin-3-yl}phenol, (R*)-3-{1-[(S)-1-(2,3-dihydrobenzo[1,4]dioxin-2-yl)methyl]piperidin-3-yl}phenol.HCl, (3-{(R*)-1-[(S)-1-(2,3-dihydrobenzo[1,4]dioxin-2-yl)methyl]piperidin-3-yl}phenyl)methanol, acetic acid 3-{(S)-1-[(R*)-1-(2,3-dihydrobenzo[1,4]dioxin-2-yl)methyl]piperidin-3-yl}phenyl ester.HCl, 2-(3-{(R*)-1-[(S)-1-(2,3-dihydrobenzo[1,4]dioxin-2-yl)methyl]piperidin-3-yl}phenoxy)ethanol, 3-(3-{(R*)-1-[(S)-1-(2,3-dihydrobenzo[1,4]dioxin-2-yl)methyl]piperidin-3-yl}phenoxy)propan-1-ol, trifluoromethanesulfonic acid 3-{(R*)-1-[(S)-1-(2,3-dihydrobenzo[1,4]dioxin-2-yl)methyl]-piperidin-3-yl}phenyl ester, (3-{(R*)-1-[(S)-1-(2,3-dihydrobenzo[1,4]dioxin-2-yl)methyl]piperidin-3-yl}phenoxy)acetic acid, 3-{(R*)-1-[(S)-1-(2,3-dihydrobenzo[1,4]dioxin-2-yl)methyl]-piperidin-3-yl}-benzonitrile, 3-benzo[1,3]dioxol-5-yl-1-[(S)-1-(2,3-dihydrobenzo[1,4]dioxin-2-yl)methyl]-piperidine, 3-[(R*)-1-((S)-6-benzyloxy-2,3-dihydro-benzo[1,4]dioxin-2-ylmethyl)-piperidin-3-yl]-phenol, (S)-2-[(R*)-3-(3-hydroxy-phenyl)-piperidin-1-ylmethyl]-2,3-dihydro-benzo[1,4]dioxin-6-ol, 3-[(R*)-1-((S)-7-benzyloxy-2,3-dihydro-benzo[1,4]dioxin-2-ylmethyl)-piperidin-3-yl]-phenol, (S)-3-[(R*)-3-(3-hydroxy-phenyl)-piperidin-1-ylmethyl]-2,3-dihydro-benzo[1,4]dioxin-6-ol, 3-[(R*)-1-((S)-8-benzyloxy-2,3-dihydrobenzo[1,4]dioxin-2-ylmethyl)piperidin-3-yl]phenol, (S)-3-[(R*)-3-(3-hydroxy-phenyl)-piperidin-1-ylmethyl]-2,3-dihydro-benzo[1,4]dioxin-5-ol, (R*)-3-[1-((S)-7-fluoro-2,3-dihydrobenzo[1,4]dioxin-2-ylmethyl)piperidin-3-yl]phenol, 1-(2,3-dihydrobenzo[1,4]dioxin-2-ylmethyl)-5-methyl-1,2,3,6-tetrahydropyridine, 1-(2,3-dihydrobenzo[1,4]dioxin-2-ylmethyl)-3,5-dimethyl-1,2,3,6-tetrahydropyridine, [1-(2,3-dihydrobenzo[1,4]dioxin-2-ylmethyl)-1,2,5,6-tetrahydropyridin-3-yl]methanol, 2-(2,3-dihydrobenzo[1,4]dioxin-2-ylmethyl)-1,2,3,4,5,6,7,8-octahydroisoquinoline, 2-(2,3-dihydrobenzo[1,4]dioxin-2-ylmethyl)decahydroisoquinoline, 1-(2,3-dihydrobenzo[1,4]dioxin-2-ylmethyl)piperidine-3-carboxylic acid ethyl ester, [1-(2,3-dihydrobenzo[1,4]dioxin-2-ylmethyl)piperidin-3-yl]methanol, 1-(2,3-dihydrobenzo[1,4]dioxin-2-ylmethyl)-3-methylpiperidine-3-carboxylic acid ethyl ester, 1-(2,3-dihydrobenzo[1,4]dioxin-2-ylmethyl)-3-ethylpiperidine-3-carboxylic acid ethyl ester, [1-(2,3-dihydrobenzo[1,4]dioxin-2-ylmethyl)-3-methylpiperidin-3-yl]methanol, 1-(2,3-dihydrobenzo[1,4]dioxin-2-ylmethyl)-3-methoxymethyl-3-methylpiperidine, 1-(2,3-dihydrobenzo[1,4]dioxin-2-ylmethyl)-3-ethoxymethyl-3-methylpiperidine, 3-chloromethyl-1-(2,3-dihydrobenzo[1,4]dioxin-2-ylmethyl)-3-methylpiperidine, 2-[1-(2,3-dihydrobenzo[1,4]dioxin-2-ylmethyl)-3-methylpiperidin-3-yl]propan-2-ol, 1-(2,3-dihydrobenzo[1,4]dioxin-2-ylmethyl)-3-(1-methoxy-1-methylethyl)-3-methylpiperidine, 1-(2,3-dihydrobenzo[1,4]dioxin-2-ylmethyl)-3-hydroxymethyl-3-methylpiperidin-4-ol, acetic acid 1-(2,3-dihydrobenzo[1,4]dioxin-2-ylmethyl)-3-methylpiperidin-3-ylmethyl ester, methanesulfonic acid 1-(2,3-dihydrobenzo[1,4]dioxin-2-ylmethyl)-3-methylpiperidin-3-ylmethyl ester, [1-(2,3-dihydrobenzo[1,4]dioxin-2-ylmethyl)-3-ethylpiperidin-3-yl]methanol, 1-(2,3-dihydrobenzo[1,4]dioxin-2-ylmethyl)-3-ethyl-3-methoxymethylpiperidine, 1-(2,3-dihydrobenzo[1,4]dioxin-2-ylmethyl)-3-methoxymethoxymethyl-3-methylpiperidine, 1-[1-(2,3-dihydrobenzo[1,4]dioxin-2-ylmethyl)-3-ethylpiperidin-3-yl]ethanone, 1-[1-(2,3-dihydrobenzo[1,4]dioxin-2-ylmethyl)-3-ethylpiperidin-3-yl]ethanol, 3-allyloxymethyl-1-(2,3-dihydrobenzo[1,4]dioxin-2-ylmethyl)-3-ethylpiperidine, 2-[1-(2,3-dihydrobenzo[1,4]dioxin-2-ylmethyl)-3-ethylpiperidin-3-yl-methoxy]ethanol, 3-allyloxymethyl-1-(2,3-dihydrobenzo[1,4]dioxin-2-ylmethyl)-3-methyl-piperidine, 3-allyl-1-(2,3-dihydrobenzo[1,4]dioxin-2-ylmethyl)-piperidine-carboxylic acid ethyl ester, [3-allyl-1-(2,3-dihydrobenzo[1,4]dioxin-2-ylmethyl)piperidin-3-yl]methanol, 3-allyl-1-(2,3-dihydrobenzo[1,4]dioxin-2-ylmethyl)-3-methoxymethylpiperidine, 3-allyl-1-(2,3-dihydrobenzo[1,4]dioxin-2-ylmethyl)-3-ethoxymethylpiperidine, 1-(2,3-dihydrobenzo[1,4]dioxin-2-ylmethyl)-3-methyl-3-(2,2,2-trifluoroethoxymethyl)-piperidine, 2-[1-(2,3-dihydrobenzo[1,4]dioxin-2-ylmethyl)-3-methylpiperidin-3-ylmethoxy]ethanol, [1-(2,3-dihydrobenzo[1,4]dioxin-2-ylmethyl)piperidin-3-yl]acetic acid ethyl ester, 2-[1-(2,3-dihydrobenzo[1,4]dioxin-2-ylmethyl)piperidin-3-yl]ethanol, 1-(2,3-dihydrobenzo[1,4]dioxin-2-ylmethyl)-3-(2-methoxyethyl)piperidine, 1-(2,3-dihydrobenzo[1,4]dioxin-2-ylmethyl)piperidine-3-carboxylic acid amide, 1-(2,3-dihydrobenzo[1,4]dioxin-2-ylmethyl)piperidine-3-carbonitrile, C-[1-(2,3-dihydrobenzo[1,4]dioxin-2-ylmethyl)piperidin-3-yl]methylamine, 1-(2,3-dihydrobenzo[1,4]dioxin-2-ylmethyl)piperidin-3-ol, 2-(2,3-dihydrobenzo[1,4]dioxin-2-ylmethyl)-1,2,3,4-tetrahydroisoquinoline-8-carboxylic acid methyl ester, [2-(2,3-dihydrobenzo[1,4]dioxin-2-ylmethyl)-1,2,3,4-tetrahydroisoquinolin-8-yl]methanol, (S)-1-((R)-2,3-dihydrobenzo[1,4]dioxine-2-carbonyl)-3-methylpiperidine-3-carboxylic acid ethyl ester, lithium (S)-1-[(S)-1-(2,3-dihydrobenzo[1,4]dioxin-2-yl)methyl]-3-methyl-piperidine-3-carboxylate, {(S)-1-[(S)-1-(2,3-dihydrobenzo[1,4]dioxin-2-yl)methyl]-3-methylpiperidin-3-yl}methanol, 2-{(S)-1-[(S)-1-(2,3-dihydrobenzo[1,4]dioxin-2-yl)methyl]-3-methylpiperidin-3-ylmethoxy}-ethanol, 2-{(S)-1-[(S)-1-(2,3-dihydrobenzo[1,4]dioxin-2-yl)methyl]-3-methylpiperidin-3-ylmethoxy}-ethanol D-tartrate, (S)-1-[(S)-1-(2,3-dihydrobenzo[1,4]dioxin-2-yl)methyl]-3-(2-methoxyethoxymethyl)-3-methylpiperidine, (S)-1-[(S)-1-(2,3-dihydrobenzo[1,4]dioxin-2-yl)methyl]-3-methyl-3-(2,2,2-trifluoroethoxymethyl)piperidine, methanesulfonic acid (S)-1-[(S)-1-(2,3-dihydrobenzo[1,4]dioxin-2-yl)methyl]-3-methyl-piperidin-3-ylmethyl ester, thioacetic acid S-{(S)-1-[(S)-1-(2,3-dihydrobenzo[1,4]dioxin-2-yl)methyl]-3-methylpiperidin-3-ylmethyl}ester, 2-{(S)-1-[(S)-1-(2,3-dihydrobenzo[1,4]dioxin-2-yl)methyl]-3-methylpiperidin-3-ylmethyl-sulfanyl}ethanol, {(S)-1-[(S)-1-(2,3-dihydrobenzo[1,4]dioxin-2-yl)methyl]-3-methylpiperidin-3-ylmethoxy}acetic acid tert-butyl ester, sodium {(S)-1-[(S)-1-(2,3-dihydrobenzo[1,4]dioxin-2-yl)methyl]-3-methylpiperidin-3-yl-methoxy}acetate, 2-[(S)-1-((S)-7-fluoro-2,3-dihydrobenzo[1,4]dioxin-2-ylmethyl)-3-methylpiperidin-3-yl-methoxy]ethanol, 1-(2,3-dihydrobenzo[1,4]dioxin-2-ylmethyl)-3-fluoro-piperidine-3-carboxylic acid ethyl ester, [1-(2,3-dihydrobenzo[1,4]dioxin-2-ylmethyl)-3-fluoro-piperidin-3-yl]methanol, (S)-1-[(S)-1-(2,3-dihydro-benzo[1,4]dioxin-2-yl)methyl]-3-methyl-piperidine-3-carboxylic acid ethyl ester, [(S)-1-((S)-7-fluoro-2,3-dihydro-benzo[1,4]dioxin-2-ylmethyl)-3-methyl-piperidin-3-yl]-methanol, (S)-1-((S)-7-fluoro-2,3-dihydro-benzo[1,4]dioxin-2-ylmethyl)-3-methoxymethyl-3-methyl-piperidine, (S)-1-((S)-7-fluoro-2,3-dihydro-benzo[1,4]dioxin-2-ylmethyl)-3-methoxymethyl-3-methyl-piperidine.HCl, (S)-1-[(S)-1-(2,3-dihydro-benzo[1,4]dioxin-2-yl)methyl]-3-methoxymethyl-3-methyl-piperidine, 3-{(R*)-1-[(S)-1-(2,3-dihydro-benzo[1,4]dioxin-2-yl)methyl]-piperidin-3-yl}-phenylamine, (R*)-3-{1-[(S)-1-(2,3-dihydrobenzo[1,4]dioxin-2-yl)methyl]piperidin-3-yl}phenol oxalate, (S)-2-[(R*)-3-(3-hydroxy-phenyl)-piperidin-1-ylmethyl]-2,3-dihydro-benzo[1,4]dioxin-5-ol, 1-[(S)-1-(2,3-dihydro-benzo[1,4]dioxin-2-yl)methyl]-3-(2-methoxy-phenyl)-pyrrolidine, (S)-1-[(S)-1-(2,3-dihydro-benzo[1,4]dioxin-2-yl)methyl]-3-(2-fluoro-ethoxymethyl)-3-methyl-piperidine.HCl, (R*)-1-[(S)-1-(2,3-dihydro-benzo[1,4]dioxin-2-yl)methyl]-3-(3-fluoromethoxy-phenyl)-piperidine, 1-(2,3-dihydro-benzo[1,4]dioxin-2-ylmethyl)-pyrrolidine-3-carboxylic acid methyl ester, [1-(2,3-dihydro-benzo[1,4]dioxin-2-ylmethyl)-pyrrolidin-3-yl]-methanol, 2-[1-(2,3-dihydro-benzo[1,4]dioxin-2-ylmethyl)-pyrrolidin-3-ylmethoxy]-ethanol, 1-(2,3-dihydro-benzo[1,4]dioxin-2-ylmethyl)-3-methyl-pyrrolidine-3-carboxylic acid methyl ester, [1-(2,3-dihydro-benzo[1,4]dioxin-2-ylmethyl)-3-methyl-pyrrolidin-3-yl]-methanol, 2-[1-(2,3-dihydro-benzo[1,4]dioxin-2-ylmethyl)-3-methyl-pyrrolidin-3-ylmethoxy]-ethanol, 1-(2,3-dihydro-benzo[1,4]dioxin-2-ylmethyl)-3-methoxymethyl-3-methyl-pyrrolidine or 3-[(R)-1-((S)-7-nitro-2,3-dihydro-benzo[1,4]dioxin-2-ylmethyl)-piperidin-3-yl]-phenol.

It is evident to a person skilled in the art that, in the compounds of formula I, when the substituents $R_9$ and $R_9$ attached to adjacent carbon ring atoms form, together with the carbon ring atoms to which they are attached, a condensed 5 or 6 membered unsaturated carbocyclic ring or a condensed 5 or 6 membered unsaturated heterocyclic ring, said carbocyclic ring or heterocyclic ring may have further unsaturated bonds in addition to the unsaturated bond between the carbon ring atoms, to which said substituents are attached.

The terms employed herein have the meanings indicated below. The term "at least one" employed in the meanings below refers to one or several, such as one. For example, the term "at least one halogen" refers to one or several halogens, such as one halogen.

The term "hydroxy", as employed herein as such or as part of another group, refers to a —OH group.

The term "$(C_1-C_6)$alkyl", as employed herein as such or as part of another group, refers to a straight or branched chain saturated hydrocarbon group having 1, 2, 3, 4, 5 or 6 carbon atom(s). Representative examples of $(C_1-C_6)$alkyl include, but are not limited to, methyl, ethyl, n-propyl, iso-propyl, n-butyl, iso-butyl, sec-butyl, tert-butyl, n-pentyl, iso-pentyl, and n-hexyl.

The term "$(C_1-C_6)$alkoxy", as employed herein as such or as part of another group, refers to an $(C_1-C_6)$alkyl group, as defined herein, appended to the parent molecular moiety through an oxygen atom. Representative examples of $(C_1-C_6)$alkoxy include, but are not limited to, methoxy, ethoxy, n-propoxy, n-butoxy, iso-butoxy, sec-butoxy, tert-butoxy, 2,2-dimethylpropoxy, 3-methylbutoxy, and n-hexoxy.

The term "halo" or "halogen", as employed herein as such or as part of another group, refers to fluorine, chlorine, bromine or iodine.

The term "halo$(C_1-C_6)$alkyl", as employed herein, refers to at least one halogen, as defined herein, appended to the parent molecular moiety through an $(C_1-C_6)$alkyl group, as defined herein. When there are several halogens, the halogens can be identical or different. Representative examples of halo($C_1$-$C_6$)alkyl include, but are not limited to, fluoromethyl, chloromethyl, difluoromethyl, trifluoromethyl, 2-chloroethyl, 3-bromopropyl, and 2-chloropropyl.

The term "phenyl$(C_1-C_6)$alkoxy", as employed herein, refers to at least one phenyl group appended to the parent molecular moiety through an $(C_1-C_6)$alkoxy group, as defined herein. Representative examples of phenyl($C_1$-$C_6$)alkoxy include, but are not limited to, phenylmethoxy, 2-phenylethoxy, and 3-phenylpropoxy.

The term "amino", as employed herein as part of another group, refers to a —$NH_2$ group.

The term "mono$(C_1-C_6)$alkylamino", as employed herein, refers to one $(C_1-C_6)$alkyl group, as defined herein, appended to the parent molecular moiety through an amino group, as defined herein. Representative examples of mono($C_1$-$C_6$)alkylamino include, but are not limited to, N-methylamino, N-ethylamino, and N-butylamino.

The term "di$(C_1-C_6)$alkylamino", as employed herein, refers to two $(C_1-C_6)$alkyl groups, as defined herein, appended to the parent molecular moiety through an amino group, as defined herein. The $(C_1-C_6)$alkyl groups can be identical or different. Representative examples of di($C_1$-$C_6$)alkylamino include, but are not limited to, N,N-dimethylamino and N,N-diethylamino.

The term "carboxy", as employed herein, refers to a —COOH group.

The term "$(C_2-C_6)$alkenyl", as employed herein as such or as part of another group, refers to a straight or branched chain hydrocarbon group having 2, 3, 4, 5 or 6 carbon atoms and containing at least one carbon-carbon double bond. Representative examples of $(C_2-C_6)$alkenyl include, but are not limited to, ethenyl and prop-2-enyl.

The term "hydroxy$(C_1-C_6)$alkyl", as employed herein as such or as part of another group, refers to at least one hydroxy group, as defined herein, appended to the parent molecular moiety through an $(C_1-C_6)$alkyl group, as defined herein. Representative examples of hydroxy$(C_1-C_6)$alkyl include, but are not limited to, hydroxymethyl, 1-hydroxyethyl, 2-hydroxyethyl, 2,2-dihydroxyethyl, 1-hydroxypropyl, 3-hydroxypropyl, 1-hydroxy-1-methylethyl, and 1-hydroxy-1-methylpropyl.

The term "hydroxy$(C_2-C_6)$alkenyl", as employed herein, refers to at least one hydroxy group, as defined herein, appended to the parent molecular moiety through an $(C_2-C_6)$ alkenyl group, as defined herein. Representative examples of hydroxy$(C_2-C_6)$alkenyl include, but are not limited to, 1-hydroxyethenyl, 2-hydroxyethenyl, and 1-hydroxyprop-2-enyl.

The term "$(C_1-C_6)$alkoxy$(C_1-C_6)$alkyl", as employed herein as such or as part of another group, refers to at least one $(C_1-C_6)$alkoxy group, as defined herein, appended to the parent molecular moiety through an $(C_1-C_6)$alkyl group, as defined herein. When there are several $(C_1-C_6)$alkoxy groups, the $(C_1-C_6)$alkoxy groups can be identical or different. Representative examples of $(C_1-C_6)$alkoxy$(C_1-C_6)$alkyl include, but are not limited to, methoxymethyl, ethoxymethyl, propoxymethyl, 2-methoxyethyl, 2-ethoxyethyl, 2,2-dimethoxyethyl, 1-methyl-2-propoxyethyl, 1-methoxy-1-methylethyl, and 4-methoxybutyl.

The term "$(C_2-C_6)$alkenyloxy", as employed herein as part of another group, refers to an $(C_2-C_6)$alkenyl group, as defined herein, appended to the parent molecular moiety through an oxygen atom. Representative examples of $(C_2-C_6)$ alkenyloxy include, but are not limited to, ethenyloxy, prop-2-enyloxy, bute-2-nyloxy, and hex-3-enyloxy.

The term "$(C_2-C_6)$alkenyloxy$(C_1-C_6)$alkyl", as employed herein, refers to at least one $(C_2-C_6)$alkenyloxy group, as defined herein, appended to the parent molecular moiety through an $(C_1-C_6)$alkyl group, as defined herein. When there are several $(C_2-C_6)$alkenyloxy groups, the $(C_2-C_6)$alkenyloxy groups can be identical or different. Representative examples of $(C_2-C_6)$alkenyloxy$(C_1-C_6)$alkyl include, but are not limited to, prop-2-enyloxymethyl and ethenyloxyethyl.

The term "hydroxy$(C_1-C_6)$alkoxy", as employed herein as such or as part of another group, refers to at least one hydroxy group, as defined herein, appended to the parent molecular moiety through an $(C_1-C_6)$alkoxy group, as defined herein. Representative examples of hydroxy$(C_1-C_6)$alkoxy include, but are not limited to, hydroxymethoxy, dihydroxymethoxy, 2-hydroxyethoxy, 2-hydroxypropoxy, 3-hydroxypropoxy, 2-hydroxybutoxy, and 2-hydroxy-1-methylethoxy.

The term "$(C_1-C_6)$alkoxy$(C_1-C_6)$alkoxy", as employed herein as such or as part of another group, refers to at least one $(C_1-C_6)$alkoxy group, as defined herein, appended to the parent molecular moiety through an $(C_1-C_6)$alkoxy group, as defined herein. The $(C_1-C_6)$alkoxy groups can be identical or different. Representative examples of $(C_1-C_6)$alkoxy$(C_1-C_6)$ alkoxy include, but are not limited to, methoxymethoxy, propoxymethoxy, 2-methoxyethoxy, 2-ethoxyethoxy, 2-butoxyethoxy, 2,2-dimethoxyethoxy, 1-methyl-2-propoxyethoxy, 2-methoxypropoxy and 4-methoxybutoxy.

The term "halo$(C_1-C_6)$alkoxy", as employed herein as such or as part of another group, refers to at least one halogen, as defined herein, appended to the parent molecular moiety through an $(C_1-C_6)$alkoxy group, as defined herein. When there are several halogens, the halogens can be identical or different. Representative examples of halo$(C_1-C_6)$alkoxy include, but are not limited to, fluoromethoxy, chloromethoxy, difluoromethoxy, trifluoromethoxy, 2-bromoethoxy, 2,2,2-trichloroethoxy, 3-bromopropoxy, 2-chloropropoxy, and 4-chlorobutoxy.

The term "oxo", as employed herein, refers to a =O group.

The expression "compounds of the invention" as employed herein refers to the compounds of formula I.

Pharmaceutically acceptable salts, e.g. metal salts and acid addition salts, with both organic and inorganic acids, are known in the field of pharmaceuticals. Representative examples of pharmaceutically acceptable metal salts include, but are not limited to, lithium, sodium, potassium, calcium, magnesium, aluminum and zinc salts. Representative examples of pharmaceutically acceptable acid addition salts include, but are not limited to, chlorides, bromides, sulfates, nitrates, phosphates, sulfonates, methane sulfonates, formates, tartrates, maleates, citrates, benzoates, salicylates, ascorbates, acetates and oxalates.

Pharmaceutically acceptable esters, when applicable, may be prepared by known methods using pharmaceutically acceptable acids that are conventional in the field of pharmaceuticals and that retain the pharmacological properties of the free form. Non-limiting examples of these esters include esters of aliphatic or aromatic alcohols. Representative examples of pharmaceutically acceptable esters include, but are not limited to, methyl, ethyl, n-propyl, iso-propyl, n-butyl, iso-butyl, sec-butyl, tert-butyl, and benzyl esters.

The invention includes within its scope all the possible geometric isomers, e.g. Z and E isomers (cis and trans isomers), of the compounds as well as all the possible optical isomers, e.g. diastereomers and enantiomers, of the compounds. Furthermore, the invention includes in its scope both the individual isomers and any mixtures thereof, e.g. racemic mixtures. The individual isomers may be obtained using the corresponding isomeric forms of the starting material or they may be separated after the preparation of the end compound according to conventional separation methods. For the separation of optical isomers, e.g. enantiomers, from the mixture thereof, conventional resolution methods, e.g. fractional crystallization, may be used.

The compounds of formula I can be prepared by a variety of synthetic routes analogously to or according to methods known in the literature using suitable starting materials. The starting materials depicted below in formulae A, B, C, and D are commercially available or can be prepared via synthetic routes known in the literature.

Suitable starting materials containing the benzodioxane moiety are compounds of formulae A and B:

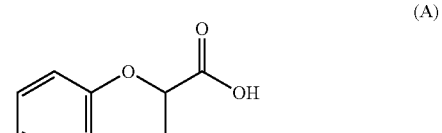

(A)

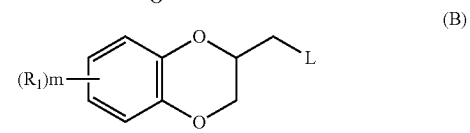

(B)

wherein $R_1$ and m are as defined above and L is a leaving group, e.g. halogen, mesylate or tosylate.

2,3-Dihydrobenzo[1,4]dioxine-2-carboxylic acid (formula A) is commercially available and easily resolvable to its enantiomers as described in *Tetrahedron: Asymmetry*, 16 (2005) 1639. Compounds of formula B can be prepared according to known methods.

Suitable starting materials containing the azacycle moiety are suitably substituted piperidines or homopiperidines and also, in some cases, pyridines. Such compounds are compounds of formulae C, D, and E:

wherein X and Z are as defined above, R represents $R_6$ or $R_8$ as defined above, and R' and R'' represent alkyl groups. Although not shown in their formulae, the heterocyclic rings in compounds of formulae C, D, and E can contain further suitable substituents. Compounds of formula E having two substituents attached to the same carbon atom can be prepared, for example, via α-alkylation of suitable piperidine carboxylates as described in *Org. Lett.*, 7 (2005) 55 or via construction of the piperidine ring from a proper open chain precursor, e.g. reduction of suitably alkylated 2-cyanoacetates. The ester group in compounds of formula E is further transformable to a wide variety of other functional groups.

In general, compounds of formula I can be prepared analogously or according to scheme 1, wherein X and Z are as defined above:

Scheme 1

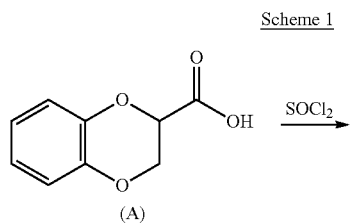

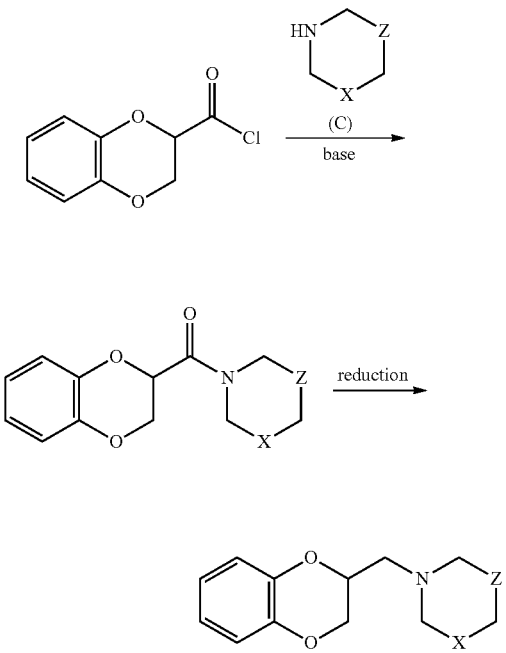

Another route for preparing amide intermediates of scheme 1, wherein Z is a single bond, proceeds via reaction of a suitable amine and a suitable iteconate analog as described in *J. Org. Chem.*, 26 (1961) 1519-1524.

A further route for preparing compounds of formula I is shown in scheme 2, wherein X, Z, $R_1$, and m are as defined above:

Scheme 2

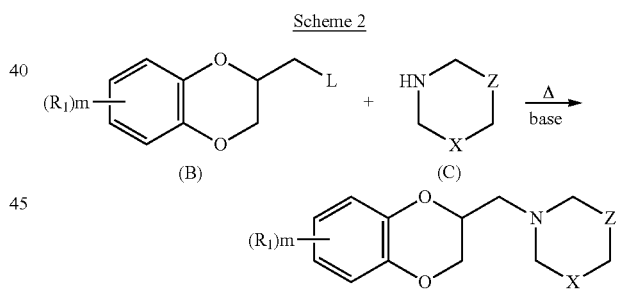

Compounds of formula I, wherein $R_5$ or $R_7$ is H, can be prepared via N-alkylation of suitably substituted pyridines followed by reduction as illustrated in scheme 3, wherein $R_1$, m, L, and R are as defined above:

Scheme 3

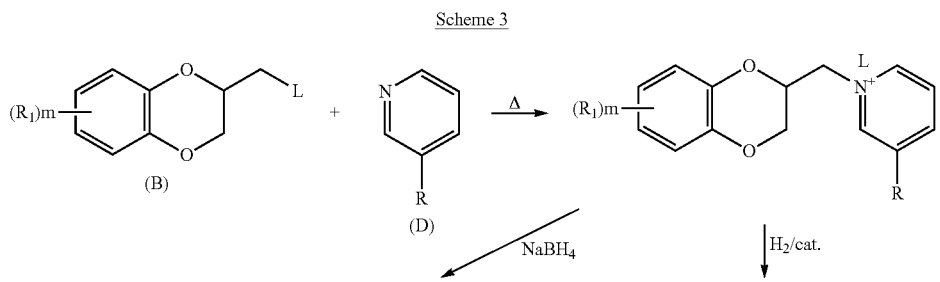

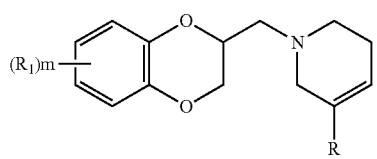
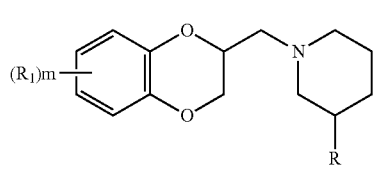

-continued

Resolution of the compounds of formula I that are racemic can be carried out, if desired, for example, by converting the racemic compound into its diastereomeric salt mixture by reaction with an optically active acid and subsequent separation of the diastereomers by crystallization. Representative examples of said optically active acids include, but are not limited to, D-tartaric acid and dibenzoyl-D-tartaric acid.

A person skilled in the art realizes that any starting material or intermediate in the reactions described above can be protected, if necessary, in a manner known in the art. Any protected functionality can subsequently be deprotected in a manner known in the art.

The synthetic routes described above are meant to illustrate the preparation of the compounds of formula I and the preparation is by no means limited thereto, i.e. there are also other possible synthetic methods which are within the general knowledge of a person skilled in the art.

The compounds of formula I may be converted, if desired, into their pharmaceutically acceptable salt or ester form using methods known in the art.

The present invention will be explained in more detail by the following examples. The examples are meant for illustrating purposes only and do not limit the scope of the invention defined in the claims.

Abbreviations: DCM=dichloromethane, DIPEA=N,N-diisopropylethylamine, DMF=N,N-dimethylformamide, EtOAc=ethyl acetate, IPA=isopropanol, LC-MS=liquid chromatography-mass spectrometry, RT=room temperature, THF=tetrahydrofuran, TLC=thin layer chromatography.

Column chromatography was performed on Silica gel 60 obtained from Merck, or using a CombiFlash instrument together with Redisep columns, both provided by Teledyne ISCO. Microwave heating was performed using an Emrys Optimiser microwave reactor from Personal Chemistry or an Initiator 2.0 microwave reactor from Biotage. The structures of the products were confirmed by $^1$H NMR. The spectra were measured with a Bruker Avance 400 instrument. LC-MS analyses were performed using Waters 2690 Alliance HPLC and Waters Micromass ZQ4000 single quadrupole mass spectrometer using ESI.

Preparation of Starting Materials 3-(Piperidin-3-yl)phenol.HBr can be prepared from 3-(3-methoxyphenyl)piperidine as described in *J. Med. Chem.,* 24 (1981) 1475.

2-(Piperidin-3-yl)phenol.HBr was prepared by heating 3-(2-methoxyphenyl)piperidine.HCl (46 mg, 0.20 mmol) with 48% HBr in a microwave reactor at 120° C. for one hour. After evaporation, 61 mg of the title compound was obtained.

4-(Piperidin-3-yl)phenol.HBr was prepared by heating 3-(4-methoxyphenyl)piperidine.HCl (46 mg, 0.20 mmol) with 48% HBr in a microwave reactor at 120° C. for one hour. After evaporation, 53 mg of the title compound was obtained.

(R*)-3-(3-Methoxyphenyl)piperidine was prepared by crystallographic resolution with D-(−)-tartaric acid as described for an analogous substrate in *Tetrahedron Lett.,* 35 (1994) 9063.

(R*)-3-(Piperidin-3-yl)phenol.HBr or .HCl was prepared from (R*)-3-(3-methoxyphenyl)piperidine by the method described above for the racemate. Concentrated HCl can be used instead of 48% HBr.

(R)-2,3-Dihydrobenzo[1,4]dioxine-2-carboxylic acid was obtained from the commercially available racemate as described in *Tetrahedron: Asymmetry,* 16 (2005) 1639.

(R)-2,3-Dihydrobenzo[1,4]dioxine-2-carbonyl chloride can be prepared by heating (R)-2,3-dihydrobenzo[1,4]dioxine-2-carboxylic acid at 70° C. in the presence of excess thionyl chloride for 1-8 h. Catalytic amount of DMF can be added. Evaporation to dryness gives the title compound in high yield.

Methanesulfonic acid (R)-(7-fluoro-2,3-dihydrobenzo[1,4]dioxin-2-yl)methyl ester was prepared in four steps from 5'-fluoro-2'-hydroxyacetophenone according to analogous methods described in the literature (*J. Med. Chem.,* 30 (1987) 814 and U.S. Pat. No. 5,935,973).

Preparation of Intermediates

Intermediate A1: (R)-2,3-Dihydrobenzo[1,4]dioxin-2-yl-[(R*)-3-(2-fluorophenyl)piperidin-1-yl]methanone Intermediate A2: (R)-2,3-Dihydrobenzo[1,4]dioxin-2-yl-[(S*)-3-(2-fluorophenyl)piperidin-1-yl]methanone (R)-2,3-Dihydrobenzo[1,4]dioxine-2-carbonyl chloride (46 mg, 0.23 mmol) in DCM (1 ml) was added to a cold solution of 3-(2-fluorophenyl)piperidine HCl (50 mg, 0.23 mmol) and DCM (1 ml). Triethylamine (56 mg, 0.55 mmol) was added. The mixture was stirred for 50 min. Water (1 ml) was added and the aqueous phase extracted with DCM (3×1 ml). The combined organics were absorbed on silica. The mixture was purified by flash chromatography using heptane/EtOAc as eluent. The first eluting diastereomer was collected to afford 24 mg of A1 (rotameric mixture).

$^1$H NMR (CDCl$_3$): δ 1.63-1.73 (m, 1H), 1.79-1.96 (m, 2H), 2.03-2.14 (m, 1H), 2.63-2.75 (m, 0.5H), 2.80 (t, 0.5H), 2.98-3.16 (m, 1.5H), 3.20 (t, 0.5H), 4.14-4.26 (m, 1H), 4.29-4.38 (m, 1H), 4.48-4.55 (m, 1H), 4.67-4.75 (m, 1H), 4.84-4.93 (m, 1H) 6.78-7.06 (m, 7H), 7.26-7.33 (m, 1H).

The second eluting diastereomer was collected to afford 25 mg of A2 (rotameric mixture).

$^1$H NMR (CDCl$_3$): δ 1.60-1.76 (m, 1H), 1.78-1.95 (m, 2H), 2.02-2.13 (m, 1H), 2.62-2.71 (m, 0.7H), 2.80 (t, 0.3H), 2.98-3.35 (m, 2H), 4.14-4.25 (m, 1H), 4.29-4.39 (m, 1H), 4.45-4.57 (m, 1H), 4.65-4.74 (m, 1H), 4.76-4.82 (m, 0.7H), 4.86-4.93 (m, 0.3H), 6.81-7.30 (m, 8H).

Intermediate A3: (R)-2,3-Dihydrobenzo[1,4]dioxin-2-yl-[(R*)-3-(3-fluorophenyl)piperidin-1-yl]methanone Intermediate A4: (R)-2,3-Dihydrobenzo[1,4]dioxin-2-yl-[(S*)-3-(3-fluorophenyl)piperidin-1-yl]methanone (R)-2,3-Dihydrobenzo[1,4]dioxine-2-carbonyl chloride (46 mg, 0.23 mmol) in DCM (1 ml) was added to a cold solution of 3-(3-fluorophenyl)piperidine HCl (50 mg, 0.23 mmol) and DCM (1 ml). Triethylamine (56 mg, 0.55 mmol) was added and the mixture was stirred for 50 min. After aqueous work-up as described for intermediate A1, the crude mixture was purified by flash chromatography using heptane/EtOAc as eluent. The first eluting diastereomer was collected to give 29 mg of A3.
$^1$H NMR (CDCl$_3$): δ 1.61-2.00 (m, 2H), 2.06-2.17 (m, 1H), 2.58-2.82 (m, 2H), 3.04-3.12 (m, 0.7H), 3.18-3.28 (t, 0.3H), 4.10-4.25 (m, 2H), 4.27-4.39 (m, 1H), 4.46-4.54 (m, 1H), 4.65-4.76 (m, 1H), 4.84-4.90 (m, 1H) 6.80-7.06 (m, 7H), 7.26-7.33 (m, 1H).
The second eluting diastereomer was collected to afford 19 mg of A4.
$^1$H NMR (CDCl$_3$): δ 1.59-1.81 (m, 2H), 1.86-1.96 (m, 1H), 2.08-2.20 (m, 1H), 2.61-3.30 (m, 3H), 4.14-4.25 (m, 1H), 4.30-4.41 (m, 1H), 4.48-4.57 (m, 1H), 4.65-4.72 (m, 1H), 4.77-4.83 (m, 0.7H), 4.86-4.90 (m, 0.3H), 6.80-7.09 (m, 7H), 7.26-7.34 (m, 1H).

Intermediate A5: (R)-2,3-Dihydrobenzo[1,4]dioxin-2-yl-[(R*)-3-(4-fluorophenyl)piperidin-1-yl]methanone Intermediate A6: (R)-2,3-Dihydrobenzo[1,4]dioxin-2-yl-[(S*)-3-(4-fluorophenyl)piperidin-1-yl]methanone (R)-2,3-Dihydrobenzo[1,4]dioxine-2-carbonyl chloride (46 mg, 0.23 mmol) in DCM (1 ml) was added to a cold solution of 3-(4-fluorophenyl)piperidine.HCl (50 mg, 0.23 mmol) and DCM (1 ml). Triethylamine (56 mg, 0.55 mmol) was added and the mixture was stirred for 50 min. After aqueous work-up as described for intermediate A1, the crude mixture was purified by flash chromatography using heptane/EtOAc as eluent. Again, the first eluting diastereomer was collected to give 37 mg of A5.
$^1$H NMR (CDCl$_3$): δ 1.60-2.00 (m, 3H), 2.04-2.16 (m, 1H), 2.56-2.81 (m, 2H), 3.05-3.15 (m, 0.6H), 3.20 (t, 0.4H), 4.13-4.24 (m, 1H), 4.28-4.40 (m, 1H), 4.47-4.55 (m, 1H), 4.65-4.74 (m, 1H), 4.84-4.89 (m, 1H) 6.70-6.95 (m, 4H), 6.98-7.05 (m, 2H), 7.15-7.24 (m, 2H).
The second eluting diastereomer was collected to afford 20 mg of A6.
$^1$H NMR (CDCl$_3$): δ 1.60-1.76 (m, 1H), 1.78-1.95 (m, 2H), 2.02-2.13 (m, 1H), 2.62-2.71 (m, 0.7H), 2.80 (t, 0.3H), 2.98-3.35 (m, 2H), 4.14-4.25 (m, 1H), 4.29-4.39 (m, 1H), 4.45-4.57 (m, 1H), 4.65-4.74 (m, 1H), 4.76-4.82 (m, 0.7H), 4.86-4.93 (m, 0.3H), 6.81-7.30 (m, 8H).

Intermediate A7: (R)-2,3-Dihydrobenzo[1,4]dioxin-2-yl-[(R*)-3-(3-hydroxyphenyl)piperidin-1-yl]methanone Intermediate A8: (R)-2,3-Dihydrobenzo[1,4]dioxin-2-yl-[(S*)-3-(3-hydroxyphenyl)piperidin-1-yl]methanone A mixture of (R)-2,3 dihydrobenzo[1,4]dioxine-2-carboxylic acid (5.06 g, 28.1 mmol), toluene (25 ml) and thionyl chloride (6.68 ml, 56.2 mmol) was heated to reflux. After 1.5 hours the reaction mixture was cooled down and evaporated to dryness. Toluene was added to the evaporation residue and evaporated to dryness. The evaporation residue in THF (10 ml) was added slowly to a mixture of (R*)-3-(piperidin-3-yl)phenol hydrochloride (5.0 g, 23.4 mmol), potassium carbonate (4.85 g, 35.1 mmol), water (16.5 ml) and THF (33.5 ml). After the addition the reaction mixture was stirred at RT for 10 minutes, layers were separated and organic phase was washed with aq NaCl solution. The organic phase was evaporated to dryness and the evaporation residue was crystallized from ethyl acetate to yield 6.79 g of A7.
$^1$H NMR (CDCl$_3$): δ 1.60-1.97 (m, 3H), 2.05-2.15 (m, 1H), 2.62-2.76 (m, 2H), 3.05-3.27 (m, 1H), 4.15-4.18 (m, 1H), 4.31-4.37 (m, 1H), 4.48-4.52 (m, 1H), 4.66-4.68 (m, 1H), 4.86-4.89 (m, 1H), 5.25 & 5.40 (2×s, 1H), 6.71-6.94 (m, 7H), 7.16-7.20 (m, 1H).
(R)-2,3-Dihydrobenzo[1,4]dioxine-2-carbonyl chloride (475 mg, 2.4 mmol) in DCM (4 ml) was added to a mixture of 3-(piperidin-3-yl)phenol HBr (259 mg, 1.06 mmol), triethylamine (307 mg, 3.01 mmol) and DCM (4 ml). The mixture was stirred for 2 h, after which 1 M HCl (5 ml) was added. The phases were separated and the organic phase was absorbed on silica. The mixture was purified by flash chromatography using heptane/EtOAc as eluent. The fractions containing the second eluting diastereomer were collected. The isolated product (199 mg) was the compound which had been acylated on both the amine and the phenol. The ester bond was hydrolysed by treating the compound with two equivalents of KOH in MeOH (5 ml) for one hour. The mixture was evaporated to dryness, the crude product was taken up in EtOAc (10 ml), washed with 1 M K$_2$CO$_3$, dried and evaporated to dryness to afford 77 mg of A8.
$^1$H NMR (CDCl$_3$): δ 1.59-1.95 (m, 3H), 2.06-2.15 (m, 1H), 2.61-3.30 (m, 3H), 4.13-4.23 (m, 1H), 4.31-4.39 (m, 1H), 4.46-4.55 (m, 1H), 4.65-4.71 (m, 1H), 4.80-4.92 (m, 2H), 6.65-6.98 (m, 7H), 7.15-7.28 (m, 1H).

Intermediate A9: (R)-2,3-Dihydrobenzo[1,4]dioxin-2-yl-[(R*)-3-(3-trifluoromethylphenyl)piperidin-1-yl]-methanone Intermediate A10: (R)-2,3-Dihydrobenzo[1,4]dioxin-2-yl-[(S*)-3-(3-trifluoromethylphenyl)-piperidin-1-yl]methanone (R)-2,3-Dihydrobenzo[1,4]dioxine-2-carbonyl chloride (44 mg, 0.22 mmol) in DCM (1 ml) was added to a mixture of 3-(3-trifluoromethylphenyl)piperidine HCl (50 mg, 0.19 mmol) and DCM (1 ml). Triethylamine (54 mg, 0.53 mmol) was added and the mixture was stirred for 1 h. 1 M HCl (2 ml) was added, and the phases were separated. The organic phase was absorbed on silica and the crude mixture was purified by flash chromatography using heptane/EtOAc as eluent. The fractions containing the first eluting diastereomer were collected to give 30 mg of A9.
$^1$H NMR (CDCl$_3$): δ 1.72-2.00 (m, 3H), 2.06-2.20 (m, 1H), 2.60-2.87 (m, 2H), 3.06-3.16 (m, 0.7H), 3.26 (t, 0.3H), 4.16-4.26 (m, 1H), 4.27-4.40 (m, 1H), 4.46-4.55 (m, 1H), 4.67-4.80 (m, 1H), 4.84-4.91 (m, 1H) 6.79-6.95 (m, 4H), 7.40-7.56 (m, 4H).
The second eluting diastereomer was collected to afford 19 mg of A10.
$^1$H NMR (CDCl$_3$): δ 1.59-1.99 (m, 3H), 2.08-2.19 (m, 1H), 2.61-3.34 (m, 3H), 4.14-4.25 (m, 1H), 4.30-4.41 (m, 1H), 4.48-4.57 (m, 1H), 4.65-4.72 (m, 1H), 4.77-4.83 (m, 0.7H), 4.86-4.90 (m, 0.3H), 6.80-7.09 (m, 7H), 7.26-7.34 (m, 1H).

Intermediate A11: (R)-2,3-Dihydrobenzo[1,4]dioxin-2-yl-[(R*)-3-(4-trifluoromethylphenyl)piperidin-1-yl]-methanone Intermediate A12: (R)-2,3-Dihydrobenzo[1,4]dioxin-2-yl-[(S*)-3-(4-trifluoromethylphenyl)-piperidin-1-yl]methanone (R)-2,3-Dihydrobenzo[1,4]dioxine-2-carbonyl chloride (44 mg, 0.22 mmol) was dissolved in DCM (4 ml). 3-(4-Trifluoromethylphenyl)piperidine HCl (51 mg, 0.19 mmol) and triethylamine were added. The mixture was stirred for 1 h, 1 M HCl (2 ml) was added, and the phases were separated. The organic phase was absorbed on silica and the mixture purified by flash chromatography using heptane/EtOAc as eluent. The fractions containing the first eluting diastereomer were collected to yield 21 mg of A11.

$^1$H NMR (CDCl$_3$): δ 1.64-2.01 (m, 3H), 2.07-2.18 (m, 1H), 2.62-2.75 (m, 1H), 2.77-2.88 (m, 1H), 3.07-3.18 (m, 0.6H), 3.26 (t, 0.4H), 4.16-4.27 (m, 1H), 4.26-4.40 (m, 1H), 4.47-4.58 (m, 1H), 4.67-4.77 (m, 1H), 4.84-4.91 (m, 1H) 6.77-6.99 (m, 4H), 7.32-7.42 (m, 2H), 7.55-7.65 (m, 2H).

The second eluting diastereomer was collected to afford 21 mg of A12.

$^1$H NMR (CDCl$_3$): δ 1.59-1.97 (m, 3H), 2.06-2.19 (m, 1H), 2.59-3.36 (m, 3H), 4.16-4.26 (m, 1H), 4.33-4.40 (m, 1H), 4.46-4.55 (m, 1H), 4.65-4.75 (m, 1H), 4.78-4.83 (m, 0.7H), 4.86-4.93 (m, 0.3H), 6.82-6.94 (m, 4H), 7.27-7.46 (m, 2H), 7.54-7.64 (m, 2H).

Intermediate A13: (R)-2,3-Dihydrobenzo[1,4]dioxin-2-yl-[(R*)-3-(3-methoxyphenyl)piperidin-1-yl]methanone Intermediate A14: (R)-2,3-Dihydrobenzo[1,4]dioxin-2-yl-[(S*)-3-(3-methoxyphenyl)piperidin-1-yl]methanone (R)-2,3-Dihydrobenzo[1,4]dioxine-2-carbonyl chloride (3.04 g, 15.3 mmol) was dissolved in DCM (50 ml). (R*)-3-(3-Methoxyphenyl)piperidine (2.92 g, 15.3 mmol) and triethylamine (1.87 g, 18.36 mmol) were added. After stirring for 40 min, the mixture was washed with water (50 ml), 1 M Na$_2$CO$_3$ (50 ml) and 1 M HCl (50 ml). Drying (Na$_2$SO$_4$) and evaporation gave 5.12 g of A13.

$^1$H NMR (CDCl$_3$): δ 1.58-1.99 (m, 3H), 2.06-2.17 (m, 1H), 2.58-2.82 (m, 2H), 3.05-3.17 (m, 0.6H), 3.20-3.29 (m, 0.4H), 3.80 (s, 3H), 4.15-4.23 (m, 1H), 4.27-4.39 (m, 1H), 4.48-4.52 (m, 1H), 4.65-4.77 (m, 1H), 4.84-4.90 (m, 1H) 6.71-6.96 (m, 7H), 7.23-7.30 (m, 1H).

(R)-2,3-Dihydrobenzo[1,4]dioxine-2-carbonyl chloride (54 mg, 0.27 mmol) was dissolved in DCM (4 ml). 3-(3-Methoxyphenyl)piperidine HCl (72 mg, 0.26 mmol) and triethylamine (59 mg, 0.58 mmol) were added. After stirring for 1 h, acidic work-up as above gave the crude product, which was purified by flash chromatography using heptane/EtOAc as eluent. The second eluting diastereomer was collected to give 19 mg of A14.

$^1$H NMR (CDCl$_3$): δ 1.57-1.99 (m, 3H), 2.08-2.21 (m, 1H), 2.60-3.31 (m, 3H), 3.81 (s, 3H), 4.17-4.25 (m, 1H), 4.31-4.40 (m, 1H), 4.45-4.55 (m, 1H), 4.66-4.75 (m, 1H), 4.77-4.85 (m, 0.7H), 4.86-4.90 (m, 0.3H), 6.78-7.01 (m, 7H), 7.23-7.33 (m, 1H).

Reduction of Intermediates

General Procedure

The intermediate (A1-A14) was dissolved in dry THF (c=0.1-0.5 M). BH$_3$ THF (1 M in THF, 5-7 equivalents) was added and the mixture stirred at 60-90° C. using microwave heating or an oil bath (reaction times from 20 min up to 16 h). The formation of amine-borane-complexes was monitored by TLC or LC-MS. To the ice bath cooled mixture 1 M HCl was added in large excess, and the mixture was stirred at 40-60° C. for 20 min-12 h. The progress of the hydrolysis of the borane-complexes was monitored by TLC or LC-MS. The mixture was placed on an ice-bath, and solid KOH or Na$_2$CO$_3$ was added until the mixture was alkaline. THF was removed by evaporation before or after addition of base. The remaining aqueous phase was extracted with EtOAc or DCM. The organics were pooled, dried (Na$_2$SO$_4$) and evaporated to dryness. The crude product was purified by column chromatography, using a gradient of EtOAc/heptane, with or without 1% triethylamine added, or by crystallisation from a suitable solvent.

Preparation of Compounds of the Invention

Example 1

1-(2,3-Dihydrobenzo[1,4]dioxin-2-ylmethyl)-5-phenyl-1,2,3,6-tetrahydropyridine

A mixture of 2-bromomethyl-2,3-dihydrobenzo[1,4]dioxine (500 mg, 2.18 mmol) and 3-phenyl-pyridine (339 mg, 2.18 mmol) in xylene (2 ml) was refluxed for 4 h. After cooling, the solvent was decanted to give the crude oily pyridinium salt, which was dissolved in MeOH (5 ml). NaBH$_4$ (330 mg, 4 eq) was added in small portions to the cooled mixture. After stirring for 2 h at RT, MeOH was evaporated, water was added and the mixture extracted with EtOAc. Drying (Na$_2$SO$_4$) and evaporation gave the crude product, which was purified by flash chromatography (heptane/EtOAc).

$^1$H NMR (CDCl$_3$): δ 2.36 (m, 1H), 2.66-2.92 (m, 4H), 3.40-3.55 (m, 2H), 4.04 (m, 1H), 4.30-4.45 (m, 2H), 6.13 (m, 1H), 6.80-6.95 (m, 4H), 7.20-7.35 (m, 5H).

Example 2

1-(2,3-Dihydrobenzo[1,4]dioxin-2-ylmethyl)-3-phenylpiperidine

The procedure above was repeated except that the crude pyridium salt was hydrogenated in MeOH under normal pressure (6.5 h, RT) using PtO$_2$ as catalyst. After alkaline work-up the crude product was purified by flash chromatography (heptane/EtOAc).

$^1$H NMR (CDCl$_3$): δ 1.40-1.51 (m, 1H), 1.60-1.85 (m, 2H), 2.11 (br d, 1H), 2.05-2.28 (m, 2H), 2.58 (ddd, 1H), 2.66-2.75 (m, 1H), 2.78-3.10 (m, 3H), 3.92-4.05 (m, 1H), 4.25-4.37 (m, 2H), 6.77-6.90 (m, 4H), 7.15-7.32 (m, 5H).

Example 3

1-(2,3-Dihydrobenzo[1,4]dioxin-2-ylmethyl)-3-(2-methoxyphenyl)piperidine

A mixture of 2-bromomethyl-2,3-dihydrobenzo[1,4]dioxine (34 mg, 0.15 mmol), 3-(2-methoxyphenyl)piperidine HCl (38 mg, 0.165 mmol) and triethylamine (41 mg, 0.39 mmol)

in acetonitrile (2 mL) was heated in a microwave reactor at 110-150° C. for 90 min. After evaporation to dryness, the crude product was purified by flash chromatography using a gradient of heptane and EtOAc as eluent to give 12 mg of the title compound.

$^1$H NMR (CDCl$_3$): δ 1.40-1.53 (m, 1H), 1.71-1.81 (m, 2H), 1.82-1.90 (m, 1H), 2.06-2.18 (m, 2H), 2.54-2.65 (m, 1H), 2.67-2.75 (m, 1H), 2.90-3.02 (m, 1H), 3.02-3.09 (m, 1H), 3.21-3.33 (m, 1H), 3.80 (s, 3H), 3.96-4.04 (m, 1H), 4.26-4.38 (m, 2H), 6.80-6.95 (m, 6H), 7.16-7.23 (m, 2H).

Example 4

3-(4-Chlorophenyl)-1-(2,3-dihydrobenzo[1,4]dioxin-2-ylmethyl)piperidine

A mixture of 2-bromomethyl-2,3-dihydrobenzo[1,4]dioxine (34 mg, 0.15 mmol), 3-(4-chloro-phenyl)piperidine (38 mg, 0.165 mmol) and triethylamine (38 mg, 0.38 mmol) in acetonitrile (2 ml) was heated in a microwave reactor at 110-150° C. for 290 min. After evaporation to dryness, the crude product was purified by flash chromatography using a gradient of heptane and EtOAc as eluent to give 36 mg of the title compound.

$^1$H NMR (CDCl$_3$): δ 1.35-1.48 (m, 1H), 1.63-1.83 (m, 2H), 1.86-1.94 (m, 1H), 2.06-2.24 (m, 2H), 2.53-2.65 (m, 1H), 2.66-2.75 (m, 1H), 2.77-2.86 (m, 1H), 2.90-2.97 (m, 1H), 2.99-3.08 (m, 1H), 3.95-4.03 (m, 1H), 4.26-4.37 (m, 2H), 6.78-6.91 (m, 4H), 7.13-7.20 (m, 2H), 7.23-7.30 (m, 2H).

Example 5

1-(2,3-Dihydrobenzo[1,4]dioxin-2-ylmethyl)-3-(3-methoxyphenyl)piperidine

A mixture of 2-bromomethyl-2,3-dihydrobenzo[1,4]dioxine (36 mg, 0.16 mmol), 3-(3-methoxyphenyl)piperidine HCl (36 mg, 0.16 mmol) and triethylamine (40 mg, 0.39 mmol) in acetonitrile (2 mL) was heated in a microwave reactor at 140-150° C. for 300 min. After evaporation to dryness, the crude product was purified by flash chromatography using a gradient of heptane and EtOAc as eluent to give 17 mg of the title compound.

$^1$H NMR (CDCl$_3$): δ 1.39-1.51 (m, 1H), 1.67-1.83 (m, 2H), 1.89-1.96 (m, 1H), 2.07-2.25 (m, 2H), 2.53-2.64 (m, 1H), 2.68-2.75 (m, 1H), 2.76-2.87 (m, 1H), 2.91-3.02 (m, 1H), 3.03-3.09 (m, 1H), 3.80 (s, 3H), 3.95-4.04 (m, 1H), 4.28-4.38 (m, 2H), 6.74-6.90 (m, 7H), 7.22 (t, 1H).

Example 6

1-(2,3-Dihydrobenzo[1,4]dioxin-2-ylmethyl)-3-p-tolylpiperidine

A mixture of 2-bromomethyl-2,3-dihydrobenzo[1,4]dioxine (36 mg, 0.16 mmol), 3-(4-methylphenyl)piperidine.HCl (35 mg, 0.16 mmol) and triethylamine (38 mg, 0.38 mmol) in acetonitrile (2 mL) was heated in a microwave reactor at 140-150° C. for 9 h. The mixture was absorbed on silica and purified by flash chromatography using a gradient of heptane and EtOAc as eluent to give 20 mg of the title compound.

$^1$H NMR (CDCl$_3$): δ 1.38-1.50 (m, 1H), 1.65-1.83 (m, 2H), 1.86-1.96 (m, 1H), 2.06-2.23, (m, 2H), 2.32 (s, 3H), 2.53-2.63 (m, 1H), 2.67-2.75 (m, 1H), 2.75-2.85 (m, 1H), 2.91-3.00 (m, 1H), 3.01-3.09 (m, 1H), 3.95-4.03 (m, 1H), 4.27-4.37 (m, 2H), 6.79-6.90 (m, 4H), 7.09-7.15 (m, 4H).

Example 7

1-(2,3-Dihydrobenzo[1,4]dioxin-2-ylmethyl)-3-(4-methoxyphenyl)piperidine

A mixture of 2-bromomethyl-2,3-dihydrobenzo[1,4]dioxine (35 mg, 0.15 mmol), 3-(4-methoxyphenyl)piperidine.HCl (38 mg, 0.17 mmol) and triethylamine (41 mg, 0.39 mmol) in acetonitrile (2 mL) was heated in a microwave reactor at 160° C. for 3 h. The mixture was absorbed on silica and purified by flash chromatography using a gradient of heptane and EtOAc as eluent to give 18 mg of the title compound.

$^1$H NMR (CDCl$_3$): δ 1.33-1.45 (m, 1H), 1.62-1.82 (m, 2H), 1.83-1.94 (m, 1H), 2.05-2.20 (m, 2H), 2.51-2.65 (m, 1H), 2.66-2.82 (m, 2H), 2.90-2.99 (m, 1H), 2.99-3.09 (m, 1H), 3.78 (s, 3H), 3.93-4.03 (m, 1H), 4.26-4.38 (m, 2H), 6.80-6.93 (m, 6H), 7.10-7.20 (m, 2H).

Example 8

1-(2,3-Dihydrobenzo[1,4]dioxin-2-ylmethyl)-3-o-tolylpiperidine

A mixture of 2-bromomethyl-2,3-dihydrobenzo[1,4]dioxine (35 mg, 0.15 mmol), 3-(2-methylphenyl)piperidine.HCl (35 mg, 0.16 mmol) and triethylamine (38 mg, 0.38 mmol) in acetonitrile (2 mL) was heated in a microwave reactor at 140-150° C. for 12.5 h. The mixture was absorbed on silica and purified by flash chromatography using a gradient of heptane and EtOAc as eluent to give 29 mg of the title compound.

$^1$H NMR (CDCl$_3$): δ 1.40-1.53 (m, 1H), 1.72-1.90 (m, 3H), 2.10-2.27 (m, 2H), 2.36 (s, 3H), 2.53-2.65 (m, 1H), 2.69-2.76 (m, 1H), 2.90-3.11 (m, 3H), 3.95-4.03 (m, 1H), 4.28-4.37 (m, 2H), 6.80-6.91 (m, 4H), 7.08-7.24 (m, 4H).

Example 9

4-[1-(2,3-Dihydrobenzo[1,4]dioxin-2-ylmethyl)piperidin-3-yl]phenol

A mixture of 2-bromomethyl-2,3-dihydrobenzo[1,4]dioxine (47 mg, 0.20 mmol), 4-(piperidin-3-yl)phenol.HBr (53 mg, 0.20 mmol) and KHCO$_3$ (84 mg, 0.84 mmol) in acetonitrile (2 mL) was heated in a microwave reactor at 160° C. for 6.5 h. The mixture was absorbed on silica and purified by flash chromatography using a gradient of DCM and MeOH as eluent to give 6 mg of the title compound.

$^1$H NMR (CD$_3$OD): δ 1.38-1.45 (m, 1H), 1.67-1.90 (m, 3H), 2.07-2.21 (m, 2H), 2.56-2.79 (m, 3H), 2.93-3.14 (m, 2H), 3.89-3.96 (m, 1H), 4.24-4.29 (m, 1H), 4.39-4.39 (m, 1H), 6.68-6.73 (m, 2H), 6.76-6.84 (m, 4H), 7.01-7.08 (m, 2H).

Example 10

1-(2,3-Dihydrobenzo[1,4]dioxin-2-ylmethyl)-3-(3-fluorophenyl)piperidine

A mixture of 2-bromomethyl-2,3-dihydrobenzo[1,4]dioxine (340 mg, 0.48 mmol), 3-(3-fluorophenyl)piperidine (323 mg, 2.50 mmol) and triethylamine (455 mg, 4.50 mmol) in acetonitrile (3 mL) was heated in a microwave reactor at 140° C. for 60 min. The mixture was absorbed on silica and purified by flash chromatography using a gradient of heptane and EtOAc as eluent to give 213 mg of the title compound.

¹H NMR (CDCl₃): δ 1.35-1.50 (m, 1H), 1.64-1.83 (m, 2H), 1.88-1.97 (m, 1H), 2.08-2.25 (m, 2H), 2.53-2.65 (m, 1H), 2.67-2.75 (m, 1H), 2.79-2.89 (m, 1H), 2.89-2.99 (m, 1H), 2.99-3.09 (m, 1H), 3.95-4.04 (m, 1H), 4.28-4.38 (m, 2H), 6.80-6.98 (m, 6H), 6.97-7.01 (m, 7H), 7.21-7.29 (m, 1H).

Example 11

3-[1-(2,3-Dihydrobenzo[1,4]dioxin-2-ylmethyl)piperidin-3-yl]phenol

A mixture of 2-bromomethyl-2,3-dihydrobenzo[1,4]dioxine (54 mg, 0.24 mmol), 3-(piperidin-3-yl)phenol.HBr (60 mg, 0.23 mmol) and KHCO₃ (84 mg, 0.84 mmol) in acetonitrile (2 mL) was heated in a microwave reactor at 160° C. for 5.5 h. The mixture was absorbed on silica and purified by flash chromatography using a gradient of DCM and MeOH (1% triethylamine) as eluent to give 74 mg of the title compound.
¹H NMR (CDCl₃): δ 1.38-1.53 (m, 1H), 1.68-1.84 (m, 2H), 1.87-1.97 (m, 1H), 2.06-2.24 (m, 2H), 2.53-2.65 (m, 1H), 2.66-2.75 (m, 1H), 2.77-2.86 (m, 1H), 2.90-2.97 (m, 1H), 2.99-3.08 (m, 1H), 3.95-4.03 (m, 1H), 4.26-4.37 (m, 2H), 6.78-6.91 (m, 4H), 7.13-7.20 (m, 2H), 7.23-7.30 (m, 2H).

Example 12

2-[1-(2,3-Dihydrobenzo[1,4]dioxin-2-ylmethyl)piperidin-3-yl]phenol

A mixture of 2-bromomethyl-2,3-dihydrobenzo[1,4]dioxine (54 mg, 0.24 mmol), 2-(piperidin-3-yl)phenol.HBr (61 mg, 0.24 mmol) and KHCO₃ (84 mg, 0.84 mmol) in acetonitrile (2 mL) was heated in a microwave reactor at 160° C. for 5.5 h. The mixture was absorbed on silica and purified by flash chromatography using a gradient of DCM and MeOH (1% triethylamine) as eluent to give 11 mg of the title compound.
¹H NMR (CDCl₃): δ 1.51-1.63 (m, 1H), 1.69-1.87 (m, 3H), 2.20-2.41 (m, 2H), 2.57-2.75 (m, 2H), 2.86-3.14 (m, 2H), 2.66-2.75 (m, 1H), 3.22-3.31 (m, 1H), 3.88-3.95 (m, 1H), 4.24-4.30 (m, 1H), 4.31-4.39 (m, 1H) 6.78-6.91 (m, 4H), 7.13-7.20 (m, 2H), 7.23-7.30 (m, 2H).

Example 13

(R*)-1-[(S)—(2,3-Dihydrobenzo[1,4]dioxin-2-yl)methyl]-3-(2-fluorophenyl)piperidine (R)-2,3-Dihydrobenzo[1,4]dioxin-2-yl-[(R*)-3-(2-fluorophenyl)piperidin-1-yl]methanone (10 mg, 0.0035 mmol) was treated with BH₃ THF according to the above general procedure. Flash chromatography gave 2.7 mg of the title compound.
¹H NMR (CDCl₃): δ 1.45-1.57 (m, 1H), 1.73-1.81 (m, 2H), 1.87-1.94 (m, 1H), 2.18-2.29 (m, 2H), 2.59-2.68 (m, 1H), 2.68-2.75 (m, 1H), 2.76-2.85 (m, 1H), 2.91-2.98 (m, 1H), 3.00-3.09 (m, 1H), 3.97-4.06 (m, 1H), 4.28-4.37 (m, 2H), 6.79-6.80 (m, 4H), 6.97-7.05 (m, 1H), 7.06-7.12 (m, 1H), 7.15-7.23 (m, 1H), 7.23-7.33 (m, 1H).

Example 14

(S*)-1-[(S)-1-(2,3-Dihydrobenzo[1,4]dioxin-2-yl)methyl]-3-(2-fluorophenyl)piperidine (R)-2,3-Dihydrobenzo[1,4]dioxin-2-yl-[(S*)-3-(2-fluorophenyl)piperidin-1-yl]methanone (25 mg, 0.073 mmol) was treated with BH₃ THF according to the above general procedure. Flash chromatography gave 18 mg of the title compound.
¹H NMR (CDCl₃): δ 1.44-1.57 (m, 1H), 1.61-1.82 (m, 2H), 1.84-1.94 (m, 1H), 2.11-2.17 (m, 1H), 2.22-2.32 (m, 1H), 2.55-2.61 (m, 1H), 2.68-2.76 (m, 1H), 2.92-2.98 (m, 1H), 3.01-3.08 (m, 1H), 3.14-3.24 (m, 1H), 3.96-4.06 (m, 1H), 4.28-4.38 (m, 2H), 6.79-6.92 (m, 4H), 6.98-7.30 (m, 4H).

Example 15

(R*)-1-[(S)-1-(2,3-Dihydrobenzo[1,4]dioxin-2-yl)methyl]-3-(3-fluorophenyl)piperidine (R)-2,3-Dihydrobenzo[1,4]dioxin-2-yl-[(R*)-3-(3-fluorophenyl)piperidin-1-yl]methanone (1.21 g, 3.51 mmol) was treated with BH₃ THF according to the above general procedure. 1.28 g crude product was obtained.
¹H NMR (CDCl₃): δ 1.45-1.57 (m, 1H), 1.73-1.81 (m, 2H), 1.87-1.94 (m, 1H), 2.18-2.29 (m, 2H), 2.59-2.68 (m, 1H), 2.68-2.75 (m, 1H), 2.76-2.85 (m, 1H), 2.91-2.98 (m, 1H), 3.00-3.09 (m, 1H), 3.97-4.06 (m, 1H), 4.28-4.37 (m, 2H), 6.79-6.80 (m, 4H), 6.97-7.05 (m, 1H), 7.06-7.12 (m, 1H), 7.15-7.23 (m, 1H), 7.23-7.33 (m, 1H).

Example 16

(R*)-1-[(S)-1-(2,3-Dihydrobenzo[1,4]dioxin-2-yl)methyl]-3-(3-fluorophenyl)piperidine.HCl (R*)-1-[(S)-1-(2,3-Dihydrobenzo[1,4]dioxin-2-yl)methyl]-3-(3-fluorophenyl)piperidine (1.28 g, 3.91 mmol) was treated with large excess of 8% HCl/EtOAC and evaporated to dryness. The crude salt was dissolved in boiling EtOAC/IPA. A precipitate was formed upon cooling. Filtration gave 657 mg of the title compound.
¹H NMR (CDCl₃): δ 1.45-1.57 (m, 1H), 1.73-1.81 (m, 2H), 1.87-1.94 (m, 1H), 2.18-2.29 (m, 2H), 2.59-2.68 (m, 1H), 2.68-2.75 (m, 1H), 2.76-2.85 (m, 1H), 2.91-2.98 (m, 1H), 3.00-3.09 (m, 1H), 3.97-4.06 (m, 1H), 4.28-4.37 (m, 2H), 6.79-6.80 (m, 4H), 6.97-7.05 (m, 1H), 7.06-7.12 (m, 1H), 7.15-7.23 (m, 1H), 7.23-7.33 (m, 1H).

Example 17

(S*)-1-[(S)-1-(2,3-Dihydrobenzo[1,4]dioxin-2-yl)methyl]-3-(3-fluorophenyl)piperidine (R)-2,3-Dihydrobenzo[1,4]dioxin-2-yl-[(S*)-3-(3-fluorophenyl)piperidin-1-yl]methanone (19 mg, 0.056 mmol) was treated with BH₃ THF according to the above general procedure. Flash chromatography gave 11 mg of the title compound.
¹H NMR (CDCl₃): δ 1.38-1.49 (m, 1H), 1.65-1.82 (m, 2H), 1.88-1.97 (m, 1H), 2.07-2.25 (m, 2H), 2.53-2.63 (m, 1H), 2.67-2.76 (m, 1H), 2.80-2.90 (m, 1H), 2.92-3.10 (m, 2H), 3.94-4.04 (m, 1H), 4.27-4.40 (m, 2H), 6.76-7.04 (m, 7H), 7.20-7.30 (m, 1H).

Example 18

(R*)-1-[(S)-1-(2,3-Dihydrobenzo[1,4]dioxin-2-yl)methyl]-3-(4-fluorophenyl)piperidine (R)-2,3-Dihydrobenzo[1,4]dioxin-2-yl-[(R*)-3-(4-fluorophenyl)piperidin-1-yl]methanone (20 mg, 0.058 mmol)

was treated with BH₃ THF according to the above general procedure. Flash chromatography gave 16 mg of the title compound.

¹H NMR (CDCl₃): δ 1.35-1.48 (m, 1H), 1.64-1.82 (m, 2H), 1.86-1.94 (m, 1H), 2.07-2.24 (m, 2H), 2.57-2.65 (m, 1H), 2.66-2.75 (m, 1H), 2.76-2.85 (m, 1H), 2.91-2.98 (m, 1H), 3.00-3.09 (m, 1H), 3.95-4.08 (m, 1H), 4.28-4.38 (m, 2H), 6.80-6.89 (m, 4H), 6.94-7.03 (m, 2H), 7.16-7.23 (m, 2H).

Example 19

(S*)-1-[(S)-1-(2,3-Dihydrobenzo[1,4]dioxin-2-yl) methyl]-3-(4-fluorophenyl)piperidine (R)-2,3-Dihydrobenzo[1,4]dioxin-2-yl-[(S*)-3-(4-fluorophenyl)piperidin-1-yl]methanone (20 mg, 0.058 mmol) was treated with BH₃ THF according to the above general procedure. Flash chromatography gave the title compound.

¹H NMR (CDCl₃): δ 1.35-1.43 (m, 1H), 1.65-2.23 (m, 3H), 2.05-2.22 (m, 2H), 2.53-2.62 (m, 1H), 2.67-2.75 (m, 1H), 2.77-2.88 (m, 1H), 2.92-3.00 (m, 1H), 3.00-3.10 (m, 1H), 3.93-4.03 (m, 1H), 4.28-4.40 (m, 2H), 6.81-6.92 (m, 4H), 6.95-7.03 (m, 2H), 7.15-7.24 (m, 2H).

Example 20

(R*)-1-[(S)-1-(2,3-Dihydrobenzo[1,4]dioxin-2-yl) methyl]-3-(3-trifluoromethyl-phenyl)piperidine (R)-2,3-Dihydrobenzo[1,4]dioxin-2-yl-[(R*)-3-(3-trifluoromethylphenyl)piperidin-1-yl]methanone (30 mg, 0.077 mmol) was treated with BH₃ THF according to the above general procedure. Flash chromatography gave 16 mg of the title compound.

¹H NMR (CDCl₃): δ 1.40-1.55 (m, 1H), 1.65-1.85 (m, 2H), 1.89-1.99 (m, 1H), 2.15-2.28 (m, 2H), 2.59-2.64 (m, 1H), 2.70-2.77 (m, 1H), 2.84-2.99 (m, 2H), 3.03-3.12 (m, 1H), 3.98-4.04 (m, 1H), 4.29-4.38 (m, 2H), 6.78-6.90 (m, 4H), 7.38-7.54 (m, 4H).

Example 21

(S*)-1-[(S)-1-(2,3-Dihydrobenzo[1,4]dioxin-2-yl) methyl]-3-(3-trifluoromethyl-phenyl)piperidine (R)-2,3-Dihydrobenzo[1,4]dioxin-2-yl-[(S*)-3-(3-trifluoromethylphenyl)piperidin-1-yl]methanone (29 mg, 0.074 mmol) was treated with BH₃ THF according to the above general procedure. Flash chromatography gave 15 mg of the title compound.

¹H NMR (CDCl₃): δ 1.40-1.55 (m, 1H), 1.61-1.87 (m, 2H), 1.87-1.99 (m, 1H), 2.09-2.30 (m, 2H), 2.52-2.64 (m, 1H), 2.66-2.77 (m, 1H), 2.84-3.12 (m, 3H), 3.94-4.07 (m, 1H), 4.24-4.41 (m, 2H), 6.78-6.96 (m, 4H), 7.36-7.53 (m, 4H).

Example 22

(R*)-1-[(S)-1-(2,3-Dihydrobenzo[1,4]dioxin-2-yl) methyl]-3-(4-trifluoromethylphenyl)piperidine (R)-2,3-Dihydrobenzo[1,4]dioxin-2-yl-[(R*)-3-(4-trifluoromethylphenyl)piperidin-1-yl]methanone (18 mg, 0.046 mmol) was treated with BH₃ THF according to the above general procedure. Flash chromatography gave 7.6 mg of the title compound.

¹H NMR (CDCl₃): δ 1.40-1.52 (m, 1H), 1.68-1.84 (m, 2H), 1.80-1.98 (m, 1H), 2.15-2.27 (m, 2H), 2.59-2.65 (m, 1H), 2.67-2.76 (m, 1H), 2.86-3.00 (m, 2H), 3.01-2.15 (m, 1H), 3.95-4.01 (m, 1H), 4.29-4.37 (m, 2H), 6.78-6.93 (m, 4H), 7.31-7.39 (m, 2H), 7.51-7.59 (m, 2H).

Example 23

(S*)-1-[(S)-1-(2,3-Dihydrobenzo[1,4]dioxin-2-yl) methyl]-3-(4-trifluoromethylphenyl)piperidine (R)-2,3-Dihydrobenzo[1,4]dioxin-2-yl-[(S*)-3-(4-trifluoromethylphenyl)piperidin-1-yl]methanone (13 mg, 0.033 mmol) was treated with BH₃ THF according to the above general procedure. Flash chromatography gave 6 mg of the title compound.

¹H NMR (CDCl₃): δ 1.39-1.53 (m, 1H), 1.65-1.86 (m, 2H), 1.88-1.97 (m, 1H), 2.09-2.29 (m, 2H), 2.55-2.64 (m, 1H), 2.68-2.77 (m, 1H), 2.84-3.11 (m, 3H), 3.95-4.05 (m, 1H), 4.27-4.38 (m, 2H), 6.78-6.95 (m, 4H), 7.31-7.38 (m, 2H), 7.51-7.61 (m, 2H).

Example 24

(R*)-1-[(S)-1-(2,3-Dihydrobenzo[1,4]dioxin-2-yl) methyl]-3-(3-methoxyphenyl)piperidine (R)-2,3-Dihydrobenzo[1,4]dioxin-2-yl-[(R*)-3-(3-methoxyphenyl)piperidin-1-yl]-methanone (21 mg, 0.059 mmol) was treated with BH₃ THF according to the above general procedure. Flash chromatography gave 7.0 mg of the title compound.

¹H NMR (CDCl₃): δ 1.40-1.51 (m, 1H), 1.69-1.82 (m, 2H), 1.89-1.96 (m, 1H), 2.15-2.23 (m, 2H), 2.56-2.64 (m, 1H), 2.67-2.75 (m, 1H), 2.75-2.85 (m, 1H), 2.91-2.84 (m, 1H), 3.02-3.10 (m, 1H), 3.80 (s, 3H), 3.95-4.01 (m, 1H), 4.28-4.35 (m, 2H), 6.73-6.92 (m, 7H), 7.19-7.25 (m, 1H).

Example 25

(R*)-1-[(S)-1-(2,3-Dihydrobenzo[1,4]dioxin-2-yl) methyl]-3-(3-methoxyphenyl)piperidine.HCl Crude (R*)-1-[(S)-1-(2,3-dihydrobenzo[1,4]dioxin-2-yl) methyl]-3-(3-methoxyphenyl)piperidine (2.5 g) was treated three times with 8% HCl/EtOAc and evaporated to dryness. After crystallisation from hot EtOAc/IPA (10 ml/2.5 ml), 1.24 g of the title compound was obtained as almost white crystals.

¹H NMR (CD₃OD): δ 1.72-1.88 (m, 1H), 1.93-2.22 (m, 3H), 3.04-3.27 (m, 4H), 3.39-3.56 (m, 2H), 3.64-3.79 (m, 2H), 3.99-4.08 (m, 1H), 4.29-4.35 (m, 1H), 4.29-4.40 (m, 1H), 4.75-4.90 (m, 1H), 6.84-6.94 (m, 4H), 7.00-7.17 (m, 3H), 7.34-7.43 (m, 1H).

Example 26

(S*)-1-[(S)-1-(2,3-Dihydrobenzo[1,4]dioxin-2-yl) methyl]-3-(3-methoxyphenyl)piperidine (R)-2,3-Dihydrobenzo[1,4]dioxin-2-yl-[(S*)-3-(3-methoxyphenyl)piperidin-1-yl]-methanone (21 mg, 0.059 mmol) was treated with BH₃ THF according to the above general procedure. Flash chromatography gave 7.0 mg of the title compound.

¹H NMR (CDCl₃): δ 1.38-1.52 (m, 1H), 1.67-1.83 (m, 2H), 1.88-1.97 (m, 1H), 2.06-2.16, (m, 1H), 2.16-2.25 (m, 1H), 2.53-2.61 (m, 1H), 2.69-2.75 (m, 1H), 2.76-2.87 (m, 1H), 2.94-3.01 (m, 2H), 3.80 (s, 3H), 3.93-4.02 (m, 1H), 4.27-4.37 (m, 2H), 6.71-6.90 (m, 7H), 7.18-7.27 (m, 1H).

Example 27

(R*)-3-{1-[(S)-1-(2,3-Dihydrobenzo[1,4]dioxin-2-yl)methyl]piperidin-3-yl}phenol (R)-2,3-Dihydrobenzo[1,4]dioxin-2-yl-[(R*)-3-(3-hydroxyphenyl)piperidin-1-yl]-methanone (17.8 g, 54.7 mmol) was treated with BH$_3$·THF according to the above general procedure. Crystallisation from hot EtOH gave 8.5 g of the title compound as almost white crystals.
$^1$H NMR (CD$_3$OD): δ 1.40-1.54 (m, 1H), 1.71-1.82 (m, 2H), 1.84-1.93 (m, 1H), 2.12-2.23 (m, 2H), 2.59-2.74 (m, 2H), 2.74-2.83 (m, 1H), 2.99-3.14 (m, 1H), 3.92-3.98 (m, 1H), 4.24-4.31 (m, 1H), 4.33-4.39 (m, 1H), 6.59-6.63 (m, 1H), 6.66-6.68 (m, 1H), 6.69-6.74 (m, 1H), 6.76-6.83 (m, 4H), 7.06-7.12 (m, 1H).

Example 28

(R*)-3-{1-[(S)-1-(2,3-Dihydrobenzo[1,4]dioxin-2-yl)methyl]piperidin-3-yl}phenol.HCl (R)-2,3-Dihydrobenzo[1,4]dioxin-2-yl-[(R*)-3-(3-hydroxyphenyl)piperidin-1-yl]-methanone (200 mg, 0.615 mmol) was dissolved in EtOAc (4 ml). 1 M HCl/diethyl ether was added in excess. The precipitate was filtered to give 172 mg of the desired salt.
$^1$H NMR (CDCl$_3$): δ 1.52-1.62 (m, 1H), 1.89-2.11 (m, 2H), 2.35-2.53 (m, 1H), 2.69-2.96, (m, 2H), 3.10-3.21 (m, 1H), 3.35-3.62 (m, 3H), 3.89-4.00 (m, 1H), 4.07-4.15 (m, 1H), 4.20-4.32 (m, 1H), 6.64-6.72 (m, 1H), 6.80-7.01 (m, 7H), 7.12-7.19 (m, 1H), 12.45 (br, 1H).

Example 29

(3-{(R*)-1-[(S)-1-(2,3-Dihydrobenzo[1,4]dioxin-2-yl)methyl]piperidin-3-yl}phenyl)methanol (R*)-3-[1-((R)-2,3-Dihydrobenzo[1,4]dioxine-2-carbonyl)piperidin-3-yl]benzoic acid methyl ester (R)-2,3-Dihydrobenzo[1,4]dioxine-2-carbonyl chloride (240 mg, 1.21 mmol) in DCM (5 ml) was added to an ice-cold mixture of 3-(piperidin-3-yl)benzoic acid methyl ester (267 mg, 1.21 mmol), triethylamine (59 mg, 0.58 mmol) and DCM (10 ml). After stirring for 2 h at RT, the mixture was washed with 1 M HCl (10 ml) and 1 M Na$_2$CO$_3$. The organic phase was dried over Na$_2$SO$_4$ and evaporated to dryness and the residue was purified by flash chromatography using heptane/EtOAc as eluent. The first eluting diastereomer was collected to afford 98 mg of the title compound.
$^1$H NMR (CDCl$_3$): δ 1.72-2.02 (m, 3H), 2.09-2.19 (m, 1H), 2.65-2.89 (m, 2H), 3.07-3.19 (m, 0.6H), 3.24-3.33 (m, 0.4H), 3.92 (s, 3H), 4.16-4.27 (m, 1H), 4.30-4.39 (m, 1H), 4.48-4.54 (m, 1H), 4.68-4.76 (m, 1H), 4.76-4.89 (m, 1H) 6.79-6.99 (m, 4H), 7.38-7.46 (m, 2H), 7.90-7.73 (m, 2H).

(3-{(R*)-1-[(S)-1-(2,3-Dihydrobenzo[1,4]dioxin-2-yl)methyl]piperidin-3-yl}phenyl)methanol ((R*)-3-[1-((R)-2,3-Dihydrobenzo[1,4]dioxine-2-carbonyl)piperidin-3-yl]benzoic acid methyl ester (54 mg, 0.147 mmol) was dissolved in dry THF (4 ml) and cooled to 0° C. LiAlH$_4$ (26 mg, 0.680 mmol) was added and the mixture was stirred at RT for 2 h. Water (1 ml), 1 M NaOH (1 ml) and again water (1 ml) were added slowly. The mixture was filtered through Celite and evaporated. Flash chromatography, using a gradient of heptane/EtOAc, gave 3.5 mg of the title compound.
$^1$H NMR (CDCl$_3$): δ 1.47-1.60 (m, 1H), 1.72-1.85 (m, 2H), 1.89-1.96 (m, 1H), 2.17-2.26 (m, 2H), 2.60-2.74 (m, 2H), 2.59-2.75 (m, 2H), 2.82-2.91 (m, 1H), 4.06-4.14 (m, 1H), 4.25-4.31 (m, 1H), 4.32-4.30 (m, 1H), 4.58 (s, 2H), 6.75-6.85 (m, 4H), 7.13-7.22 (m, 2H), 7.23-7.35 (m, 2H).

Example 30

Acetic acid 3-{(S)-1-[(R*)-1-(2,3-dihydrobenzo[1,4]dioxin-2-yl)methyl]piperidin-3-yl}phenyl ester.HCl Acetyl chloride (58 mg, 0.74 mmol) was added to a solution of (R*)-3-{1-[(S)-1-(2,3-dihydrobenzo-[1,4]dioxin-2-yl)methyl]piperidin-3-yl}phenol (198 mg, 0.608 mmol) and triethylamine (75 mg, 0.74 mmol) in DCM (5 ml). The mixture was stirred for 40 min, washed with water, dried over Na$_2$SO$_4$ and evaporated to dryness. The crude product was treated with excess EtOAc/HCl and evaporated to dryness. Recrystallisation from hot EtOAc/IPA gave 60 mg of the title compound.
$^1$H NMR (CD$_3$OD): δ 1.69-1.85 (m, 1H), 1.91-2.18 (m, 3H), 2.28 (s, 3H), 3.05-3.36 (m, 4H), 3.45-3.60 (m, 1H), 3.64-3.86 (m, 1H), 4.00-4.08 (m, 1H), 4.25-4.42 (m, 1H), 4.71-4.80 (m, 2H), 6.84-6.94 (m, 4H), 7.01-7.10 (m, 2H), 7.18-7.23 (m, 1H), 7.37-7.43 (m, 1H).

Example 31

2-(3-{(R*)-1-[(S)-1-(2,3-Dihydrobenzo[1,4]dioxin-2-yl)methyl]piperidin-3-yl}phenoxy)ethanol (R*)-3-{1-[(S)-1-(2,3-Dihydrobenzo[1,4]dioxin-2-yl)methyl]piperidin-3-yl}phenol (51 mg), K$_2$CO$_3$ (28 mg, 0.20 mmol), 2-chloroethanol and MeCN (2 ml) were heated under microwaves at 80-105° C. for 6 h. The solvent was removed and the residue was taken up in DCM. This solution was washed with water and 1 M NaOH and evaporated to dryness. Flash chromatography (heptane/EtOAc) gave 3 mg of the title compound.
$^1$H NMR (CD$_3$OD): δ 1.44-1.56 (m, 1H), 1.69-1.84 (m, 2H), 1.85-1.94 (m, 1H), 2.14-2.26 (m, 2H), 2.58-2.74 (m, 2H), 2.76-2.87 (m, 1H), 2.98-3.16 (m, 2H), 3.83-3.89 (m, 2H), 3.89-3.97 (m, 2H), 3.99-4.06 (m, 2H), 4.24-4.31 (m, 1H), 4.33-4.39 (m, 1H), 6.76-6.88 (m, 7H), 7.16-7.23 (m, 1H).

Example 32

3-(3-{(R*)-1-[(S)-1-(2,3-Dihydrobenzo[1,4]dioxin-2-yl)methyl]piperidin-3-yl}phenoxy)propan-1-ol (R*)-3-{1-[(S)-1-(2,3-Dihydrobenzo[1,4]dioxin-2-yl)methyl]piperidin-3-yl}phenol (208 mg, 0.64 mmol), K$_2$CO$_3$ (103 mg, 0.74 mmol), 3-bromo-1-propanol (86 mg, 0.62 mmol) and MeCN (5 ml) were heated under microwaves at 105° C. for 6 h. More K$_2$CO$_3$ (103 mg) and 3-bromo-1-propanol (86 mg) were added and the heating was continued for 2 h. The solvent was removed and the residue was taken up in DCM. This solution was washed with water and 1 M NaOH and evaporated to dryness. Flash chromatography (heptane/EtOAc) gave 76 mg of the title compound.

¹H NMR (CD₃OD): δ 1.44-1.56 (m, 1H), 1.64-1.84 (m, 2H), 1.84-1.93 (m, 1H), 1.93-2.00 (m, 2H), 2.15-2.26 (m, 2H), 2.59-2.74 (m, 2H), 2.76-2.86 (m, 1H), 2.98-3.16 (m, 2H), 3.70-3.76 (m, 2H), 3.90-3.97 (m, 1H), 4.02-4.09 (m, 2H), 4.25-4.30 (m, 1H), 4.32-4.38 (m, 1H), 6.72-6.84 (m, 7H), 7.14-7.22 (m, 1H).

Example 33

Trifluoromethanesulfonic acid 3-{(R*)-1-[(S)-1-(2,3-dihydrobenzo[1,4]dioxin-2-yl)methyl]-piperidin-3-yl}phenyl ester (R*)-3-{1-[(S)-1-(2,3-Dihydrobenzo[1,4]dioxin-2-yl)methyl]piperidin-3-yl}phenol (1.77 g, 5.44 mmol) was dissolved in DCM (10 ml) under an inert atmosphere. Triethylamine (0.58 g, 5.71 mmol) was added and the mixture was cooled to −30° C. Trifluoromethanesulfonic acid anhydride (1.61 g, 5.71 mmol) was added dropwise. The cooling bath was removed and the mixture stirred for 1 h. The mixture was washed with water (2×10 ml) and evaporated to dryness. Column chromatography, using a gradient of DCM:MeOH as eluent, gave 1.1 g of the title compound.
¹H NMR (CDCl₃): δ 1.38-1.51 (m, 1H), 1.65-1.84 (m, 2H), 1.89-1.99 (m, 1H), 2.11-2.28 (m, 2H), 2.57-2.64 (m, 1H), 2.68-2.75 (m, 1H), 2.83-3.09 (m, 3H), 3.96-4.03 (m, 1H), 4.26-4.38 (m, 2H), 6.80-6.92 (m, 4H), 7.08-7.18 (m, 2H), 7.25-7.34 (m, 1H), 7.36-7.41 (m, 1H).

Example 34

(3-{(R*)-1-[(S)-1-(2,3-Dihydrobenzo[1,4]dioxin-2-yl)methyl]piperidin-3-yl}phenoxy)acetic acid To a solution of (R*)-3-{1-[(S)-1-(2,3-dihydrobenzo[1,4]dioxin-2-yl)methyl]piperidin-3-yl}phenol (201 mg, 0.62 mmol) in dry DMF (2 ml) was added NaH (60% in oil, 30 mg, 0.75 mmol) under nitrogen atmosphere and the mixture was stirred at 0° C. for 5 min, then allowed to warm to RT and stirred for further 2.5 h. The reaction mixture was cooled to 0° C., ethyl bromoacetate (106 mg, 0.62 mmol) was added and the mixture was stirred at RT overnight. Potassium tert-butoxide (69 mg, 0.61 mmol) was added and the mixture was stirred for 3 h at RT and filtered. The precipitate was dissolved in dry MeOH, the solution filtered and evaporated to dryness to give 170 mg of the title compound.
¹H NMR (DMSO-d₆): δ 1.33-1.46 (m, 1H), 1.52-1.73 (m, 2H), 1.74-1.83 (m, 1H), 2.04-2.17 (m, 2H), 2.56-2.73 (m, 3H), 2.88-2.98 (m, 2H), 3.93-3.99 (m, 1H), 4.06 (s, 2H), 4.27-4.39 (m, 2H), 6.59-6.64 (m, 1H), 6.69-6.88 (m, 6H), 7.11 (t, 1H, J=6.8 Hz).

Example 35

3-{(R*)-1-[(S)-1-(2,3-Dihydrobenzo[1,4]dioxin-2-yl)methyl]-piperidin-3-yl}-benzonitrile A mixture of trifluoromethanesulfonic acid 3-{(R*)-1-[(S)-1-(2,3-dihydrobenzo[1,4]dioxin-2-yl)methyl]-piperidin-3-yl}phenyl ester (51 mg, 0.11 mmol), tributyltin cyanide (142 mg, 0.45 mmol) and tetrakis(triphenylphosphine)palladium (189 mg, 0.164 mmol) in 1,2-dichloroethane (15 ml) was heated in a microwave reactor at 80° C. for 80 h. The solid precipitate was filtered off and the mixture was evaporated to dryness. The residue was redissolved in DCM, filtered and washed two times with 1 M HCl. The combined organic phases were washed with brine, dried (Na₂SO₄) and evaporated to dryness. The crude product was purified by flash chromatography first using gradient of DCM and MeOH and then using gradient of heptane and EtOAc as eluent to give 2.8 mg of the title compound.
¹H NMR (CDCl₃): δ 1.48-1.59 (m, 1H), 1.70-1.84 (m, 2H), 1.89-1.94 (m, 1H), 2.19-2.32 (m, 2H), 2.61-2.75 (m, 2H), 2.89-3.10 (m, 3H), 3.93-3.98 (m, 1H), 4.26-4.35 (m, 1H), 4.35-4.40 (m, 1H), 6.76-6.84 (m, 3H), 7.43-7.60 (m, 5H).

Example 36

3-Benzo[1,3]dioxol-5-yl-1-[(S)-1-(2,3-dihydrobenzo[1,4]dioxin-2-yl)methyl]-piperidine 3-Benzo[1,3]dioxol-5-ylpyridine A mixture of 3,4-(methylenedioxy)phenylboronic acid (500 mg, 3.0 mmol), 3-bromopyridine (290 µl, 476 mg, 3.0 mmol), 2 M Na₂CO₃ (3.05 ml, 6.0 mmol), tetrakis(triphenylphosphine)palladium (35 mg, 0.03 mmol), EtOH (0.75 ml) and toluene (3 ml) was heated in a microwave reactor at 120° C. for 40 min. Another crop of 3,4-(methylenedioxy)phenylboronic acid (250 mg, 1.5 mmol) was added and the mixture heated under microwaves at 120° C. for 10 min. The reaction mixture was filtered and the layers were separated. The organic phase was extracted twice with 1 M HCl. All the aqueous phases were combined, basified with 5 M NaOH and extracted twice with EtOAc. The combined organic phases were dried (Na₂SO₄), filtered and evaporated to give 585 mg of the title compound.
¹H NMR (DMSO-d₆): δ 6.08 (s, 2H), 7.03-7.06 (m, 1H), 7.19-7.24 (m, 1H), 7.33-7.35 (m, 1H), 7.42-7.46 (m, 1H), 7.99-8.03 (m, 1H), 8.52 (dd, 1H, J=1.77, 4.80 Hz), 8.84 (dd, 1H, J=2.65, 0.88 Hz).

3-Benzo[1,3]dioxol-5-ylpiperidine.HCl

3-Benzo[1,3]dioxol-5-ylpyridine (578 mg, 2.9 mmol), PtO₂ hydrate (58 mg), methanol (20 ml) and conc. HCl (2 ml) were charged into the Parr reaction flask and hydrogenated (55 psi) for 4 h. The reaction mixture was filtered and evaporated to dryness. The crude product was crystallized from EtOAc/IPA to give 226 mg of the title compound.
¹H NMR (CD₃OD): δ 1.71-1.91 (m, 2H), 1.96-2.08 (m, 2H), 2.85-2.95 (m, 1H), 2.96-3.06 (m, 2H), 3.32-3.46 (m, 2H), 5.92 (s, 2H), 6.73-6.83 (m, 3H).

(3-Benzo[1,3]dioxol-5-ylpiperidin-1-yl-(R)-2,3-dihydrobenzo[1,4]dioxin-2-ylmethanone A mixture of (R)-2,3-dihydrobenzo[1,4]dioxine-2-carboxylic acid (167 mg, 0.93 mmol), thionyl chloride (338 µl, 551 mg, 4.63 mmol) and dry toluene was heated at 95° C. for 1.5 h and then evaporated to dryness. Toluene was added and the evaporation was repeated. The evaporation residue was dissolved in DCM (2 ml) and added slowly to a cold solution (0° C.) of 3-benzo[1,3]dioxol-5-yl-piperidine HCl (224 mg, 0.93 mmol) and DIPEA (0.324 ml, 240 mg, 1.85 mmol) in DCM (5 ml). The reaction mixture was stirred for 1 h 45 min at RT. Water was added, layers were separated and the organic phase was washed twice with 1 M HCl and sat. NaHCO₃. The organic phase was dried (Na₂SO₄), filtered and evaporated to give 290 mg of the title compound.
¹H NMR (CDCl₃): δ 1.56-1.77 (m, 2H), 1.82-1.97 (m, 1H), 2.03-2.14 (m, 1H), 2.52-2.73 (m, 2H), 2.85-3.25 (m, 1H), 4.10-4.22 (m, 1H), 4.29-4.38 (m, 1H), 4.45-4.55 (m, 1H), 4.63-4.73 (m, 1H), 4.78-4.91 (m, 1H), 5.94 (s, 2H), 6.64-6.97 (m, 7H).

3-Benzo[1,3]dioxol-5-yl-1-[(S)-1-(2,3-dihydrobenzo[1,4]dioxin-2-yl)methyl]-piperidine (3-Benzo[1,3]dioxol-5-ylpiperidin-1-yl-(R)-2,3-dihydrobenzo[1,4]dioxin-2-ylmethanone (285 mg, 0.77 mmol) was dissolved in dry DMF (2.5 ml) and 1 M $BH_3$ THF (3.10 ml, 3.10 mmol) was slowly added under a nitrogen atmosphere. The reaction mixture was stirred for 4.5 h at RT and then cooled to 0° C. Water was slowly added and the mixture basified with 2.5 M NaOH and extracted three times with EtOAc. The combined organic phases were dried ($Na_2SO_4$), filtered and evaporated to dryness. The crude product was dissolved in methanol (25 ml) and 5 M HCl (1.5 ml) was slowly added. The mixture was stirred for 1 h at RT and then at 60° C. for 2 h. The reaction mixture was evaporated to dryness, redissolved in EtOAc and washed twice with 1 M $Na_2CO_3$ and water. The combined organic phases were dried ($Na_2SO_4$), filtered and evaporated to dryness to give 228 mg of the title compound.

$^1$H NMR ($CDCl_3$): δ 1.33-1.46 (m, 1H), 1.63-1.82 (m, 2H), 1.85-1.94 (m, 1H), 2.05-2.21. (m, 2H), 2.53-2.63 (m, 1H), 2.66-2.81 (m, 2H), 2.90-2.98 (m, 1H), 2.98-3.07 (m, 1H), 3.94-4.03 (m, 1H), 4.27-4.36 (m, 2H), 5.92 (s, 2H), 6.66-6.71 (m, 1H), 6.72-6.76 (m, 2H), 6.79-6.90 (m, 4H).

Example 37

3-[(R*)-1-((S)-6-Benzyloxy-2,3-dihydro-benzo[1,4]dioxin-2-ylmethyl)-piperidin-3-yl]-phenol

1-[4-Benzyloxy-2-((R)-1-oxiranylmethoxy)phenyl]ethanone

To a stirred solution of 1-(4-(benzyloxy)-2-hydroxyphenyl)ethanone (3.36 g, 13.9 mmol) in anhydrous DMF (15 ml) was added NaH (0.62 g, 15.5 mmol). The mixture was allowed to stir at RT for 30 min, and a solution of (R)-oxiran-2-ylmethyl 4-methylbenzenesulfonate (3.17 g, 13.9 mmol) in DMF was added dropwise at RT. The mixture was slowly heated to 60° C. and stirred for 3 h. The reaction was quenched by addition of water (80 ml) and extracted three times with EtOAc. The combined organic layers were extracted twice with aq 1 M NaOH and washed with water and brine. The organic layer was dried with $Na_2SO_4$ and concentrated. The crude product obtained was purified by column chromatography with EtOAc/heptane (1:1) as eluent to afford the title compound (2.64 g) as a white solid.

$^1$H NMR ($CDCl_3$): δ 2.63 (s, 3H), 2.76 (m, 1H), 2.94 (t, 1H), 3.39 (m, 1H), 3.96 (dd, 1H), 4.32 (dd, 1H), 5.10 (s, 2H), 6.52 (d, 1H), 6.62 (dd, 1H), 7.34-7.44 (m, 5H), 7.84 (d, 1H).

Acetic acid 4-benzyloxy-2-((R)-1-oxiranylmethoxy)phenyl ester

To a stirred solution of 1-[4-benzyloxy-2-((R)-1-oxiranylmethoxy)phenyl]ethanone (1.62 g, 5.43 mmol) in DCM (60 ml) was added m-chloroperbenzoic acid (2.15 g) and solid $NaHCO_3$ (3.24 g). Stirring was continued at 40° C. for 1 h. The mixture was filtered and the filtrate was washed once with 10% $NaHSO_4$ solution and then twice with $NaHCO_3$ solution. The organic layer was washed with water and brine, dried with $Na_2SO_4$. The solvent was removed under reduced pressure. The crude product obtained (1.34 g) was sufficiently pure for the next step.

$^1$H NMR ($CDCl_3$): δ 2.30 (s, 3H), 2.71 (m, 1H), 2.87 (t, 1H), 3.30 (m, 1H), 3.94 (dd, 1H), 4.21 (dd, 1H), 5.02 (s, 2H), 6.54 (dd, 1H), 6.64 (d, 1H), 6.94 (d, 1H), 7.33-7.42 (m, 5H).

((S)-6-Benzyloxy-2,3-dihydrobenzo[1,4]dioxin-2-yl)methanol

To a stirred solution of acetic acid 4-benzyloxy-2-((R)-1-oxiranylmethoxy)phenyl ester (1.34 g, 4.26 mmol) in THF (30 ml), was added aq 2 M NaOH (2.45 ml). The mixture was stirred overnight at RT, THF was removed under reduced pressure and water (50 ml) was added. The water solution was then extracted three times with EtOAc and the combined extracts washed with water and brine. The organic layer was dried ($Na_2SO_4$), and evaporated in vacuo. The crude product (1.07 g) was used without purification.

$^1$H NMR ($CDCl_3$): δ 1.96 (br s, 1H), 3.80-3.91 (m, 2H), 4.08 (m, 1H), 4.11 (m, 1H), 4.27 (dd, 1H), 4.99 (s, 2H), 6.50-6.54 (m, 2H), 6.80 (d, 1H), 7.30-7.42 (m, 5H).

Methanesulfonic acid (R)-6-benzyloxy-2,3-dihydrobenzo[1,4]dioxin-2-ylmethyl ester To a stirred solution of crude ((S)-6-benzyloxy-2,3-dihydrobenzo[1,4]dioxin-2-yl)methanol (1.65 g, 6.06 mmol) in dry DCM (10 ml), was added triethylamine (0.88 ml). The mixture was cooled to 0° C. and methanesulfonyl chloride (0.49 ml) was added slowly dropwise to reaction mixture. The mixture was stirred at RT for 1 h and then 10 ml of aq 1 M HCl was added. The mixture was extracted twice with DCM. The combined organic layers were washed with water and brine, dried with $Na_2SO_4$. The solvents were removed under reduced pressure and the crude product (2.22 g) was crystallized from IPA (15 ml), which gave a white solid (1.50 g).

$^1$H NMR ($CDCl_3$): δ 3.08 (s, 3H), 4.11 (m, 1H), 4.28 (d, 1H), 4.42 (s, 3H), 4.98 (s, 2H), 6.51-6.55 (m, 2H), 6.79 (d, 1H), 7.31-7.42 (m, 5H).

3-[(R*)-1-((S)-6-Benzyloxy-2,3-dihydro-benzo[1,4]dioxin-2-ylmethyl)-piperidin-3-yl]-phenol To a solution of methanesulfonic acid (R)-6-benzyloxy-2,3-dihydrobenzo[1,4]dioxin-2-ylmethyl ester (129 mg, 0.368 mmol) and (R*)-3-(piperidin-3-yl)phenol.HBr (100 mg, 0.387 mmol) in acetonitrile was added solid KI (40 mg) and $NaHCO_3$ (98 mg 1.162 mmol). The mixture was heated under microwave irradiation at 150° C. for 1 h. Solid material was filtered and the solvent was evaporated under reduced pressure. The residue was dissolved to DCM and washed twice with water and brine. The organic phase was dried ($Na_2SO_4$), and evaporated in vacuo. The residue was purified by flash column chromatography (EtOAc/heptane) to give the desired product (66.2 mg).

$^1$H NMR ($CDCl_3$): δ 1.42-1.49 (m, 1H), 1.74-1.77 (m, 2H), 1.91 (d, 1H), 2.14-2.20 (m, 2H), 2.59 (dd, 1H), 2.68-2.73 (dd, 1H), 2.79-2.85 (m, 1H), 2.97 (d, 1H), 3.13 (d, 1H), 3.96 (dd, 1H), 4.24-4.29 (m, 2H), 4.96 (s, 2H), 6.46 (dd, 1H), 6.53 (d, 1H), 6.66-6.80 (m, 4H), 6.75 (1H, m), 7.17 (t, 1H), 7.30-7.42 (m, 5H).

Example 38

(S)-2-[(R*)-3-(3-Hydroxy-phenyl)-piperidin-1-ylmethyl]-2,3-dihydro-benzo[1,4]dioxin-6-ol To a solution of 10% Pd/C (33 mg) in EtOAc (10 ml) was added 3-[(R*)-1-((S)-6-benzyloxy-2,3-dihydro-benzo[1,4]

dioxin-2-ylmethyl)-piperidin-3-yl]-phenol (66 mg, 0.125 mmol). The mixture was stirred under hydrogen for 3 h at normal pressure. The mixture was then filtered and evaporated to give an oil. After trituration with diethyl ether the title compound was obtained as a white solid (40 mg).

$^1$H NMR (DMSO-d$_6$): δ 1.30-1.40 (m, 1H), 1.53-1.69 (m, 2H), 1.78 (d, 1H), 2.04-2.11 (m, 2H), 2.56 (m, 2H), 2.61-2.67 (m, 1H), 2.90 (dd, 2H), 3.89 (dd, 1H), 4.21-4.26 (m, 2H), 6.20-6.25 (m, 2H), 6.57-6.68 (m, 4H), 7.06 (t, 1H), 8.90 (s, 1H), 9.21 (s, 1H).

Example 39

3-[(R*)-1-((S)-7-Benzyloxy-2,3-dihydro-benzo[1,4]dioxin-2-ylmethyl)-piperidin-3-yl]-phenol 1-[5-Benzyloxy-2-((R)-1-oxiranylmethoxy)phenyl]ethanone To a stirred solution of 1-(5-benzyloxy-2-hydroxyphenyl)ethanone (3.0 g, 12.4 mmol) in anhydrous DMF (15 ml) was added NaH (0.55 g, 13.6 mmol). The mixture was allowed to stir at RT for 30 min and then heated to 60° C. A solution of (R)-oxiran-2-ylmethyl 4-methylbenzenesulfonate (2.83 g, 12.4 mmol) in DMF was added dropwise at 60° C. during 1 h. Stirring was then continued at 60° C. for 3 h. The cooled reaction was quenched by addition of water (80 ml) and extracted three times with EtOAc. The combined organic layers were extracted twice with aq 1 M NaOH and washed with water and brine. The organic layer was dried with Na$_2$SO$_4$ and concentrated. The crude product obtained was purified by column chromatography with EtOAc/toluene as eluent to afford the title compound (2.35 g) as a white solid.

$^1$H NMR (CDCl$_3$): δ 2.67 (s, 3H), 2.75 (m, 1H), 2.93 (t, 1H), 3.37-3.40 (m, 1H), 3.96 (dd, 1H), 4.32 (dd, 1H), 5.04 (s, 2H), 6.89 (d, 1H), 7.08 (dd, 1H), 7.32-7.43 (m, 6H).

Acetic acid 5-benzyloxy-2-((R)-1-oxiranylmethoxy)phenyl ester

To a stirred solution of 1-[5-benzyloxy-2-((R)-1-oxiranylmethoxy)phenyl]ethanone (1.0 g, 3.36 mmol) in DCM (20 ml) was added m-chloroperbenzoic acid (1.24 g) and solid NaHCO$_3$ (3.24 g). The mixture was stirred at RT for 3 d. The mixture was filtered and the filtrate washed once with 10% NaHSO$_4$ solution and then twice with NaHCO$_3$ solution. The organic layer was washed with water and brine and dried with Na$_2$SO$_4$. The solvent was removed under reduced pressure. The residue was triturated with ether to give the title compound (0.55 g) as a white solid, which was used without purification.

$^1$H NMR (CDCl$_3$): δ 2.32 (s, 3H), 2.70 (m, 1H), 2.86 (dd, 1H), 3.29-3.30 (m, 1H), 3.92 (dd, 1H), 4.19 (dd, 1H), 5.00 (s, 2H), 6.73 (d, 1H), 6.79 (dd, 1H), 6.94 (d, 1H), 7.33-7.42 (5H, m).

((S)-7-Benzyloxy-2,3-dihydrobenzo[1,4]dioxin-2-yl)methanol

To a stirred solution of acetic acid 5-benzyloxy-2-((R)-1-oxiranylmethoxy)phenyl ester (0.5 g, 1.59 mmol) in THF (10 ml) was added aq 2 M NaOH (1.04 ml). After stirring overnight at RT, THF was removed under reduced pressure and water (20 ml) was added. The water solution was then extracted two times with EtOAc. The combined organic layers washed with water and brine, dried (Na$_2$SO$_4$), and evaporated in vacuo. The crude product (0.45 g) was used without purification.

$^1$H NMR (CDCl$_3$): δ 1.89 (t, 1H), 3.83-3.91 (m, 2H), 4.06 (dd, 1H), 4.23-4.28 (m, 2H), 4.99 (s, 2H), 6.50 (dd, 1H), 6.56 (d, 1H), 6.79 (d, 1H), 7.26-7.41 (m, 5H).

Methanesulfonic acid (R)-7-benzyloxy-2,3-dihydrobenzo[1,4]dioxin-2-ylmethyl ester Prepared according to the procedure described above for methanesulfonic acid (R)-6-benzyloxy-2,3-dihydrobenzo[1,4]dioxin-2-ylmethyl ester.

$^1$H NMR (CDCl$_3$): δ 3.07 (s, 3H), 4.07 (dd, 1H), 4.27 (d, 1H), 4.44-4.49 (m, 3H), 4.99 (s, 2H), 6.51-6.54 (m, 2H), 6.81 (d, 1H), 7.32-7.37 (m, 5H).

3-[(R*)-1-((S)-7-Benzyloxy-2,3-dihydro-benzo[1,4]dioxin-2-ylmethyl)-piperidin-3-yl]-phenol Prepared according to the procedure described above for 3-[(R*)-1-((S)-6-benzyloxy-2,3-dihydro-benzo[1,4]dioxin-2-ylmethyl)-piperidin-3-yl]-phenol.

$^1$H NMR (CDCl$_3$): δ 1.38-1.48 (m, 1H), 1.75 (m 2H), 1.89 (d, 1H), 2.10-2.16 (m, 2H), 2.55 (dd, 1H), 2.70 (dd, 1H), 2.83 (t, 1H), 3.01 (d, 1H), 3.11 (d, 1H), 3.90 (dd, 1H), 4.18 (dd, 1H), 4.33-4.38 (m, 1H), 4.99 (s, 2H), 6.43-6.78 (m, 6H), 7.14 (t, 1H), 7.28-7.41 (m, 5H).

Example 40

(S)-3-[(R*)-3-(3-Hydroxy-phenyl)-piperidin-1-ylmethyl]-2,3-dihydro-benzo[1,4]dioxin-6-ol Prepared according to the procedure described above for (S)-2-[(R*)-3-(3-hydroxy-phenyl)-piperidin-1-ylmethyl]-2,3-dihydro-benzo[1,4]dioxin-6-ol.

$^1$H NMR (DMSO-d$_6$): δ 1.33-1.37 (m, 2H), 1.57-1.79 (m, 2H), 2.02-2.12 (m, 1H), 2.55-2.67 (m, 2H), 2.91 (dd, 2H), 3.86 (dd, 1H), 4.19 (dd, 1H), 4.29 (m, 1H), 6.20-6.22 (m, 2H), 6.57-6.68 (m, 4H), 7.06 (t, 1H), 8.90 (s, 1H), 9.21 (s, 1H).

Example 41

3-[(R*)-1-((S)-8-Benzyloxy-2,3-dihydrobenzo[1,4]dioxin-2-ylmethyl)piperidin-3-yl]phenol Methanesulfonic acid (R)-8-benzyloxy-2,3-dihydrobenzo[1,4]dioxin-2-ylmethyl ester Prepared according to the procedure described above for methanesulfonic acid (R)-6-benzyloxy-2,3-dihydrobenzo[1,4]dioxin-2-ylmethyl ester.

$^1$H NMR (CDCl$_3$): δ2.96 (s, 3H), 4.08 (dd, 1H), 4.29 (d, 1H), 4.41-4.54 (m, 3H), 5.06 (s, 2H), 6.58 (dd, 2H), 6.79 (t, 1H), 7.32-7.41 (m, 5H).

3-[(R*)-1-((S)-8-Benzyloxy-2,3-dihydrobenzo[1,4]dioxin-2-ylmethyl)piperidin-3-yl]phenol Prepared according to the procedure described above for 3-[(R*)-1-((S)-6-benzyloxy-2,3-dihydro-benzo[1,4]dioxin-2-ylmethyl)-piperidin-3-yl]-phenol.

$^1$H NMR (CDCl$_3$): δ 1.35-1.45 (m, 1H), 1.71-1.75 (m, 2H), 1.87 (d, 1H), 2.20-2.28 (m, 2H), 2.65 (dd, 1H), 2.75-2.80 (m, 2H), 2.94 (d, 1H), 3.10 (d 1H), 3.99 (dd, 1H), 4.27 (dd, 1H), 4.37-4.40 (m, 1H), 5.08 (s, 2H), 6.49-6.59 (m, 2H), 6.63-6.78 (m, 4H), 7.11 (t, 1H), 7.25-7.47 (m, 5H).

Example 42

(S)-3-[(R*)-3-(3-Hydroxy-phenyl)-piperidin-1-ylmethyl]-2,3-dihydrobenzo[1,4]dioxin-5-ol Prepared according to the procedure described above for (S)-2-[(R*)-3-(3-hydroxy-phenyl)-piperidin-1-ylmethyl]-2,3-dihydro-benzo[1,4]dioxin-6-ol.

$^1$H NMR (CDCl$_3$): δ 1.52-1.56 (m, 1H), 1.70-2.17 (m, 4H), 2.14 (t, 1H), 2.41 (dd, 1H), 2.93 (dd, 1H), 3.06 (t, 1 h), 3.32-3.35 (m, 2H), 3.89 (dd, 1H), 4.25 (dd, 1H), 4.48 (t, 1H), 6.42 (dd, 1H), 6.54 (dd, 1H), 6.69-6.77 (m, 2H), 6.85-6.87 (m, 2H), 7.23 (t, 1H), 8.2-8-9 (br, s, 2H).

Example 43

(R*)-3-[1-((S)-7-Fluoro-2,3-dihydrobenzo[1,4]dioxin-2-ylmethyl)piperidin-3-yl]phenol A mixture of methanesulfonic acid (R)-(7-fluoro-2,3-dihydrobenzo[1,4]dioxin-2-yl)methyl ester (51 mg, 0.19 mmol), (R*)-3-(piperidin-3-yl)phenol HBr (50 mg, 0.19 mmol) and NaHCO$_3$ (33 mg, 0.39 mmol) in DMF (3.5 ml) was heated at 120° C. for 1.5 h. Water (10 ml) was added to the cooled mixture, which was then extracted with EtOAc (3×10 ml). The combined organic layers were washed several times with water and finally twice with brine. Drying (Na$_2$SO$_4$), filtering and evaporation of the solvent gave the crude product, which was recrystallised from EtOH to afford 24 mg of the title compound as a white solid.

$^1$H NMR (CDCl$_3$): δ 1.35-1.82 (m, 4H), 1.92 (br d, 1H), 2.10-2.22 (m, 2H), 2.58 (dd, J=13.2 and 6 Hz, 1H), 2.69 (dd, J=13.2 and 6 Hz, 1H), 2.75-2.85 (m, 1H), 2.95 (br d, 1H), 3.06 (br d, 1H), 3.92-3.99 (m, 1H), 4.25-4.37 (m, 2H), 6.50-6.82 (m, 6H), 7.17 (dd, J=7.5 Hz, 1H).

Example 44

1-(2,3-Dihydrobenzo[1,4]dioxin-2-ylmethyl)-5-methyl-1,2,3,6-tetrahydropyridine

2-Bromomethyl-2,3-dihydrobenzo[1,4]dioxine (500 mg, 2.18 mmol) and 3-picoline (203 mg, 2.18 mmol) were refluxed in xylene (2 ml) for 4 h. After cooling, the solvent was decanted to give the crude oily picolinium salt, which was dissolved in MeOH (5 ml). NaBH$_4$ (330 mg, 4 eq) was added in small portions to the ice cooled mixture. After stirring for 2 h at RT, MeOH was evaporated, water was added and the mixture extracted with EtOAc. Drying (Na$_2$SO$_4$), filtering and evaporation gave the crude product, which was purified by flash chromatography (heptane/EtOAc).

$^1$H NMR (CDCl$_3$): δ 1.65 (s, 3H), 2.10-2.18 (m, 2H), 2.50-2.80 (m, 4H), 2.86-3.04 (m, 2H), 3.95-4.05 (m, 1H), 4.28-4.40 (m, 2H), 5.45 (m, 1H), 6.77-6.90 (m, 4H).

Example 45

1-(2,3-Dihydrobenzo[1,4]dioxin-2-ylmethyl)-3,5-dimethyl-1,2,3,6-tetrahydropyridine Following the above procedure, 2-bromomethyl-2,3-dihydrobenzo[1,4]dioxine (856 mg, 3.73 mmol) and 3,5-lutidine (400 mg, 3.73 mmol) were refluxed in xylene (2 ml) for 4.5 h. Reduction of the crude lutidinium salt with NaBH$_4$ in MeOH gave the crude title product, which was purified by flash chromatography (heptane/EtOAc).

$^1$H NMR (CDCl$_3$): δ 0.95 (d, J=7 Hz, 3H), 1.64 (s, 3H), 2.08 (m, 1H), 2.35 (m, 1H), 2.60-3.08 (m, 5H), 3.95-4.03 (m, 1H), 4.28-4.37 (m, 2H), 5.31 (s, 1H), 6.78-6.90 (m, 4H).

Example 46

[1-(2,3-Dihydrobenzo[1,4]dioxin-2-ylmethyl)-1,2,5,6-tetrahydropyridin-3-yl]methanol As above, 2-bromomethyl-2,3-dihydrobenzo[1,4]dioxine (500 mg, 2.18 mmol) and pyridin-3-ylmethanol (238 mg, 2.18 mmol) were refluxed in xylene (2 ml) for 4 h. Reduction of the crude pyridinium salt with NaBH$_4$ in MeOH gave the crude title product, which was purified by flash chromatography (heptane/EtOAc).

$^1$H NMR (CDCl$_3$): δ 2.15-2.25 (m, 2H), 2.55-2.82 (m, 4H), 3.03-3.18 (m, 2H), 3.95-4.05 (m, 1H), 4.03 (s, 2H), 4.27-4.40 (m, 2H), 5.75 (m, 1H), 6.77-6.90 (m, 4H).

Example 47

2-(2,3-Dihydrobenzo[1,4]dioxin-2-ylmethyl)-1,2,3,4,5,6,7,8-octahydroisoquinoline As above, 2-bromomethyl-2,3-dihydrobenzo[1,4]dioxine (500 mg, 2.18 mmol) and 5,6,7,8-tetra-hydroisoquinoline (290 mg, 2.18 mmol) were refluxed in xylene (2 ml) for 4 h. Reduction of the crude tetrahydroisoquinolinium salt with NaBH$_4$ in MeOH gave the crude title product, which was purified by flash chromatography (heptane/EtOAc).

$^1$H NMR (CDCl$_3$): δ 1.50-1.65 (m, 4H), 1.77-1.92 (m, 4H), 2.03 (m, 2H), 2.55-2.78 (m, 4H), 2.80-2.98 (m, 2H), 3.95-4.02 (m, 1H), 4.30-4.38 (m, 2H), 6.78-6.90 (m, 4H).

Example 48

2-(2,3-Dihydrobenzo[1,4]dioxin-2-ylmethyl)decahydroisoquinoline

The above described 2-(2,3-dihydrobenzo[1,4]dioxin-2-ylmethyl)-1,2,3,4,5,6,7,8-octahydroiso-quinoline (195 mg, 0.68 mmol) was hydrogenated in MeOH (20 ml) under normal pressure (12 h, 50° C.) to give the crude title compound, which was purified by flash chromatography (heptane/EtOAc).

$^1$H NMR (CDCl$_3$): δ 1.15-1.95 (m, 12H), 2.10-2.42 (m, 2H), 2.45-2.80 (m, 4H), 3.92-4.02 (m, 1H), 4.18-4.36 (m, 2H), 6.75-6.90 (m, 4H).

Example 49

1-(2,3-Dihydrobenzo[1,4]dioxin-2-ylmethyl)piperidine-3-carboxylic acid ethyl ester To a mixture of 2-bromomethyl-2,3-dihydrobenzo[1,4]dioxine (3.0 g, 13.09 mmol) and ethyl nipecotate (2.65 ml, 17.02 mmol) in DMF (15 ml) was added DIPEA (7.5 ml). The reaction mixture was irradiated in the microwave reactor at 110° C. for 3 min. Water (20 ml) was then added. The reaction mixture was extracted with DCM (3×20 ml). The combined organic phases were dried over Na$_2$SO$_4$, filtered and evaporated to give the crude title compound, which was purified by column chromatography (DCM/MeOH, 95:5).

¹H NMR (DMSO-d₆): δ 1.14 (t, 3H), 1.14-1.46 (m, 5H), 2.10-2.80 (m, 6H), 3.94 (m, 1H), 4.05 (m, 2H), 4.28 (m, 2H), 6.82 (m, 4H).

Example 50

[1-(2,3-Dihydrobenzo[1,4]dioxin-2-ylmethyl)piperidin-3-yl]methanol

To a suspension of LiAlH₄ (0.11 g, 2.78 mmol) in dry THF (1 ml) was added 1-(2,3-dihydrobenzo[1,4]dioxin-2-ylmethyl)piperidine-3-carboxylic acid ethyl ester (0.17 g, 0.55 mmol) in dry THF (10 ml). The reaction mixture was refluxed for 2 h. Water was slowly added under cooling and the reaction mixture was extracted with EtOAc (3×20 ml). The combined organic phases were dried (Na₂SO₄), filtered and the filtrate was evaporated to give the title compound.
¹H NMR (DMSO-d₆): δ 0.90 (m, 1H), 1.48 (m, 1H), 1.64 (m, 3H), 1.70-2.20 (m, 3H), 2.80 (m, 2H), 3.20 (m, 3H), 3.95 (dd, 1H), 4.30 (m, 2H), 4.36 (m, 1H), 6.82 (m, 4H).

Example 51

1-(2,3-Dihydrobenzo[1,4]dioxin-2-ylmethyl)-3-methylpiperidine-3-carboxylic acid ethyl ester To a solution of 1-(2,3-dihydrobenzo[1,4]dioxin-2-ylmethyl)piperidine-3-carboxylic acid ethyl ester (10.05 g, 32.90 mmol) in dry THF (100 ml) at −78° C. was slowly added LDA (20.1 ml, 1.8 M). The reaction mixture was stirred at this temperature for 1 h. Methyl iodide (2.25 ml, 36.21 mmol) was then added, the cooling bath removed and stirring was continued for 10 h. After addition of water, the reaction mixture was extracted with EtOAc (3×25 ml). The combined organic phases were dried over Na₂SO₄, filtered and the filtrate was evaporated to give the title compound, which was purified by column chromatography (EtOAc/heptane, 70:30).
¹H NMR (DMSO-d₆): δ 1.06 (s, 3H), 1.15 (t, 3H), 1.58 (m, 2H), 1.94 (m, 1H), 2.10 (m, 2H), 2.40-2.70 (m, 4H), 3.01 (dd, 1H) 3.94-4.05 (m, 3H), 4.28 (m, 2H), 6.85 (m, 4H).

Example 52

1-(2,3-Dihydrobenzo[1,4]dioxin-2-ylmethyl)-3-ethylpiperidine-3-carboxylic acid ethyl ester Prepared according to the procedure described above for 1-(2,3-dihydrobenzo[1,4]dioxin-2-ylmethyl)-3-methylpiperidine-3-carboxylic acid ethyl ester except that ethyl iodide was used instead of methyl iodide.
¹H NMR (DMSO-d₆): δ 0.74 (t, 3H), 1.04 (m, 1H), 1.10-1.20 (m, 3H), 1.38 (m, 1H), 1.48-1.62 (m, 3H), 1.90-2.02 (m, 3H), 2.40-2.82 (m, 3H), 3.05 (m 1H), 3.80-4.12 (m, 3H), 4.20-4.32 (m, 2H), 6.82 (m, 4H).

Example 53

[1-(2,3-Dihydrobenzo[1,4]dioxin-2-ylmethyl)-3-methylpiperidin-3-yl]methanol

To a suspension of LiAlH₄ (0.59 g, 15.54 mmol) in dry THF (45 ml), was added 1-(2,3-dihydrobenzo[1,4]dioxin-2-ylmethyl)-3-methylpiperidine-3-carboxylic acid ethyl ester (1.0 g, 3.13 mmol) in dry THF (5 ml). The reaction mixture was refluxed for 1 h. Water was slowly added and the reaction mixture was extracted with EtOAc (3×20 ml). The combined organic phases were dried over Na₂SO₄, filtered and the filtrate was evaporated to give the desired product which, was purified by column chromatography (EtOAc/heptane, 50:50).
¹H NMR (DMSO-d₆): δ 0.85 (s, 3H), 1.06 (m, 1H), 1.31 (m, 1H), 1.50 (m, 2H), 1.85-2.45 (m, 6H), 3.22 (m, 2H), 3.95 (m, 1H), 4.30 (m, 2H), 4.40 (m, 1H), 6.86 (m, 4H).

Example 54

1-(2,3-Dihydrobenzo[1,4]dioxin-2-ylmethyl)-3-methoxymethyl-3-methylpiperidine

A solution of [1-(2,3-dihydrobenzo[1,4]dioxin-2-ylmethyl)-3-methylpiperidin-3-yl]methanol (0.1 g, 0.36 mmol) in THF (5 ml) was added to NaH (60% in oil, 79.0 mg, 1.79 mmol) which was previously washed with heptane. The reaction mixture was stirred at 70° C. for 1 h and then cooled to RT followed by dropwise addition of a solution of methyl iodide (0.034 ml, 0.54 mmol) in THF (1 ml). Stirring was continued for 1 h. Water was slowly added and the reaction mixture extracted with DCM (3×20 ml). The combined organic phases were dried over Na₂SO₄, filtered and the filtrate was evaporated to give the title compound, which was purified by column chromatography (DCM/MeOH, 90:10).
¹H NMR (DMSO-d₆): δ 0.88 (s, 3H), 1.08 (m, 1H), 1.35 (m, 1H), 1.49 (m, 2H), 1.85-2.45 (m, 6H), 3.15 (m, 2H), 3.31 (s, 3H), 3.95 (m, 1H), 4.27 (m, 2H), 6.86 (m, 4H).

Example 55

1-(2,3-Dihydrobenzo[1,4]dioxin-2-ylmethyl)-3-ethoxymethyl-3-methylpiperidine

Prepared according to the procedure described for 1-(2,3-dihydrobenzo[1,4]dioxin-2-ylmethyl)-3-methoxymethyl-3-methylpiperidine except that ethyl iodide was used instead of methyl iodide.
¹H NMR (DMSO-d₆): δ 0.88 (s, 3H), 1.08 (m, 3H), 1.35 (m, 1H), 1.52 (m, 2H), 1.85-2.45 (m, 4H), 3.15 (m, 2H), 3.31 (s, 3H), 3.40 (m, 2H), 3.95 (m, 1H), 4.28 (m, 2H), 6.86 (m, 4H).

Example 56

3-Chloromethyl-1-(2,3-dihydrobenzo[1,4]dioxin-2-ylmethyl)-3-methylpiperidine

A mixture of phosphorus oxychloride (1.93 ml, 0.02 mmol) and [1-(2,3-dihydrobenzo[1,4]dioxin-2-ylmethyl)-3-methylpiperidin-3-yl]methanol (0.2 g, 0.72 mmol) was refluxed for 3 h. Excess of phosphorus oxychloride was evaporated. Water was slowly added and the reaction mixture was made alkaline with aq NaOH and extracted with DCM (3×5 ml). The combined organic phases were dried over Na₂SO₄, filtered and the filtrate was evaporated to give the title compound, which was purified by column chromatography (DCM/MeOH, 90:10).
¹H NMR (DMSO-d₆): δ 0.93 (s, 3H), 1.19 (m, 1H), 1.50 (m, 3H), 1.85-2.45 (m, 6H), 3.66 (m, 2H), 3.95 (m, 1H), 4.31 (m, 2H), 6.83 (m, 4H).

Example 57

2-[1-(2,3-Dihydrobenzo[1,4]dioxin-2-ylmethyl)-3-methylpiperidin-3-yl]propan-2-ol To a solution of 1-(2,3-dihydrobenzo[1,4]dioxin-2-ylmethyl)-3-methylpiperidine-3-carboxylic acid ethyl ester (1.13 g, 3.53 mmol) in dry THF (50 ml) under nitrogen at 0° C. a solution of methyl magnesium chloride in THF (3.53 ml, 3.0 M) was added dropwise. The resulting solution was refluxed for 2.5 h. Water was then slowly added under cooling and the product was extracted with DCM and purified by column chromatography (DCM/MeOH, 95:5) to give the title compound.

$^1$H NMR (DMSO-d$_6$): δ 0.94 (s, 3H), 1.04 (d, 6H), 1.24 (m, 1H), 1.50 (m, 2H), 1.70-2.48 (m, 7H), 2.52 (br d, 1H), 3.97 (m, 1H), 4.31 (m, 2H), 6.82 (m, 4H).

Example 58

1-(2,3-Dihydrobenzo[1,4]dioxin-2-ylmethyl)-3-(1-methoxy-1-methylethyl)-3-methylpiperidine Prepared according to the procedure described for 1-(2,3-dihydrobenzo[1,4]dioxin-2-ylmethyl)-3-methoxymethyl-3-methylpiperidine except that 2-[1-(2,3-dihydrobenzo[1,4]dioxin-2-ylmethyl)-3-methylpiperidin-3-yl]propan-2-ol was used instead of [1-(2,3-dihydrobenzo[1,4]dioxin-2-ylmethyl)-3-methylpiperidin-3-yl]methanol.

$^1$H NMR (DMSO-d$_6$): δ 0.90-1.05 (m, 9H), 1.08-2.50 (m, 9H), 2.56 (br d, 1H), 3.09 (s, 3H), 3.97 (m, 1H), 4.28 (m, 2H), 6.83 (m, 4H).

Example 59

1-(2,3-Dihydrobenzo[1,4]dioxin-2-ylmethyl)-3-hydroxymethyl-3-methylpiperidin-4-ol To a mixture of 2,3-dihydrobenzo[1,4]dioxine-2-carbonyl chloride (2.0 g, 10.0 mmol) and 4-oxopiperidine-3-carboxylic acid methyl ester (2.14 g, 11.0 mmol) in DMF (5 ml) was added triethylamine (1.54 ml). The reaction mixture was stirred at RT for 5 h. The reaction mixture was taken up in water, made alkaline with aq NaOH and extracted with DCM to give 1-(2,3-dihydrobenzo[1,4]dioxine-2-carbonyl)-4-oxopiperidine-3-carboxylic acid methyl ester. A mixture of this product (0.2 g, 0.62 mmol), K$_2$CO$_3$ (0.17 g, 1.23 mmol) and methyl iodide (0.08 ml, 1.25 mmol) in acetone (20 ml) was irradiated in the microwave reactor at 56° C. for 90 min. Water was added and the reaction mixture extracted with EtOAc (3×5 ml). The combined organic phases were dried over Na$_2$SO$_4$, filtered and the filtrate was evaporated to give 1-(2,3-dihydrobenzo[1,4]dioxine-2-carbonyl)-3-methyl-4-oxopiperidine-3-carboxylic acid methyl ester, which was finally reduced with LiAlH$_4$ in THF to afford the title compound.

$^1$H NMR (DMSO-d$_6$): δ 0.88 (s, 3H), 1.06 (m, 1H), 1.15-3.80 (m, 11H), 3.95 (m, 1H), 4.32 (m, 2H), 4.42 (m, 1H), 6.84 (m, 4H).

Example 60

Acetic acid 1-(2,3-dihydrobenzo[1,4]dioxin-2-ylmethyl)-3-methylpiperidin-3-ylmethyl ester To a solution of [1-(2,3-dihydrobenzo[1,4]dioxin-2-ylmethyl)-3-methylpiperidin-3-yl]methanol (0.5 g, 1.80 mmol), pyridine (0.29 ml) and DCM (40 ml) at 0° C. was added acetic anhydride (0.34 ml). The reaction mixture was stirred at RT for 6 h. Water was slowly added and the reaction mixture extracted with DCM (3×20 ml). The combined organic phases were dried over Na$_2$SO$_4$, filtered and the filtrate was evaporated to give the title compound.

$^1$H NMR (DMSO-d$_6$): δ 0.85 (s, 3H), 1.08 (m, 1H), 1.33 (m, 1H), 1.50 (m, 2H), 1.85-2.45 (m, 7H), 2.49 (s, 3H), 3.95 (m, 1H), 4.25-4.39 (m, 3H), 6.83 (m, 4H).

Example 61

Methanesulfonic acid 1-(2,3-dihydrobenzo[1,4]dioxin-2-ylmethyl)-3-methylpiperidin-3-ylmethyl ester To a solution of [1-(2,3-dihydrobenzo[1,4]dioxin-2-ylmethyl)-3-methylpiperidin-3-yl]methanol (0.92 g, 3.31 mmol) in DCM (40 ml) at 0° C. was added methanesulfonyl chloride (0.51 ml). The reaction mixture was stirred at RT for 12 h. The reaction mixture was made basic with 2 M NaOH and then extracted with DCM (3×20 ml). The combined organic phases were dried over Na$_2$SO$_4$, filtered and the filtrate was evaporated to give the title compound.

$^1$H NMR (DMSO-d$_6$): δ 0.86 (s, 3H), 0.88-1.40 (m, 5H), 1.50 (m, 2H), 2.02-2.32 (m, 5H), 3.16 (m, 3H), 3.96 (m, 1H), 4.29 (m, 2H), 6.81 (m, 4H).

Example 62

[1-(2,3-Dihydrobenzo[1,4]dioxin-2-ylmethyl)-3-ethylpiperidin-3-yl]methanol

Prepared according to the procedure described for [1-(2,3-dihydrobenzo[1,4]dioxin-2-ylmethyl)-3-methylpiperidin-3-yl]methanol except that 1-(2,3-dihydrobenzo[1,4]dioxin-2-ylmethyl)-3-ethyl-piperidine-3-carboxylic acid ethyl ester was used instead of 1-(2,3-dihydrobenzo[1,4]dioxin-2-ylmethyl)-3-methylpiperidine-3-carboxylic acid ethyl ester.

$^1$H NMR (DMSO-d$_6$): δ 0.74 (t, 3H), 1.10 (m, 1H), 1.23-1.50 (m, 6H), 2.01-2.32 (m, 5H), 3.27 (m, 2H), 3.95 (m, 1H), 4.28 (m, 3H), 6.83 (m, 4H).

Example 63

1-(2,3-Dihydrobenzo[1,4]dioxin-2-ylmethyl)-3-ethyl-3-methoxymethylpiperidine

Prepared from [1-(2,3-dihydrobenzo[1,4]dioxin-2-ylmethyl)-3-ethylpiperidin-3-yl]methanol according to the procedure described for 1-(2,3-dihydrobenzo[1,4]dioxin-2-ylmethyl)-3-methoxymethyl-3-methylpiperidine.

$^1$H NMR (DMSO-d$_6$): δ 0.73 (t, 3H), 1.10 (m, 2H), 1.32 (m, 3H), 1.49 (m, 2H), 2.01-2.40 (m, 5H), 3.22-3.30 (m, 5H), 3.95 (m, 1H), 4.26 (m, 2H), 6.81 (m, 4H).

Example 64

1-(2,3-Dihydrobenzo[1,4]dioxin-2-ylmethyl)-3-methoxymethoxymethyl-3-methylpiperidine To a solution of [1-(2,3-dihydrobenzo[1,4]dioxin-2-ylmethyl)-3-methyl-piperidin-3-yl]methanol (0.20 g, 0.72 mmol) in dry DCM (10 ml) at 0° C. was added DIPEA (0.42 ml) and chloromethylmethyl ether (0.11 ml). The reaction mixture was stirred at RT for 16 h. Water was added and the product was extracted with DCM (3×20 ml). The combined organic phases were dried over Na$_2$SO$_4$, filtered and the filtrate was evaporated to give the title compound.

$^1$H NMR (DMSO-d$_6$): δ 0.91 (s, 3H), 1.09 (m, 1H), 1.26 (m, 1H), 1.39 (m, 1H), 1.51 (m, 2H), 2.07-2.39 (m, 4H), 3.23-3.32 (m, 6H), 3.95 (m, 1H), 4.28 (m, 2H), 4.54 (m, 2H), 6.81 (m, 4H).

Example 65

1-[1-(2,3-Dihydrobenzo[1,4]dioxin-2-ylmethyl)-3-ethylpiperidin-3-yl]ethanone

The procedure described for 2-[1-(2,3-dihydrobenzo[1,4]dioxin-2-ylmethyl)-3-methylpiperidin-3-yl]propan-2-ol was repeated except that 1-(2,3-dihydrobenzo[1,4]dioxin-2-ylmethyl)-3-ethylpiperidine-3-carboxylic acid ethyl ester was used as starting material and only one instead of three equivalents of methyl magnesium bromide was used.

$^1$H NMR (DMSO-d$_6$): δ 0.65 (t, 3H), 0.96 (m, 1H), 1.10-1.80 (m, 5H), 2.05 (m, 3H), 2.11 (s, 3H), 2.53 (m, 1H), 2.66 (m, 1H), 3.15 (dd, 1H), 3.93 (m, 1H), 4.34 (m, 1H), 4.34 (m, 1H), 6.82 (m, 4H).

Example 66

1-[1-(2,3-Dihydrobenzo[1,4]dioxin-2-ylmethyl)-3-ethylpiperidin-3-yl]ethanol

To a suspension of LiAlH$_4$ (0.10 g, 2.58 mmol) in dry THF (4 ml), was added 1-[1-(2,3-dihydrobenzo[1,4]dioxin-2-ylmethyl)-3-ethylpiperidin-3-yl]ethanone (0.08 g, 0.26 mmol) in dry THF (3 ml). The reaction mixture was refluxed for 1.5 h. Water was slowly added and the reaction mixture extracted with EtOAc (3×10 ml). The combined organic phases were dried over Na$_2$SO$_4$, filtered and the filtrate was evaporated to give the desired product, which was purified by column chromatography (EtOAc/heptane, 50:50).

$^1$H NMR (CDCl$_3$): δ 0.80 (t, 3H), 1.16 (m, 4H), 1.18-1.90 (m, 5H), 1.97-2.27 (m, 3H), 2.25 (m, 2H), 2.94 (m, 2H), 3.97 (m, 2H), 4.31 (m, 2H), 6.83 (m, 4H).

Example 67

3-Allyloxymethyl-1-(2,3-dihydrobenzo[1,4]dioxin-2-ylmethyl)-3-ethylpiperidine

The procedure described for 1-(2,3-dihydrobenzo[1,4]dioxin-2-ylmethyl)-3-ethyl-3-methoxymethylpiperidine was repeated except that allyl bromide was used instead of methyl iodide.

$^1$H NMR (DMSO-d$_6$): δ 0.76 (t, 3H), 1.12 (m, 1H), 1.13-1.55 (m, 6H), 2.50-2.01 (m, 5H) 3.28 (m, 2H), 3.90 (m, 3H), 4.27 (m, 2H), 5.11 (t, 1H), 5.23 (dd, 1H), 5.87 (m, 1H), 6.84 (m, 4H).

Example 68

2-[1-(2,3-Dihydrobenzo[1,4]dioxin-2-ylmethyl)-3-ethylpiperidin-3-yl-methoxy]ethanol To a solution of [1-(2,3-dihydrobenzo[1,4]dioxin-2-ylmethyl)-3-ethylpiperidin-3-yl]methanol (0.40 g, 1.37 mmol) in DCM (1.5 ml) was added 50% NaOH (6 ml), tetrabutylammonium hydrogensulfate (0.46 g, 1.37 mmol) and tert-butyl bromoacetate (5.35 g, 27.45 mmol). The reaction mixture was stirred at RT for 24 h. Water was added, the reaction mixture was extracted with EtOAc (3×10 ml). The combined organic phases were dried over Na$_2$SO$_4$, filtered and the filtrate was evaporated to give 3-(2-tert-butoxy-ethoxymethyl)-1-(2,3-dihydrobenzo[1,4]dioxin-2-ylmethyl)-3-ethylpiperidine. This crude intermediate (0.20 g, 0.50 mmol) in dry THF (2 ml) was then added to a suspension of LiAlH$_4$ (0.19 g, 5.00 mmol) in dry THF (4 ml). The reaction mixture was refluxed for 1.5 h. Water was slowly added and the reaction mixture was extracted with EtOAc (3×10 ml). The combined organic phases were dried over Na$_2$SO$_4$, filtered and the filtrate was evaporated to give the crude product, which was purified by column chromatography (EtOAc/heptane, 50:50).

$^1$H NMR (DMSO-d$_6$): δ 0.76 (t, 3H), 1.10 (m, 1H), 1.23 (br. s, 2H), 1.34 (m, 3H), 1.48 (m, 2H), 1.80-2.40 (m, 4H), 3.28 (m, 2H), 3.38 (m, 2H), 3.47 (m, 2H), 3.95 (m, 1H), 4.27 (m, 2H), 4.46 (m, 1H), 6.81 (m, 4H).

Example 69

3-Allyloxymethyl-1-(2,3-dihydrobenzo[1,4]dioxin-2-ylmethyl)-3-methyl-piperidine

The procedure described above for 1-(2,3-dihydrobenzo[1,4]dioxin-2-ylmethyl)-3-methoxymethyl-3-methylpiperidine was repeated except that allyl bromide was used instead of methyl iodide.

$^1$H NMR (CDCl$_3$): δ 0.95 (s, 3H), 1.12 (m, 1H), 1.42 (m, 1H), 1.55 (m, 3H), 2.05-2.62 (m, 7H), 3.21-3.32 (m, 2H), 4.00 (m, 1H), 4.31 (m, 1H), 4.35 (m, 1H), 5.14 (d, 1H), 5.25 (d, 1H), 5.90 (m, 1H), 6.83 (m, 4H).

Example 70

3-Allyl-1-(2,3-dihydrobenzo[1,4]dioxin-2-ylmethyl)-piperidine-3-carboxylic acid ethyl ester The procedure described above for 1-(2,3-dihydrobenzo[1,4]dioxin-2-ylmethyl)-3-ethylpiperidine-3-carboxylic acid ethyl ester was repeated except that allyl bromide was used instead of methyl iodide.

$^1$H NMR (DMSO-d$_6$): δ 1.13 (t, 3H), 1.40-2.58 (m, 11H), 3.03 (dd, 1H), 3.96 (m, 2H), 4.04 (m, 1H), 4.26 (m, 2H), 5.03 (m, 2H), 5.62 (m, 1H), 6.78 (m, 4H).

Example 71

[3-Allyl-1-(2,3-dihydrobenzo[1,4]dioxin-2-ylmethyl)piperidin-3-yl]methanol

Prepared from 3-allyl-1-(2,3-dihydrobenzo[1,4]dioxin-2-ylmethyl)-piperidine-3-carboxylic acid ethyl ester using the procedure described for [1-(2,3-dihydrobenzo[1,4]dioxin-2-ylmethyl)-3-methylpiperidin-3-yl]methanol.

$^1$H NMR (DMSO-d$_6$): δ 1.12-1.30 (m, 2H), 1.51 (m, 2H), 2.01-2.45 (m, 7H), 3.26 (m, 3H), 3.95 (m, 1H), 4.29 (m, 2H), 4.41 (m, 1H), 4.99 (s, 1H), 5.02 (d, 1H), 5.81 (m, 1H), 6.81 (m, 4H).

Example 72

3-Allyl-1-(2,3-dihydrobenzo[1,4]dioxin-2-ylmethyl)-3-methoxymethylpiperidine

Prepared from [3-allyl-1-(2,3-dihydrobenzo[1,4]dioxin-2-ylmethyl)-piperidin-3-yl]methanol using the procedure described for 1-(2,3-dihydrobenzo[1,4]dioxin-2-ylmethyl)-3-methoxymethyl-3-methylpiperidine.

$^1$H NMR (DMSO-d$_6$): δ 1.15-1.52 (m, 5H), 1.98-2.50 (m, 6H), 3.10 (m, 2H), 3.26 (m, 3H), 3.30 (m, 1H), 3.95 (m, 1H), 4.27 (m, 2H), 5.00 (br d, 1H), 5.02 (m, 1H), 5.79 (m, 1H), 6.81 (m, 4H).

Example 73

3-Allyl-1-(2,3-dihydrobenzo[1,4]dioxin-2-ylmethyl)-3-ethoxymethylpiperidine

The procedure described for 1-(2,3-dihydrobenzo[1,4]dioxin-2-ylmethyl)-3-methoxymethyl-3-methylpiperidine was repeated except that ethyl iodide was used instead of methyl iodide.

$^1$H NMR (CDCl$_3$): δ 1.16 (t, 3H), 1.18-1.77 (m, 3H), 1.90-2.88 (m, 8H), 3.24 (m, 1H), 3.42 (q, 2H), 3.63 (m, 2H), 3.98 (m, 1H), 4.28 (m, 2H), 5.03 (m, 2H), 5.78 (m, 1H), 6.84 (m, 4H).

Example 74

1-(2,3-Dihydrobenzo[1,4]dioxin-2-ylmethyl)-3-methyl-3-(2,2,2-trifluoroethoxymethyl)-piperidine

A mixture of methanesulfonic acid 1-(2,3-dihydrobenzo[1,4]dioxin-2-ylmethyl)-3-methylpiperidin-3-ylmethyl ester (0.35 g, 0.98 mmol), K$_2$CO$_3$ (0.68 g) and trifluoroethanol (4 ml) was irradiated in a microwave reactor at 150° C. for 10 min. Water was added and the reaction mixture was extracted with DCM (2×20 ml). The combined organic phases were dried over Na$_2$SO$_4$, filtered and the filtrate was evaporated to give the title compound, which was purified by column chromatography (DCM/MeOH, 90:10).

$^1$H NMR (DMSO-d$_6$): δ 0.89 (m, 3H), 1.10 (m, 1H), 1.25-1.60 (m, 4H), 2.01-2.50 (m, 4H), 3.39 (m, 1H), 3.48 (m, 2H), 3.80-4.10 (m, 3H), 4.28 (m, 2H), 6.81 (m, 4H).

Example 75

2-[1-(2,3-Dihydrobenzo[1,4]dioxin-2-ylmethyl)-3-methylpiperidin-3-ylmethoxy]ethanol

Prepared from [1-(2,3-dihydrobenzo[1,4]dioxin-2-ylmethyl)-3-methylpiperidin-3-yl]methanol using the procedure described above for 2-[1-(2,3-dihydrobenzo[1,4]dioxin-2-ylmethyl)-3-ethylpiperidin-3-yl-methoxy]ethanol.

$^1$H NMR (CDCl$_3$): δ 0.96 (s, 3H), 1.16 (m, 1H), 1.40 (m, 1H), 1.59 (m, 2H), 2.16 (d, 1H), 2.30 (br. s, 1H), 2.46 (d, 1H), 2.47-2.50 (m, 3H), 3.26 (d, 1H), 3.39 (dd, 1H), 3.45 (d, 1H), 3.52 (m, 2H), 3.70 (m, 2H), 4.29 (m, 2H), 6.83 (m, 4H).

Example 76

[1-(2,3-Dihydrobenzo[1,4]dioxin-2-ylmethyl)piperidin-3-yl]acetic acid ethyl ester

To a mixture of 2-bromomethyl-2,3-dihydrobenzo[1,4]dioxine (1.34 g, 5.84 mmol), piperidin-3-yl-acetic acid ethyl ester (1.0 g, 5.84 mmol) in acetonitrile (25 ml) was added K$_2$CO$_3$ (0.81 g, 5.84 mmol) and KI (0.97 g, 5.84 mmol). The reaction mixture was irradiated under microwaves at 82° C. for 8 h. Water (100 ml) was then added. The reaction mixture was extracted with DCM (3×50 ml). The combined organic phases were dried (Na$_2$SO$_4$), filtered and the filtrate was evaporated to give the title compound, which was purified by column chromatography (DCM/MeOH, 95:5).

$^1$H NMR (DMSO-d$_6$): δ 0.83 (m, 1H), 1.16 (t, 3H), 1.18-1.59 (m, 3H), 1.80-2.40 (m, 5H), 2.52 (m, 2H), 2.79 (m, 2H), 3.93 (dd, 1H), 4.04 (q, 2H), 4.29 (m, 2H), 6.81 (m, 4H).

Example 77

2-[1-(2,3-Dihydrobenzo[1,4]dioxin-2-ylmethyl)piperidin-3-yl]ethanol

To a suspension of LiAlH$_4$ (0.12 g, 3.16 mmol) in dry THF (4 ml) was added [1-(2,3-dihydrobenzo-[1,4]dioxin-2-ylmethyl)piperidin-3-yl]acetic acid ethyl ester 2.0 g (0.62 mmol) in dry THF (2 ml). The reaction mixture was refluxed for 1.5 h. Water was slowly added and the reaction mixture was extracted with EtOAc (3×20 ml). The combined organic phases were dried (Na$_2$SO$_4$), filtered and the filtrate was evaporated to give the desired product which was purified by column chromatography (EtOAc/heptane, 50:50).

$^1$H NMR (DMSO-d$_6$): δ 0.84 (m, 1H), 1.14-2.03 (m, 8H), 2.52 (m, 2H), 2.74-2.87 (m, 2H), 3.42 (m, 2H), 3.94 (dd, 1H), 4.29 (m, 3H), 6.81 (m, 4H).

Example 78

1-(2,3-Dihydrobenzo[1,4]dioxin-2-ylmethyl)-3-(2-methoxyethyl)piperidine

A solution of 2-[1-(2,3-dihydrobenzo[1,4]dioxin-2-ylmethyl)piperidin-3-yl]ethanol (0.1 g, 0.36 mmol) in THF (5 ml) was added NaH (79.0 mg, 1.79 mmol), which was previously washed with heptane. The reaction mixture was stirred at 70° C. for 1 h followed by a dropwise addition of a solution of iodomethane (0.034 ml, 0.54 mmol) in THF (1 ml). Stirring was continued for 1 h. Water was slowly added and the reaction mixture was extracted with DCM (3×20 ml). The combined organic phases were dried (Na$_2$SO$_4$), filtered and the filtrate was evaporated to give the title compound, which was purified by column chromatography (DCM/MeOH, 90:10).

$^1$H NMR (DMSO-d$_6$): δ 0.84 (m, 1H), 1.32-2.13 (m, 9H), 2.74-2.83 (m, 2H), 3.19 (s, 3H), 3.32 (m, 3H), 3.94 (dd, 1H), 4.29 (m, 2H), 6.83 (m, 4H).

Example 79

1-(2,3-Dihydrobenzo[1,4]dioxin-2-ylmethyl)piperidine-3-carboxylic acid amide

To a mixture of 2-bromomethyl-2,3-dihydrobenzo[1,4]dioxine (0.2 g, 0.87 mmol) and piperidine-3-carboxylic acid amide (0.13 g, 1.05 mmol) in acetonitrile (20 ml) was added K$_2$CO$_3$ (0.60 g, 4.36 mmol) and KI (0.72 g, 4.36 mmol). The reaction mixture was refluxed for 2 h. Water (100 ml) was then added. The reaction mixture was extracted with EtOAc (3×5 ml). The combined organic phases were dried (Na$_2$SO$_4$), filtered and the filtrate was evaporated to give the title compound, which was purified by column chromatography (EtOAc/heptane, 50:50).

$^1$H NMR (DMSO-d$_6$): δ 1.40-1.80 (m, 4H), 1.80-2.40 (m, 3H), 2.50-2.80 (m, 4H), 3.94 (m, 1H), 4.30 (m, 2H), 6.83 (m, 4H), 7.31 (s, 2H).

Example 80

1-(2,3-Dihydrobenzo[1,4]dioxin-2-ylmethyl)piperidine-3-carbonitrile

Thionyl chloride (20 ml) was added under cooling to 1-(2,3-dihydrobenzo[1,4]dioxin-2-ylmethyl)-piperidine-3-carboxylic acid amide (2.34 g, 8.46 mmol). The reaction mixture was refluxed for 3 h. Excess of thionyl chloride was evaporated. Water was slowly added to the residue, the mixture was made alkaline with aq NaOH and extracted with DCM (3×5 ml). The combined organic phases were dried (Na$_2$SO$_4$), filtered and the filtrate was evaporated to give the title compound, which was purified by column chromatography (DCM/MeOH, 90:10).

$^1$H NMR (DMSO-d$_6$): δ 1.20 (m, 1H), 1.40-1.70 (m, 5H), 2.50-2.62 (m, 5H), 3.98 (m, 1H), 4.32 (m, 2H), 6.82 (m, 4H).

Example 81

C-[1-(2,3-Dihydrobenzo[1,4]dioxin-2-ylmethyl)piperidin-3-yl]methylamine

To a suspension of LiAlH$_4$ (0.62 g, 16.30 mmol) in dry THF (15 ml) was added 1-(2,3-dihydrobenzo[1,4]dioxin-2-ylmethyl)-piperidine-3-carboxylic acid amide (0.45 g, 01.63 mmol) in dry THF (5 ml). The reaction mixture was heated under microwaves at 66° C. for 1 h. Water was slowly added and the mixture extracted with EtOAc (3×20 ml). The combined organic phases were dried (Na$_2$SO$_4$), filtered and the filtrate was evaporated to give the desired product, which was purified by column chromatography (DCM/MeOH, 98:2).

$^1$H NMR (DMSO-d$_6$): δ 0.84 (m, 1H), 1.40-1.80 (m, 7H), 2.01 (m, 1H), 2.33 (m, 2H), 2.70-2.90 (m, 3H), 3.30 (br. s, 1H), 3.94 (m, 1H), 4.28 (m, 2H), 6.83 (m, 4H).

Example 82

1-(2,3-Dihydrobenzo[1,4]dioxin-2-ylmethyl)piperidin-3-ol

A mixture of 2-bromomethyl-2,3-dihydrobenzo[1,4]dioxine (2.26 g, 9.88 mmol), piperidin-3-ol (1.0 g, 9.88 mmol) and K$_2$CO$_3$ (6.8 g, 49.43 mmol) in DMF (30 ml) was heated under microwaves at 153° C. for 120 min to give the crude title compound after the usual work-up. The product was purified by column chromatography (DCM/MeOH, 98:2).

$^1$H NMR (DMSO-d$_6$): δ 1.04 (m, 1H), 1.38 (m, 1H), 1.41 (m, 1H), 1.59 (m, 1H), 1.60-2.10 (m, 3H), 2.40-2.90 (m, 3H), 3.45 (br. s, 1H), 3.93 (m, 1H), 4.29 (m, 2H), 4.61 (m, 1H), 6.82 (m, 4H).

Example 83

2-(2,3-Dihydrobenzo[1,4]dioxin-2-ylmethyl)-1,2,3,4-tetrahydro-isoquinoline-8-carboxylic acid methyl ester To a mixture of 2-bromomethyl-2,3-dihydrobenzo[1,4]dioxine (0.2 g, 0.88 mmol) and 1,2,3,4-tetrahydroisoquinoline-8-carboxylic acid methyl ester (0.14 g, 0.88 mmol) in DMF (10 ml) was added K$_2$CO$_3$ (0.61 g, 4.41 mmol). The reaction mixture was heated under microwaves at 140° C. for 10 min. Water was then added and the mixture extracted with DCM (3×5 ml). The combined organic phases were dried (Na$_2$SO$_4$), filtered and the filtrate was evaporated to give the title compound, which was purified by column chromatography (DCM/MeOH, 95:5).

$^1$H NMR (DMSO-d$_6$): δ 2.70-2.90 (m, 6H), 3.62 (s, 2H), 3.89 (s, 3H), 3.92 (m, 1H), 4.28 (m, 2H), 6.85 (m, 4H), 7.01 (d, 1H), 7.11 (t, 1H), 7.18 (d, 1H).

Example 84

[2-(2,3-Dihydrobenzo[1,4]dioxin-2-ylmethyl)-1,2,3,4-tetrahydroisoquinolin-8-yl]methanol To a suspension of LiAlH$_4$ (0.20 g, 5.44 mmol) in dry THF (10 ml) was added 2-(2,3-dihydrobenzo-[1,4]dioxin-2-ylmethyl)-1,2,3,4-tetrahydroisoquinoline-8-carboxylic acid methyl ester (0.18 g, 0.54 mmol). The reaction mixture was heated under microwaves at 80° C. for 10 min. Water (10 ml) was slowly added under cooling followed by extraction with EtOAc (3×5 ml). The combined organic phases were dried (Na$_2$SO$_4$), filtered and the filtrate was evaporated to give the title compound, which was purified by column chromatography (EtOAc/heptane, 50:50).

$^1$H NMR (DMSO-d$_6$): δ 2.70-2.90 (m, 6H), 3.66 (m, 2H), 4.00 (dd, 1H), 4.38 (dd, 1H), 4.42 (d, 2H), 4.44 (q, 1H), 5.01 (t, 1H), 6.84 (m, 4H), 7.01 (d, 1H), 7.10 (t, 1H), 7.16 (d, 1H).

Example 85

(S)-1-((R)-2,3-Dihydrobenzo[1,4]dioxine-2-carbonyl)-3-methylpiperidine-3-carboxylic acid ethyl ester

3-Methylpiperidine-3-carboxylic acid ethyl ester

Ethyl-5-chloro-2-cyano-2-methylpentanoate (DE 31 39 301 A1) (10.43 g, 51.2 mmol), PtO$_2$ hydrate (1.16 g) and concentrated HCl (12.5 ml) in absolute EtOH (125 ml) were stirred and heated at 40° C. under hydrogen at normal pressure for 2 h. The cooled solution was filtered. After evaporation of the solvent, the residue was dissolved in absolute EtOH (125 ml). The solution was cooled with an ice-water bath and triethylamine (9.8 g, 96.8 mmol) was added. After the addition the mixture was stirred at RT for 16 h under nitrogen atmosphere. The solvent and triethylamine were evaporated, and the residue was dissolved in DCM (100 ml) and extracted with 1 M HCl (3×100 ml). After separating the layers, ice (150 g) and 5 M NaOH (100 ml) were added to the aqueous layer, which was then extracted with DCM (3×60 ml). The combined extracts were dried, filtered and evaporated to dryness followed by vacuum distillation (bp. 62-65° C./2 mbar) to give 6.0 g of the title compound as a colorless liquid.

$^1$H NMR (CDCl$_3$): δ 1.09 (s, 3H), 1.27 (t, 3H), 1.33-1.57 (m, 4H), 2.17 (m, 1H), 2.41 (d, 1H), 2.58 (m, 1H), 2.92 (m, 1H), 3.32 (dd, 1H), 4.17 (m, 2H).

(S)-3-methyl-piperidine-3-carboxylic acid ethyl ester

The title compound was resolved from the above racemate according to the method described in Org. Lett., 7 (2005) 55.

(S)-1-((R)-2,3-Dihydrobenzo[1,4]dioxine-2-carbonyl)-3-methylpiperidine-3-carboxylic acid ethyl ester (R)-2,3-Dihydrobenzo[1,4]dioxine-2-carbonyl chloride (6.05 g, 30.5 mmol) in DCM (20 ml) was added to a stirred mixture of (S)-3-methyl-piperidine-3-carboxylic acid ethyl ester (5.0 g, 29.2 mmol), DIPEA (5.5 ml, 31.7 mmol) and DCM (30 ml), previously cooled down to 5° C. The cooling bath was removed and stirring continued at RT for 1 h. The reaction mixture was washed twice with 1 M HCl, twice with sat. aq NaHCO$_3$ and twice with water and dried with Na$_2$SO$_4$. Solvent was evaporated to give 9.66 g of the title compound.

¹H NMR (DMSO-d₆): δ 1.05-1.75 (m, 9H), 1.85-2.15 (m, 1H), 2.75-3.18 (m, 1H), 3.35-3.78 (m, 2H), 3.95-4.25 (m, 4H), 4.25-4.37 (m, 1H), 5.15-5.50 (m, 1H), 6.75-6.95 (m, 4H).

Example 86

Lithium (S)-1-[(S)-1-(2,3-dihydrobenzo[1,4]dioxin-2-yl)methyl]-3-methyl-piperidine-3-carboxylate (S)-1-((R)-2,3-Dihydrobenzo[1,4]dioxine-2-carbonyl)-3-methylpiperidine-3-carboxylic acid ethyl ester (512 mg, 1.60 mmol), 1 M lithium hydroxide (4.81 ml, 4.81 mmol) and THF:H₂O solution (9:1) (5 ml) were heated under microwaves at 100° C. for 26 h. The mixture was filtered and evaporated to dryness. The residue was dissolved in water and washed twice with EtOAc and the aqueous phase was evaporated to dryness to give 353 mg of the title compound.

¹H NMR (DMSO-d₆): δ 0.98 (s, 3H), 1.06-1.16 (m, 1H), 1.40-1.49 (m, 1H), 1.50-1.61 (m, 1H), 1.69-1.79 (m, 1H), 2.09-2.18 (m, 1H), 2.21-2.30 (m, 1H), 2.37-2.50 (m, 3H), 2.60-2.69 (m, 1H), 3.96-4.03 (m, 1H), 4.18-4.26 (m, 1H), 4.30-4.37 (dd, 1H, J=2.4, 11.2 Hz), 6.76-6.86 (m, 4H).

Example 87

{(S)-1-[(S)-1-(2,3-Dihydrobenzo[1,4]dioxin-2-yl)methyl]-3-methylpiperidin-3-yl}methanol A mixture of (S)-1-((R)-2,3-dihydrobenzo[1,4]dioxine-2-carbonyl)-3-methylpiperidine-3-carboxylic acid ethyl ester (27.7 g, 83.1 mmol) and THF (150 ml) was added to a cooled (0° C.) mixture of dry THF (150 ml) and LiAlH₄ (10 g, 264 mmol). The reaction mixture was refluxed for 2 h, after which it was cooled to RT and water was added. The mixture was extracted twice with EtOAc and dried with Na₂SO₄. Solvent was evaporated to give 21.93 g of the title compound.

¹H NMR (CD₃OD): δ 0.93 (s, 3H), δ 1.14-1.21 (m, 1H), 1.42-1.48 (m, 1H), 1.61-1.69 (m, 2H), 2.22-2.27 (m, 1H), 2.32-2.42 (m, 2H), 2.49-2.60 (m, 3H), 3.40-3.47 (m, 2H), 3.92-3.97 (m, 1H), 4.23-4.31 (m, 2H), 6.76-6.82 (m, 4H).

Example 88

2-{(S)-1-[(S)-1-(2,3-Dihydrobenzo[1,4]dioxin-2-yl)methyl]-3-methylpiperidin-3-ylmethoxy}-ethanol A mixture of {(S)-1-[(S)-1-(2,3-Dihydrobenzo[1,4]dioxin-2-yl)methyl]-3-methylpiperidin-3-yl}-methanol (5.12 g, 18.5 mmol), 50% NaOH (125 ml) and tetrabutylammonium bromide (0.585 g, 1.8 mmol) was stirred at RT for 15 min and then heated up to 60° C. 2-(2-Bromoethoxy)tetrahydropyran (11.3 g, 54.0 mmol) was added to the reaction mixture at 60° C. during 2 h. After the addition the reaction mixture was stirred at 60° C. for 5 h. The reaction mixture was cooled down to RT and brine and water was added. The reaction mixture was extracted three times with toluene. The toluene phases were combined and washed twice with water and once with brine, dried (Na₂SO₄) and evaporated to give (S)-1-[(S)-1-(2,3-dihydrobenzo[1,4]dioxin-2-yl)methyl]-3-methyl-3-[2-(tetra-hydropyran-2-yloxy)ethoxymethyl]piperidine. To remove the THP group, this compound was stirred in water (100 ml) and conc. HCl (10 ml) at RT for 3 h. The reaction mixture was washed twice with toluene and pH of the water phase was adjusted to 11-12 with NaOH. The alkaline phase was extracted twice with toluene. The combined extracts were washed twice with water and once with brine and dried (Na₂SO₄). Toluene was evaporated and EtOAc was added to the residue. EtOAc was evaporated to give 4.74 g of the crude title compound. A mixture of the crude title compound (4.6 g, 14.3 mmol), EtOAc (50 ml) and (−)-di-p-toluoyl-L-tartaric acid (5.53 g, 14.3 mmol) was stirred at 60° C. for 1 hour. The reaction mixture was cooled to RT and stirred for a few hours. The precipitate was filtered, washed with EtOAc and dried under vacuum at 80° C. The crude product (8.9 g, 12.6 mmol) was recrystallized from IPA (90 ml) to give 7.5 g of the di-p-toluoyl-L-tartrate salt of 2-{(S)-1-[(S)-1-(2,3-dihydrobenzo[1,4]dioxin-2-yl)methyl]-3-methyl-piperidin-3-ylmethoxy}ethanol. This salt was stirred in EtOAc (50 ml) and water (50 ml). The pH of the mixture was adjusted to 9 (1 M NaOH) and stirring was continued at RT for 30 min. The phases were separated and the water phase was extracted twice with EtOAc. The organic layers were combined, dried (Na₂SO₄) and evaporated to give 3.4 g of the pure title compound.

¹H NMR (CDCl₃): δ 0.96 (s, 3H), 1.11-1.18 (m, 1H), 1.39-1.45 (m, 1H), 1.56-1.62 (m, 2H), 2.09-2.62 (m, 7H), 3.27-3.29 (d, 1H), 3.44-3.46 (d, 1H), 3.51-3.55 (m, 2H), 3.69-3.72 (m, 2H), 3.97-4.02 (m, 1H), 4.24-4.33 (m, 2H), 6.80-6.88 (m, 4H).

Example 89

2-{(S)-1-[(S)-1-(2,3-Dihydrobenzo[1,4]dioxin-2-yl)methyl]-3-methylpiperidin-3-ylmethoxy}-ethanol D-tartrate A mixture of 2-{(S)-1-[(S)-1-(2,3-dihydrobenzo[1,4]dioxin-2-yl)methyl]-3-methylpiperidin-3-ylmethoxy}-ethanol (3.1 g, 9.6 mmol) and acetone (30 ml) was heated to 50° C. and D-tartaric acid (1.45 g, 9.7 mmol) was added in small portions at 50° C. The reaction mixture was refluxed for 1 h, after which it was cooled down to RT and the solvent was evaporated. The residue was dried under vacuum at 40° C. to give 4.17 g of the title salt.

¹H NMR (CDCl₃): δ 0.99 (s, 3H), 1.20-1.32 (m, 1H), 1.52-1.62 (m, 1H), 1.68-1.78 (m, 1H), 1.82-1.94 (m, 1H), 2.35-2.60 (m, 2H), 2.78-2.83 (m, 1H), 2.90-3.31 (m, 4H), 3.56-3.59 (m, 3H), 3.70-3.74 (m, 2H), 4.02-4.06 (m, 1H), 4.27-4.30 (m, 2H), 4.56-4.57 (m, 1H), 6.84-6.88 (m, 4H).

Example 90

(S)-1-[(S)-1-(2,3-Dihydrobenzo[1,4]dioxin-2-yl)methyl]-3-(2-methoxyethoxymethyl)-3-methylpiperidine Prepared from {(S)-1-[(S)-1-(2,3-dihydrobenzo[1,4]dioxin-2-yl)methyl]-3-methylpiperidin-3-yl}-methanol using the procedure for preparation of 1-(2,3-dihydrobenzo[1,4]dioxin-2-ylmethyl)-3-methoxymethyl-3-methylpiperidine except that 1-bromo-2-methoxyethane was used instead of methyl iodide.

¹H NMR (CDCl₃): δ 0.96 (s, 3H), 0.98-1.75 (m, 7H), 2.10-2.60 (m, 5H), 3.32-3.34 (m, 1H), 3.36 (s, 3H), 3.56 (m, 3H), 3.98 (dd, 1H), 4.24 (m, 1H), 4.35 (m, 1H), 6.83 (m, 4H).

Example 91

(S)-1-[(S)-1-(2,3-Dihydrobenzo[1,4]dioxin-2-yl)methyl]-3-methyl-3-(2,2,2-trifluoroethoxymethyl)piperidine Prepared from {(S)-1-[(S)-1-(2,3-dihydrobenzo[1,4]dioxin-2-yl)methyl]-3-methylpiperidin-3-yl}methanol as described for 1-(2,3-dihydrobenzo[1,4]dioxin-2-ylmethyl)-3-methyl-3-(2,2,2-trifluoroethoxymethyl)piperidine.

$^1$H NMR (CDCl$_3$): δ 0.96 (s, 3H), 1.14 (m, 1H), 1.42 (m, 1H), 1.56 (m, 3H), 2.10 (dd, 1H), 2.40 (d, 1H), 2.52 (m, 3H), 3.45 (dd, 1H), 3.53 (t, 1H), 3.81 (q, 2H), 3.98 (m, 1H), 4.30 (m, 2H), 6.83 (m, 4H).

Example 92

Methanesulfonic acid (S)-1-[(S)-1-(2,3-dihydrobenzo[1,4]dioxin-2-yl)methyl]-3-methyl-piperidin-3-ylmethyl ester A mixture of 3-{(R)-1-[(S)-1-(2,3-dihydrobenzo[1,4]dioxin-2-yl)methyl]piperidin-3-yl}phenol (1.05 g, 3.79 mmol) and triethylamine (212 δl, 0.585 g, 5.78 mmol) in DCM was cooled to 0° C. and methanesulfonyl chloride (448 µl, 0.66 g, 5.78 mmol) in DCM (1 ml) was added. The mixture was stirred at RT for 2 h. The reaction mixture was quenched with water and washed two times with sat. aq NaHCO$_3$. The organic phase was dried (Na$_2$SO$_4$) and evaporated to dryness to give 1.048 g of the title compound.

$^1$H NMR (CDCl$_3$): δ 1.02 (s, 3H), 1.15-1.32 (m, 1H), 1.45-1.74 (m, 3H), 2.03-2.40 (m, 2H), 2.41-2.83 (m, 4H), 3.00 (s, 3H), 3.93-4.39 (m, 5H), 6.80-6.90 (m, 4H).

Example 93

Thioacetic acid S-{(S)-1-[(S)-1-(2,3-dihydrobenzo[1,4]dioxin-2-yl)methyl]-3-methylpiperidin-3-ylmethyl}ester A mixture of methanesulfonic acid (S)-1-[(S)-1-(2,3-dihydrobenzo[1,4]dioxin-2-yl)methyl]-3-methylpiperidin-3-ylmethyl ester (927 mg, 2.61 mmol), thioacetic acid (373 µl, 399 mg, 5.24 mmol) and K$_2$CO$_3$ (721 mg, 5.22 mmol) in DMF (35 ml) was heated at 95° C. for 10 h. The mixture was evaporated to dryness, dissolved in DCM and washed two times with sat. aq NaHCO$_3$. The organic phase was washed with brine, dried (Na$_2$SO$_4$) and evaporated to dryness to give 794 mg of the title compound.

$^1$H NMR (CDCl$_3$): δ 0.91 (s, 3H), 1.18-1.28 (m, 1H), 1.35-1.45 (m, 1H), 1.50-1.67 (m, 2H), 2.01-2.64 (m, 9H), 2.93-3.10 (m, 2H), 3.93-4.02 (m, 1H), 4.18-4.38 (m, 2H), 6.78-6.90 (m, 4H).

Example 94

2-{(S)-1-[(S)-1-(2,3-Dihydrobenzo[1,4]dioxin-2-yl)methyl]-3-methylpiperidin-3-ylmethylsulfanyl}ethanol Dry MeOH (1 ml) was added to NaOH (35 mg, 0.88 mmol) and the suspension was added to an oven dried thioacetic acid S-{(S)-1-[(S)-1-(2,3-dihydrobenzo[1,4]dioxin-2-yl)methyl]-3-methylpiperidin-3-ylmethyl}ester (141 mg, 0.42 mmol) under nitrogen atmosphere. The mixture was stirred at RT for 1 h. 2-Chloroethanol (59 µl, 71 mg, 0.88 mmol) in dry DMF (2 ml) was added and the reaction mixture was stirred at RT for 30 min. The mixture was diluted with EtOAc and washed two times with sat. aq NaHCO$_3$. The combined organic phases were dried (Na$_2$SO$_4$) and evaporated to dryness. The crude product was purified by flash chromatography using a gradient of heptane and EtOAc as eluent to give 17 mg of the title compound.

$^1$H NMR (CDCl$_3$): δ 0.96 (s, 3H), 1.19-1.29 (m, 2H), 1.41-1.51 (m, 1H), 1.53-1.65 (m, 2H), 2.02-2.11 (m, 1H), 2.15-2.25 (m, 1H), 2.48-2.82 (m, 8H), 3.67-3.80 (m, 2H), 3.95-4.02 (m, 1H), 4.27-4.34 (m, 2H), 6.79-6.89 (m, 4H).

Example 95

{(S)-1-[(S)-1-(2,3-Dihydrobenzo[1,4]dioxin-2-yl)methyl]-3-methylpiperidin-3-ylmethoxy}acetic acid tert-butyl ester To a stirred solution of {(S)-1-[(S)-1-(2,3-dihydrobenzo[1,4]dioxin-2-yl)methyl]-3-methylpiperidin-3-yl}methanol (0.516 g, 1.8 mmol) in toluene (4 ml) was added tetrabutylammonium bromide (0.12 g) and 50% NaOH (4 ml). The mixture was stirred at RT for 15 min and bromoacetic acid tert-butyl ester (0.53 g) was added. After vigorous stirring at RT overnight, the reaction was quenched by addition of brine (15 ml) and the aqueous phase extracted twice with toluene. The combined organic phases were extracted with 1 M HCl solution and the acidic water phase was basified by addition of NaOH. Extraction with toluene and evaporation afforded the title compound (0.48 g) as an oil.

$^1$H NMR (DMSO-d$_6$): δ 0.91 (s, 3H), 1.05-1.11 (m, 1H), 1.42 (s, 9H), 1.45-1.52 (d, 2H), 2.14 (d, 1H), 2.30 (d, 2H), 2.45-2.54 (m, 4H), 3.31 (dd, 2H), 3.90-3.99 (m, 3H), 4.25-4.31 (m, 2H), 6.79-6.86 (m, 4H).

Example 96

Sodium {(S)-1-[(S)-1-(2,3-dihydrobenzo[1,4]dioxin-2-yl)methyl]-3-methylpiperidin-3-yl-methoxy}acetate To a solution of {(S)-1-[(S)-1-(2,3-dihydrobenzo[1,4]dioxin-2-yl)methyl]-3-methylpiperidin-3-ylmethoxy}acetic acid tert-butyl ester (0.92 g, 2.11 mmol) in DCM (10 ml) was added trifluoroacetic acid (10 ml). The mixture was stirred at RT overnight, after which it was evaporated to dryness. Water was added to the residue and the solution was made basic by addition of aq NaOH. The alkaline water phase was extracted several times with DCM and the combined organic layers were dried with Na$_2$SO$_4$ and evaporated. The crude residue was triturated with IPA to afford the title compound (0.49 g) as a white solid.

$^1$H NMR (DMSO-d$_6$): δ 0.91 (s, 3H), 1.04-1.09 (m, 1H), 1.36-1.41 (m, 1H), 1.52 (m, 2H), 2.20 (s, 2H), 2.36 (s, 2H), 2.48 (m, 3H), 3.18 (d, 1H), 3.31 (d, 1H), 3.54 (dd, 2H), 3.95 (dd, 1H), 4.25-4.31 (m, 2H), 6.82-6.84 (m, 4H).

Example 97

2-[(S)-1-((S)-7-Fluoro-2,3-dihydrobenzo[1,4]dioxin-2-ylmethyl)-3-methylpiperidin-3-yl-methoxy]ethanol (S)-1-Benzyl-3-methylpiperidine-3-carboxylic acid ethyl ester (S)-3-Methylpiperidine-3-carboxylic acid ethyl ester (1.16 g, 6.8 mmol), benzyl chloride (0.82 ml, 7.1 mmol), K$_2$CO$_3$ (1.22 g, 8.8 mmol) and KI (0.056 g) were stirred and heated in DMF (50 ml) for 2.5 h. The cooled solution was poured into water and extracted with EtOAc (3×50 ml). The combined extracts were washed several times with water and finally with brine. Drying, filtering and evaporation of the solvent gave 1.64 g of the target compound as a yellowish oil.

¹H NMR (CDCl₃): δ 1.12 (s, 3H), 1.23 (t, 3H, J=7 Hz), 1.15-2.15 (m, 6H), 2.60 (m, 1H), 2.98 (m, 1H), 3.40 (d, J$_{AB}$=13.5 Hz, 1H), 3.53 (d, J$_{AB}$=13.5 Hz, 1H), 4.15 (def q, J=7 Hz, 2H), 7.20-7.40 (m, 5H).

(S)-(1-Benzyl-3-methylpiperidin-3-yl)methanol (S)-1-Benzyl-3-methylpiperidine-3-carboxylic acid ethyl ester (1.64 g, 6.3 mmol) in dry THF (20 ml) was slowly added to a stirred suspension of LiAlH₄ (0.71 g, 18.8 mmol) in dry THF (20 ml) under nitrogen atmosphere. After the addition the mixture was refluxed for 1.5 h. The solution was cooled with an ice bath, stirred vigorously and 2.5 M NaOH was added carefully drop by drop until no reaction occurred and a white precipitate was formed. The solvent was decanted and the solid washed with EtOAc (2×20 ml). The combined organic phases were dried, filtered and evaporated to dryness to give 1.29 g of the alcohol product as a white powder.
¹H NMR (CDCl₃): δ 0.74 (s, 3H), 1.20-2.15 (m, 6H), 2.78 (m, 2H), 3.45 (s, 2H), 3.56 (d, J$_{AB}$=10.4 Hz, 1H), 3.61 (d, J$_{AB}$=10.4 Hz, 1H), 5.05 (br s, 1H), 7.23-7.40 (m, 5H).

(S)-1-Benzyl-3-methyl-3-[2-(tetrahydropyran-2-yloxy)ethoxymethyl]piperidine (S)-(1-Benzyl-3-methylpiperidin-3-yl)methanol (1.29 g, 5.9 mmol) and tetrabutylammonium bromide (0.19 g, 0.59 mmol) were stirred in 50% NaOH (40 ml) for 15 min. The mixture was then heated to 60° C. and 2-(2-bromoethoxy)tetrahydropyran (2.7 ml, 17.7 mmol) was slowly added (2 h) from a dropping funnel. Stirring was then continued for 4 h at 60° C. Water (40 ml) and brine (20 ml) were added to the cooled mixture, which was extracted with toluene (3×50 ml). The combined extracts were washed twice with water and brine, dried, filtered and evaporated to give 3.0 g of the crude product mixture, which was subjected to flash chromatography on silica. Elution with heptane/EtOAc (80:20) gave 1.14 g of the title compound as a colorless oil.
¹H NMR (CDCl₃): δ 0.95 (s, 3H), 1.16 (m, 1H), 1.45-2.40 (m, 13H), 3.25-3.62 (m, 8H), 3.78-3.92 (m, 2H), 4.66 (m, 1H), 7.20-7.36 (m, 5H). The ¹³C NMR spectrum showed several signals duplicated (mixture of THP diastereomers).

(S)-3-Methyl-3-[2-(tetrahydropyran-2-yloxy)ethoxymethyl]piperidine (S)-1-Benzyl-3-methyl-3-[2-(tetrahydropyran-2-yloxy)ethoxymethyl]piperidine (1.14 g, 3.3 mmol) in MeOH (11 ml) was added to a suspension of Pd/C (0.23 g) in MeOH (11 ml), followed by ammonium formate (1.03 g, 16.4 mmol). The mixture was refluxed for 2 h, after which it was cooled and filtered through Celite. The catalyst was washed with DCM and the combined organic phases were evaporated to dryness. To the residue was added brine (15 ml) and the solution was extracted with EtOAc (3×30 ml). The extracts were combined, dried, filtered and evaporated to yield 0.71 g of the debenzylated product.
¹H NMR (CDCl₃): δ 0.93 (s, 3H), 1.22-1.90 (m, 11H), 2.51 (d, J$_{AB}$=10.4 Hz, 1H), 2.74 (d, J$_{AB}$=10.4 Hz, 1H), 2.75 (m, 2H), 3.26 (d, J$_{AB}$=9.2 Hz, 1H), 3.33 (d, J$_{AB}$=9.2 Hz, 1H), 3.51 (dt, 1H), 3.62 (m, 3H), 3.80-3.95 (m, 2H), 4.67 (m, 1H). The ¹³C NMR spectrum showed several signals duplicated (mixture of THP diastereomers).

1-((S)-7-Fluoro-2,3-dihydrobenzo[1,4]dioxin-2-ylmethyl)-3-methyl-3-[(S)-2-(tetrahydropyran-2-yloxy)ethoxymethyl]piperidine (S)-3-Methyl-3-[2-(tetrahydropyran-2-yloxy)ethoxymethyl]piperidine (100 mg, 0.39 mmol), methanesulfonic acid (R)-(7-fluoro-2,3-dihydrobenzo[1,4]dioxin-2-yl)methyl ester (102 mg, 0.39 mmol), K₂CO₃ (59 mg, 0.43 mmol) and KI (3 mg) were refluxed in dry DMF (3 ml) for 5 h. Water was added to the cooled mixture, followed by extraction with EtOAc (3×15 ml). The extracts were washed several times with water and finally with brine. After drying and filtering, the solvent was evaporated to give 143 mg of the crude product. This was chromatographed on silica (heptane/EtOAc, 70:30) to give 39 mg of the title compound as a colorless oil.
¹H NMR (CDCl₃): δ 0.96 (s, 3H), 1.10-1.90 (m, 10H), 2.15-2.60 (m, 6H), 3.28 (d, J$_{AB}$=8.8 Hz, 1H), 3.34 (d, J$_{AB}$=8.8 Hz, 1H), 3.49 (m, 1H), 3.60 (m, 3H), 3.75-3.95 (m, 3H), 4.23 (m, 1H), 4.30 (m, 1H), 4.65 (t, J=3.6 Hz, 1H), 6.52 (ddd, J=8.4, 8.4 and 3.2 Hz, 1H), 6.58 (dd, J=9.2 and 3.2 Hz, 1H), 6.77 (dd, J=8.4 and 5.2 Hz, 1H).

2-[(S)-1-((S)-7-Fluoro-2,3-dihydrobenzo[1,4]dioxin-2-ylmethyl)-3-methylpiperidin-3-yl-methoxy]ethanol The compound obtained above (39 mg, 0.09 mmol) was stirred in 1 M HCl (0.5 ml) at RT for 2 h. Water (5 ml) was added and the mixture was washed with toluene (5×5 ml). The aqueous layer was then made basic (pH 10) with aq Na₂CO₃ and extracted with EtOAc (4×5 ml). Drying, filtering and evaporation of the solvent yielded 18 mg of the title compound as a colorless oil.
¹H NMR (CDCl₃): δ 0.96 (s, 3H), 1.10-1.65 (m, 4H), 2.05-2.70 (m, 7H), 3.27 (d, J$_{AB}$=8.8 Hz, 1H), 3.46 (d, J$_{AB}$=8.8 Hz, 1H), 3.54 (m, 2H), 3.71 (m, 2H), 3.97 (m, 1H), 4.28 (m, 2H), 6.53 (ddd, J=8.4, 8.4 and 2.8 Hz, 1H), 6.60 (dd, J=9.2 and 3.2 Hz, 1H), 6.79 (dd, J=8.8 and 5.2 Hz, 1H).

Example 98

1-(2,3-Dihydrobenzo[1,4]dioxin-2-ylmethyl)-3-fluoro-piperidine-3-carboxylic acid ethyl ester To a cold (−78° C.) solution of 1-(2,3-dihydrobenzo[1,4]dioxin-2-ylmethyl)piperidine-3-carboxylic acid ethyl ester (300 mg, 0.98 mmol) was added 2 M LDA (0.59 ml, 1.08 mmol). The mixture was stirred for 15 minutes. N-fluorobenzenesulfonimide (341 mg, 1.08 mmol) was added and the mixture was stirred for 20 min. The reaction was quenched with sat. NH₄Cl solution. The solvent was evaporated and the remaining aqueous mixture was extracted two times with EtOAc. The organic layers were pooled, dried, concentrated and absorbed on silica. Flash chromatography (heptane/EtOAc) gave 160 of the title compound as a mixture of diastereomers.
¹H NMR (CDCl₃): δ 1.29-1.33 (m, 3H), 1.62-1.71 (m, 1H), 1.84-2.02 (m, 3H), 2.36-2.49 (m, 1H), 2.64-3.08 (m, 5H), 3.94-4.04 (m, 1H), 4.19-4.36 (m, 4H), 6.78-6.93 (m, 4H).

Example 99

[1-(2,3-Dihydrobenzo[1,4]dioxin-2-ylmethyl)-3-fluoro-piperidin-3-yl]methanol 1-(2,3-Dihydrobenzo[1,4]dioxin-2-ylmethyl)-3-fluoro-piperidine-3-carboxylic acid methyl ester (145 mg, 0.45 mmol) was dissolved in dry THF (4 ml), cooled to −20° C. and treated with LiAlH₄ (34 mg, 0.90 mmol) for 3 h. Water (1 ml), 1 M NaOH (1 ml) and again water (1 ml) was added. The mixture was filtrated, concentrated and extracted with DCM three times. The organic layers were pooled and purified by flash chromatography (gradient of DCM/MeOH) to give 103 mg of the title compound.

¹H NMR (CDCl₃): δ 1.56-1.89 (m, 5H), 2.05 (s, br, 1H), 2.45-2.83 (m, 6H), 3.65-3.80 (m, 2H), 3.95-4.05 (m, 1H), 4.27-4.36 (m, 2H), 6.81-6.96 (m, 4H).

Example 100

(S)-1-[(S)-1-(2,3-Dihydro-benzo[1,4]dioxin-2-yl)methyl]-3-methyl-piperidine-3-carboxylic acid ethyl ester 1-[5-Fluoro-2-((R)-1-(oxiranylmethoxy)-phenyl]-ethanone A mixture of 5'-fluoro-2'-hydroxyacetophenone (2.04 g, 13.25 mmol), (2R)-(–)-glycidyl tosylate (2.75 g, 12.05 mmol), potassium carbonate (2.16 g, 15.66 mmol) and N,N-dimethyl formamide (20 ml) was heated to 60° C. After 6 hours the reaction mixture was cooled down, water (20 ml) and ethyl acetate (20 ml) were added and the layers were separated. Organic phase was recovered and water layer was extracted twice with ethyl acetate. Organic phase and ethyl acetate extracts were combined and washed twice with water and evaporated to dryness. The crude product was crystallized from 2-propanol to yield 1.91 g (76%) of the pure title compound.
¹H NMR (CDCl₃): δ 2.65 (s, 3H), 2.75-2.77 (m, 1H), 2.93-2.95 (t, 1H), 3.37-3.41 (m, 1H), 3.95-4.00 (m, 1H), 4.35-4.39 (m, 1H), 6.91-6.94 (m, 1H), 7.12-7.17 (m, 1H), 7.44-7.47 (m, 1H).

Toluene-4-sulfonic acid (R)-1-(2,3-dihydro-benzo[1,4]dioxin-2-yl)methyl ester

3-Chloroperoxybenzoic acid (4.19 g, 17.00 mmol) was added in small portions to 1-[5-fluoro-2-((R)-1-oxiranylmethoxy)-phenyl]-ethanone (2.55 g, 12.13 mmol) in dichloromethane (13 ml) and the reaction mixture was refluxed for 24 hours. The cooled reaction mixture was washed twice with 10% NaHCO3 solution, once with aq NaOH solution and evaporated to dryness. 2M NaOH (10.9 ml, 21.84 mmol) was added to the evaporation residue and the mixture was heated to reflux for 1 hour. The cooled reaction mixture was extracted with dichloromethane and dichloromethane layer was evaporated to dryness. p-Toluenesulfonyl chloride (2.78 g, 14.56 mmol) was added in small portions to the evaporation residue in pyridine (7.5 ml) and the reaction mixture was stirred at RT. After 4 hours 1M HCl (7.5 ml) was added and the mixture was stirred for 1 hour at RT. The reaction mixture was extracted twice with ethyl acetate and the combined ethyl acetate layers were evaporated to dryness. The crude product was crystallized from 2-propanol to yield 2.58 g (63%) of the pure title compound.
¹H NMR (CDCl₃): δ 2.46 (s, 3H), 3.99-4.04 (m, 1H), 4.17-4.26 (m, 3H), 4.37-4.42 (m, 1H), 6.49-6.56 (m, 2H), 6.75-6.78 (m, 1H), 7.34-7.36 (d, 2H), 7.78-7.80 (d, 2H).

(S)-1-[(S)-1-(2,3-Dihydro-benzo[1,4]dioxin-2-yl)methyl]-3-methyl-piperidine-3-carboxylic acid ethyl ester A mixture of (S)-ethyl-3-methylpiperidine-3-carboxylate (7.23 g, 42.2 mmol), Toluene-4-sulfonic acid (R)-1-(2,3-dihydro-benzo[1,4]dioxin-2-yl)methyl ester (15.0 g, 44.3 mmol), potassium carbonate (6.42 g, 46.4 mmol) and N,N-dimethyl formamide (50 ml) was heated to 120° C. After 4 hours the reaction mixture was cooled down, water (35 ml) was added and the mixture was extracted twice with ethyl acetate. The combined ethyl acetate layers were evaporated to dryness. Toluene (35 ml) was added to the evaporation residue and the mixture was extracted twice with 1M HCl. The combined acidic water layers were made basic with aq NaOH. The basic water layer was extracted twice with ethyl acetate and the combined ethyl acetate layers were evaporated to dryness to yield 10.8 g (76%) of the title compound.
¹H NMR (CDCl₃): δ 1.13 (s, 4H), 1.22-1.25 (t, 3H), 1.55-1.73 (m, 2H), 2.04-2.20 (m, 3H), 2.49-2.54 (m, 1H), 2.61-2.72 (m, 2H), 3.03-3.06 (d, 1H), 3.93-3.98 (m, 1H), 4.07-4.25 (m, 4H), 6.50-6.60 (m, 2H), 6.76-6.80 (m, 1H).

Example 101

[(S)-1-((S)-7-Fluoro-2,3-dihydro-benzo[1,4]dioxin-2-ylmethyl)-3-methyl-piperidin-3-yl]-methanol (S)-1-[(S)-1-(2,3-Dihydro-benzo[1,4]dioxin-2-yl)methyl]-3-methyl-piperidine-3-carboxylic acid ethyl ester (5.0 g, 14.8 mmol) in tetrahydrofuran (10 ml) was added carefully to lithium aluminum hydride (1.125 g, 29.6 mmol) in tetrahydrofuran (40 ml) and stirred at RT for 1 hour. 2M NaOH was added to the reaction mixture until the reaction mixture was basic and all excess LAH was destroyed. The mixture was filtered and the filtrate was evaporated to dryness. Toluene (30 ml) was added to the evaporation residue and the mixture was extracted once with 1M HCl. The acidic water layer was washed once with toluene and made basic with aq NaOH. The basic water layer was extracted twice with ethyl acetate and the combined ethyl acetate layers were evaporated to dryness and dried in vacuum 50° C. to yield 3.02 g (69%) of the title compound.
¹H NMR (CDCl₃): δ 0.82 (s, 3H), 1.20-1.28 (m, 1H), 1.58-1.64 (m, 2H), 1.94-2.04 (m, 1H), 2.14-2.22 (m, 2H), 2.48-2.53 (m, 1H), 2.60-2.81 (m, 3H), 3.59 (s, 2H), 3.92-3.97 (m, 1H), 4.23-4.34 (m, 2H), 6.51-6.56 (m, 1H), 6.60-6.63 (m, 1H), 6.77-6.80 (m, 1H).

Example 102

(S)-1-((S)-7-Fluoro-2,3-dihydro-benzo[1,4]dioxin-2-ylmethyl)-3-methoxymethyl-3-methyl-piperidine

[(S)-1-((S)-7-Fluoro-2,3-dihydro-benzo[1,4]dioxin-2-ylmethyl)-3-methyl-piperidin-3-yl]-methanol (2.5 g, 8.5 mmol) in tetrahydrofuran (10 ml) was added slowly to a mixture of sodium hydride, 60% in oil (1.354 g, 33.9 mmol) and tetrahydrofuran (15 ml). The reaction mixture was heated at 60° C. for 2 hours after the mixture was cooled down and iodomethane (0.685 ml, 11.0 mmol) in tetrahydrofuran (3 ml) was added. The mixture was stirred at RT for 1 hour, water (25 ml) was added carefully and the mixture was extracted twice with ethyl acetate. The combined ethyl acetate layers were evaporated to dryness. Ethyl acetate (20 ml) was added to the evaporation residue and was made acidic with aq HCl. The layers were separated and the water layer was made basic with aq NaOH and extracted twice with ethyl acetate. The combined ethyl acetate layers were evaporated to dryness to yield 2.34 g (89%) of the title compound.
¹H NMR (DMSO): δ 0.89 (s, 3H), 1.07-1.11 (m, 1H), 1.32-1.39 (m, 1H), 1.49-1.52 (m, 2H), 2.11-2.14 (m, 1H), 2.25-2.32 (m, 2H), 2.43-2.52 (m, 3H), 3.14-3.19 (d, 2H), 3.23 (s, 3H), 3.92-3.97 (m, 1H), 4.27-4.31 (m, 2H), 6.62-6.67 (m, 1H), 6.71-6.75 (m, 1H), 6.85-6.88 (m, 1H).

Example 103

(S)-1-((S)-7-Fluoro-2,3-dihydro-benzo[1,4]dioxin-2-ylmethyl)-3-methoxymethyl-3-methyl-piperidine-.HCl Hydrochloride salt was made by using ~10% 2-Propanol/HCl solution (80 ml) which was added slowly to a (S)-1-((S)-7-fluoro-2,3-dihydro-benzo[1,4]dioxin-2-ylmethyl)-3-methoxymethyl-3-methyl-piperidine (11.2 g, 36.2 mmol) in 2-propanol (30 ml). The title product was crystallized from 2-propanol to yield 7.7 g (62%) of the pure title compound. The filtrate was recovered and recrystallized to yield 2.7 g (22%) of the pure title compound (total yield 84%).

$^1$H NMR (DMSO): δ 0.91 & 1.19 (s, 3H), 1.26-1.35 (m, 2H), 1.45-1.75 (m, 2H), 1.90-1.96 (m, 1H), 2.77-3.02 (m, 2H), 3.09-3.15 (m, 1H), 3.22-3.51 (m, 7H), 3.59-3.72 (m, 1H), 4.03-4.07 (m, 1H), 4.30-4.34 (m, 1H), 5.00-5.04 & 5.14-5.18 (m, 1H), 6.72-6.77 (m, 1H), 6.81-6.85 (m, 1H), 6.92-6.96 (m, 1H), 10.29 & 10.80 (bs, 1H).

Example 104

(S)-1-[(S)-1-(2,3-Dihydro-benzo[1,4]-dioxin-2-yl)methyl]-3-methoxymethyl-3-methyl-piperidine A mixture of {(S)-1-[(S)-1-(2,3-Dihydro-benzo[1,4]dioxin-2-yl)methyl]-3-methyl-piperidin-3-yl}methanol (134 mg, 0.48 mmol), tetrabutylammonium bromide (0.031 mg, 0.10 mmol) and 50% NaOH solution (2 ml) in toluene (2 ml) was stirred at room temperature for 15 min. Methyl iodide (0.24 ml, 3.86 mmol) was added drop wise and the mixture was stirred for 6 h 45 min. Saturated NaCl, water and EtOAc were added and the phases were separated. The aqueous phase was extracted twice with EtOAc and combined organic phases were washed with water and saturated NaCl. The organic phase was dried (Na$_2$SO$_4$), filtered and evaporated to dryness. The crude product was purified with flash chromatography using gradient of heptane and EtOAc as eluent to give 27 mg of the title compound.

$^1$H NMR (CDCl$_3$): δ 0.95 (s, 3H), 1.10-1.30 (m, 2H), 1.35-1.45. (m, 1H), 1.56-1.64 (m, 1H), 2.15-2.41 (m, 3H), 2.44-2.54 (m, 2H), 2.56-2.64 (m, 1H), 3.15-3.26 (m, 2H), 3.33 (s, 3H), 3.94-4.02 (m, 1H), 4.21-4.29 (m, 1H), 4.32-4.38 (m, 1H), 6.79-6.90 (m, 4H).

Example 105

3-{(R*)-1-[(S)-1-(2,3-Dihydro-benzo[1,4]dioxin-2-yl)methyl]-piperidin-3-yl}-phenylamine A mixture of trifluoro-methanesulfonic acid 3-{(R*)-1-[(S)-1-(2,3-dihydro-benzo[1,4]dioxin-2-yl)methyl]-piperidin-3-yl}-phenyl ester (1.039 g, 2.27 mmol), cesium carbonate (1.036 g, 3.18 mmol), palladium acetate (0.015, 0.068 mmol), (R)-(+)-2,2-bis(diphenylphosphino)-1,1-binaphthyl (0.064 g, 0.102 mmol) and benzophenone imine (0.457 ml, 2.73 mmol) in dry tetrahydrofuran (6 ml) was heated in a microwave reactor at 80° C. for 10 hours. The mixture was filtered and evaporated to dryness. The crude product was purified by flash chromatography using a gradient of heptane and EtOAc as eluent. The residue on evaporation was dissolved in dry methanol, sodium acetate (0.54 g, 6.55 mmol) and hydroxylamine hydrochloride (0.36 g, 5.24 mmol) was added and the mixture was stirred at room temperature for 1.5 h. The mixture was evaporated to dryness, dissolved in EtOAc and washed with 1M Na$_2$CO$_3$. The organic layer was dried (Na$_2$SO$_4$), filtered and evaporated to dryness. The crude product was purified by flash chromatography using gradient of heptane and EtOAc as eluent to give 151 mg of the title compound.

$^1$H NMR (CDCl$_3$): δ 1.37-1.50 (m, 1H) 1.64-1.81 (m, 2H), 1.79-1.92 (m, 1H), 2.09-2.22 (m, 2H), 2.56-2.64 (m, 1H), 2.66-2.77 (m, 2H), 2.89-2.97 (m, 1H), 3.10-3.07 (m, 1H), 3.61 (s (broad), 2H), 3.96-4.03 (m, 1H), 4.27-4.35 (m, 2H), 6.51-6.58 (m, 2H), 6.61-6.65 (m, 1H), 6.76-6.90 (m, 4H), 7.09 (t, 1H).

Example 106

(R*)-3-{1-[(S)-1-(2,3-Dihydrobenzo[1,4]dioxin-2-yl)methyl]piperidin-3-yl}phenol oxalate To a hot solution (70° C.) of (R*)-3-{1-[(S)-1-(2,3-dihydrobenzo[1,4]dioxin-2-yl)methyl]piperidin-3-yl}phenol (10 g, 30.7 mmol) in dry isopropyl alcohol (75 ml) a heated solution (70° C.) of oxalic acid (2.77 g, 30.7 mmol) in dry isopropyl alcohol (25 ml) was added. Precipitation was occurred and the mixture was heated up to 80° C. After one hour stirring it was slowly cooled to room temperature and stirred over night. The mixture was cooled to 0° C., stirred for two hours and the precipitate was filtered to give 11.76 g of the desired salt.

$^1$H NMR (MeOD): δ 1.73-1.82 (m, 1H), 1.93-2.10 (m, 3H), 3.05-3.24 (m, 3H), 3.30-3.48 (m, 2H), 3.66-3.73 (m, 2H), 3.99-4.05 (m, 1H), 4.26-4.32 (m, 1H), 4.78-4.83 (m, 1H), 6.67-6.77 (m, 3H), 6.82-6.91 (m, 4H), 7.16 (t, 1H).

Example 107

(S)-2-[(R*)-3-(3-Hydroxy-phenyl)-piperidin-1-ylmethyl]-2,3-dihydro-benzo[1,4]dioxin-5-ol (S)-4-((2,6-Dimethoxyphenoxy)methyl)-2,2-dimethyl-1,3-dioxolane A mixture of 2,6-dimethoxyphenol (2.00 g, 12.97 mmol), (R)-(−)-2,2-dimethyl-1,3-dioxalan-4-ylmethyl p-toluenesulfonate (3.72 g, 12.97 mmol) and NaH (60% dispersion in mineral oil, 0.86 g, 21.50 mmol) in N,N-dimethylformamide (55 ml) were stirred at +25° C. for 30 min, and at +150° C. for 4.5 h. The reaction mixture was cooled down, water (50 ml) and diethyl ether (40 ml) were added and the layers were separated. Organic phase was recovered and water layer was extracted twice with diethyl ether. Organic phase and diethyl ether extracts were combined and washed five times with water and saturated sodium chloride solution. The combined organic phase was dried (Na$_2$SO$_4$), filtered and evaporated to dryness to give 2.91 g of the title compound.

$^1$H NMR (CDCl$_3$): δ 1.38 (s, 3H), 1.43 (s, 3H), 3.82-3.90 (m, 1H), 3.85 (s, 6H), 4.02-4.05 (m, 1H), 4.12-4.18 (m, 2H), 4.42-4.48 (m, 1H), 6.56-6.58 (d, 2H), 6.97-7.02 (tr, 1H).

(R)-3-(2,6-Dimethoxyphenoxy)propane-1,2-diol

A mixture of (S)-4-((2,6-dimethoxyphenoxy)methyl)-2,2-dimethyl-1,3-dioxolane (2.91 g, 10.85 mmol) and Amberlyst 15® (1.60 g) in methanol (30 ml) were stirred for 5 d. The mixture was filtered and evaporated to dryness to give 2.26 g of the title compound.

$^1$H NMR (CDCl$_3$): δ 3.70-3.75 (m, 2H), 3.87 (s, 6H), 3.94-3.96 (m, 2H), 4.23-4.25 (m, 1H), 6.58-6.60 (d, 2H), 7.00-7.04 (tr, 1H).

Methanesulfonic acid (S)-3-(2,6-dimethoxy-phenoxy)-2-methanesulfonyloxy-propyl ester (R)-3-(2,6-Dimethoxyphenoxy)propane-1,2-diol (2.26 g, 9.90 mmol) in dichloromethane (20 ml) was cooled to 0° C. and stirred under nitrogen atmosphere. Triethyl amine (2.94 g, 29.00 mmol) was added in 15 min. Methanesulfonic acid chloride (2.61 g, 21.80 mmol) was added, and the mixture was stirred at +25° C. for 3 h. Dichloromethane (20 ml) and 1 M NaHSO$_4$ solution (10 ml) were added and the layers were separated. Organic layer was washed with 1 M NaHSO$_4$ solution (10 ml), water (10 ml) and saturated sodium chloride solution (10 ml), dried (Na$_2$SO$_4$), filtered and evaporated to dryness to give 3.08 g of the title compound.

$^1$H NMR (CDCl$_3$): δ 3.10 (s, 3H), 3.18 (s, 3H), 4.20-4.22 (m, 2H), 3.85 (s, 6H), 4.56-4.60 (m, 1H), 4.66-4.69 (m, 1H), 5.14-5.16 (m, 1H), 6.56-6.59 (d, 2H), 7.01-7.05 (tr, 1H).

Methanesulfonic acid (S)-3-(2,6-dihydroxy-phenoxy)-2-methanesulfonyloxy-propyl ester Methanesulfonic acid (S)-3-(2,6-dimethoxy-phenoxy)-2-methanesulfonyloxy-propyl ester (3.08 g, 8.00 mmol) in) in dichloromethane (40 ml) was cooled to 0° C. and stirred under nitrogen atmosphere. Boron tribromide (1 M solution in dichloromethane, 18 ml, 18 mmol) was added in 15 min. The mixture was stirred at +25° C. for 4 h, and poured on mixture of ice (10 g) and water (15 ml), and the layers were separated. Organic phase was recovered and water layer was extracted twice with dichloromethane (15 ml). Organic phase and dichloromethane extracts were combined and washed with water (15 ml) and saturated sodium chloride solution (15 ml). The combined organic phase was dried (Na$_2$SO$_4$), filtered and evaporated to dryness to give 2.53 g of the title compound.

$^1$H NMR (DMSO): δ 3.24 (s, 3H), 3.28 (s, 3H), 4.12-4.14 (m, 2H), 4.58-4.60 (m, 2H), 5.14-5.19 (m, 1H), 6.31-6.33 (d, 2H), 6.67-6.71 (tr, 1H), 9.20 (s, 3H).

Methanesulfonic acid (R)-5-hydroxy-2,3-dihydro-benzo[1,4]dioxin-2-ylmethyl ester A mixture of methanesulfonic acid (S)-3-(2,6-dihydroxy-phenoxy)-2-methanesulfonyloxy-propyl ester (253 g, 7.10 mmol) and potassium carbonate (1.14 g, 8.30 mmol) in acetone (30 ml) was refluxed under nitrogen atmosphere for 3.5 h. The reaction mixture was cooled down, filtered and evaporated to dryness. The crude product was purified with flash chromatography using dichloromethane and ethyl acetate as eluents to give 0.75 g of the title compound.

$^1$H NMR (DMSO): δ 3.24 (s, 3H), 3.99-4.03 (m, 1H), 4.37-4.42 (m, 2H), 4.47-4.49 (m, 2H), 6.35-6.41 (m, 2H), 6.61-6.65 (tr, 1H), 9.22 (s, 1H).

Methanesulfonic acid (R)-5-benzyloxy-2,3-dihydro-benzo[1,4]dioxin-2-ylmethyl ester A mixture of methanesulfonic acid (R)-5-hydroxy-2,3-dihydro-benzo[1,4]dioxin-2-ylmethyl ester (0.6 g, 1.69 mmol), benzyl bromide (0.4 g, 2.30 mmol) and potassium carbonate (1.14 g, 8.30 mmol) in acetone (30 ml) was refluxed under nitrogen atmosphere for 5 h. The crude product was crystallized from 2-propanol to yield 8.8 mg of the pure title compound.

$^1$H NMR (CDCl$_3$): δ 3.06 (s, 3H), 4.11-4.18 (m, 1H), 4.35-4.38 (dd, 1H), 4.43-4.46 (m, 2H), 4.47-4.49 (m, 1H), 5.12 (s, 1H), 6.54-6.56 (d, 2H), 6.73-6.77 (tr, 1H), 7.30-7.44 (m, 5H).

3-[(R*)-1-((S)-5-Benzyloxy-2,3-dihydro-benzo[1,4]dioxin-2-ylmethyl)-piperidin-3-yl]-phenol A mixture of hydrochloride salt of (R*)-3-(piperidin-3-yl)-phenol (240 mg, 1.12 mmol) and sodium bicarbonate in N,N-dimethylformamide (3 ml) were stirred at +120° C. under nitrogen atmosphere. To this mixture, a mixture of methanesulfonic acid (R)-5-benzyloxy-2,3-dihydro-benzo[1,4]dioxin-2-ylmethyl ester (390 mg, 1.11 mmol) in N,N-dimethylformamide (3 ml) was added, and stirred at +130° C. for 3.5 h. The reaction mixture was cooled down, water (20 ml) and ethyl acetate (15 ml) were added and the layers were separated. Organic phase was recovered and water layer was extracted twice with ethyl acetate. Organic phase and ethyl acetate extracts were combined and washed five times with water and saturated sodium chloride solution. The combined organic phase was dried (Na$_2$SO$_4$), filtered and evaporated to dryness. The crude product was purified with flash chromatography using heptane and ethyl acetate as eluents to give 160 mg of the title compound.

$^1$H NMR (CDCl$_3$): δ 1.42-1.46 (m, 1H), 1.72-1.74 (m, 1H), 1.89-1.93 (m, 1H), 2.14-2.19 (q, 2H), 2.63-2.82 (m, 3H), 2.91-2.94 (d, 1H), 3.03-3.06 (d, 1H), 4.02-4.06 (m, 1H), 4.31-4.34 (q, 1H), 4.38-4.41 (m, 1H), 5.29 (s, 1H), 6.45-6.53 (m, 2H), 6.66-6.72 (m, 3H), 6.79-6.81 (d, 1H), 7.14-7.18 (tr, 3H), 7.26-7.44 (m, 5H).

(S)-2-[(R*)-3-(3-Hydroxy-phenyl)-piperidin-1-ylmethyl]-2,3-dihydro-benzo[1,4]dioxin-5-ol A mixture of 3-[(R*)-1-((S)-5-benzyloxy-2,3-dihydro-benzo[1,4]dioxin-2-ylmethyl)-piperidin-3-yl]-phenol (84 mg, 0.19 mmol) and palladium-on-carbon (60 mg) in ethyl acetate (10 ml) were stirred and hydrogenated for 6 h. The reaction mixture was filtered and washed with ethyl acetate (10 ml), and evaporated to dryness. The crude product was purified with flash chromatography using dichloromethane and methanol as eluents to give 65 mg of the title compound.

$^1$H NMR (CDCl$_3$): δ 1.40-1.49 (m, 1H), 1.76-1.77 (m, 1H), 1.90-1.93 (m, 1H), 2.13-2.23 (m, 2H), 2.60-2.75 (m, 2H), 2.97-3.00 (d, 1H), 3.11-3.13 (d, 1H), 3.97-4.02 (m, 1H), 4.32-4.39 (m, 2H), 6.34-6.41 (d, 1H), 6.50-6.52 (d, 1H), 6.67-6.72 (m, 5H), 6.77-6.79 (d, 1H), 7.15-7.19 (tr, 1H).

Example 108

1-[(S)-1-(2,3-Dihydro-benzo[1,4]dioxin-2-yl)methyl]-3-(2-methoxy-phenyl)-pyrrolidine

(S)-1-(2,3-Dihydro-benzo[1,4]dioxin-2-yl)-methanol (R)-2,3-Dihydro-benzo[1,4]dioxine-2-carboxylic acid (27.9 mmol, 5.02 g) was dissolved in dry THF (30 ml). LiAlH$_4$ (56.9 mmol, 2.16 g) was added. The mixture was refluxed for 70 minutes. After cooling, the reaction was quenched with water and 1 M NaOH. The mixture was filtrated through Celite and evaporated to dryness. This gave 4.3 g of the title compound.

$^1$H NMR (CDCl$_3$): δ 3.81-3.95 (m, 2H), 4.09-4.16 (m, 1H), 4.24-4.32 (m, 2H), 6.83-6.93 (m, 4H)

Toluene-4-sulfonic acid (R)-1-(2,3-dihydro-benzo[1,4]dioxin-2-yl)methyl ester (S)-1-(2,3-Dihydro-benzo[1,4]dioxin-2-yl)-methanol (24.1 mmol, 4.0 g), triethylamine (24.3 mmol, 3.42 ml) and DCM (50 ml) were mixed and stirred on an ice-bath. p-Toluenesulfonyl chloride (24.3 mmol, 4.63 g) in DCM (10 ml) was added dropwise. The mixture was stirred over night at r.t and washed with water. The organic phase was evaporated to dryness. The crude product was dissolved in THF (10 ml) and treated with 1 M NaOH (2 ml) for 10 minutes. Water (100 ml) was added. The aqueous solution was extracted with EtOAc, the organic phase was dried and evaporated to dryness. Flash chromatography, using heptane/EtOAc as eluent gave 7.66 g of the desired product.

$^1$H NMR (DMSO): δ 2.42 (s, 3H), 3.91-3.99 (m, 1H), 4.17-4.29 (m, 2H), 4.31-4.38 (m, 1H), 4.40-4.46 (m, 1H), 6.75-6.86 (m, 4H), 7.48 (d, 2H), 7.80 (d, 2H)

1-[(S)-1-(2,3-Dihydro-benzo[1,4]dioxin-2-yl)methyl]-3-(2-methoxy-phenyl)-pyrrolidine Toluene-4-sulfonic acid (R)-1-(2,3-dihydro-benzo[1,4]dioxin-2-yl)methyl ester (0.156 mmol), 3-(2-methoxyphenyl)pyrrolidine.HCl (1.55 mmol, 32 mg), K$_2$CO$_3$ (0.342 mmol, 47 mg) and acetonitrile (1 ml) were mixed and heated in a microwave reactor at 120° C. for 2.5 h. The reaction mixture was filtrated and the solution was absorbed on silica. Flash chromatography, using a gradient of heptane/EtOAc as eluent, gave 20 mg g of the title compound.

$^1$H NMR (MeOD): δ 1.86-1.97 (m, 1H), 2.55-2.56 (m, 1H), 2.54-2.65 (m, 1H), 2.74-2.89 (m, 3H), 2.93-3.06 (m, 1H), 3.11-3.23 (m, 1H), 3.67-3.77 (m, 1H), 3.93-4.00 (m, 1H), 4.27-4.37 (m, 2H), 6.77-6.94 (m, 5H), 7.14-7.20 (m, 1H), 7.24-7.29 (m, 1H)

Example 109

(S)-1-[(S)-1-(2,3-Dihydro-benzo[1,4]dioxin-2-yl)methyl]-3-(2-fluoro-ethoxymethyl)-3-methyl-piperidine.HCl 2-{(S)-1-[(S)-1-(2,3-Dihydro-benzo[1,4]dioxin-2-yl)methyl]-3-methyl-piperidin-3-ylmethoxy}-ethanol (15.56 mmol, 5.0 g) was dissolved in DCM (30 ml) under nitrogen protection. 4 A molecular sieves were added. The mixture was cooled to 5° C. and stirred for 5 minutes. Diethylaminosulfur trifluoride (23.33 mmol, 3.06 ml) was added. The mixture was stirred at r.t for 4 h. 1 M Na$_2$CO$_3$ (50 ml) was added. The phases were separated, the organic phase was evaporated to dryness. Flash chromatography gave 1.04 g desired product. This crude product was treated with HCl/EtOH and evaporated to dryness. The title compound was crystallised (1.02 g) from diethylether.

$^1$H NMR (DMSO): δ 0.94 (s, 1.5H), 1.19 (s, 1.5H), 1.27-1.39 (m, 1H), 1.40-1.54 (m, 0.5H), 1.61-2.00 (m, 2.5H), 2.78-3.06 (m, 2H), 3.20-3.29 (m, 3H), 3.40-3.88 (m, 5H), 3.98-4.12 (m, 1H), 4.27-4.38 (m, 1H), 4.46-4.69 (m, 2H), 4.89-5.03 (m, 1H), 6.80-6.96 (m, 4H), 9.78 (s, br, 0.5H), 10.34 (s, br, 0.5H)

Example 110

(R*)-1-[(S)-1-(2,3-Dihydro-benzo[1,4]dioxin-2-yl)methyl]-3-(3-fluoromethoxy-phenyl)-piperidine

(R)-2,3-Dihydro-benzo[1,4]dioxin-2-yl-[(R*)-3-(3-fluoromethoxy-phenyl)-piperidin-1-yl]-methanone Bromofluoromethane-pyridinium adduct (excess) was condensed in a vial. (R)-2,3-Dihydro-benzo[1,4]dioxin-2-yl-[(R*)-3-(3-hydroxy-phenyl)-piperidin-1-yl]-methanone (1.84 mmol, 0.623 g) and K$_2$CO$_3$ (3.67 mmol, 0.507 mmol) were added and the tube was sealed. Acetonitril (5 ml) was added. The reaction was stirred at 120° C. for 60 min. After cooling, the mixture was evaporated to dryness, taken up in DCM and washed with water. The organic phase was evaporated to dryness. 0.680 g of the title compound was obtained.

$^1$H NMR (MeOD): δ 1.75-1.98 (m, 3H), 2.63-2.93 (m, 2H), 3.14-3.28 (m, 2H), 4.11-4.31 (m, 2H), 4.37-4.46 (m, 1H), 4.51-4.60 (m, 1H), 5.07-5.13 (m, 1H), 5.73 (d, 2H), 6.78-7.09 (m, 7H), 7.29 (t, 1H)

(R*)-1-[(S)-1-(2,3-Dihydro-benzo[1,4]dioxin-2-yl)methyl]-3-(3-fluoromethoxy-phenyl)-piperidine (R)-2,3-Dihydro-benzo[1,4]dioxin-2-yl-[(R*)-3-(3-fluoromethoxy-phenyl)-piperidin-1-yl]-methanone (0.13 mmol, 50 mg) was treated with BH$_3$ THF according to the above general procedure. Flash chromatography gave the title compound.

$^1$H NMR (CDCl$_3$): δ 1.37-1.49 (m, 1H), 1.59-1.83 (m, 2H), 1.84-1.96 (m, 1H), 2.11-2.24 (m, 2H), 2.56-2.63 (m, 1H), 2.67-2.73 (m, 1H), 2.77-2.86 (m, 1H), 2.90-2.98 (m, 1H), 3.01-3.07 (m, 1H), 3.94-4.04 (m, 1H), 4.28-4.36 (m, 2H), 5.71 (d, 2H), 6.78-7.04 (m, 7H), 7.22-7.31 (m, 1H)

Example 111

1-(2,3-Dihydro-benzo[1,4]dioxin-2-ylmethyl)-pyrrolidine-3-carboxylic acid methyl ester

1-(2,3-Dihydro-benzo[1,4]dioxin-2-ylmethyl)-5-oxo-pyrrolidine-3-carboxylic acid methyl ester The title compound was prepared using 200 mg (1.21 mmol) of 2,3-dihydro-benzo[1,4]dioxin-2-ylmethylamine and 0.17 mL (1.21 mmol) of dimethyl itaconate according to the procedure for substituted pyrrolidines described in *J. Org. Chem.* 26 (1961) 1519-1524. Purification by column chromatography (silica gel, heptane/ethyl acetate, 1:2) afforded the pure product.

$^1$H NMR (MeOD, c6055): 2.62-2.73 (m, 2H), 3.33-3.39 (m, 1H), 3.52-3.64 (m, 2H), 3.66 (s, 1.5H), 3.74 (s, 1.5H), 3.76-3.96 (m, 3H), 4.26 (dm, 1H), 4.34-4.38 (m, 1H), 6.78-6.86 (m, 4H).

1-(2,3-Dihydro-benzo[1,4]dioxin-2-ylmethyl)-pyrrolidine-3-carboxylic acid methyl ester A solution containing 300 mg (1.03 mmol) of 1-(2,3-dihydro-benzo[1,4]dioxin-2-ylmethyl)-5-oxo-pyrrolidine-3-carboxylic acid methyl ester in dry tetrahydrofuran (4 mL) was cooled to 0° C. under nitrogen. After adding 4 mL of 1M BH$_3$-tetrahydrofuran solution (4.12 mmol), the reaction mixture was allowed to warm to room temperature and it was stirred for 5 h. Decomposition of the boron complexes was effected by addition of 3 mL of methanol and 3 mL of 6 M HCl-solution followed by stirring the mixture at 40° C. for ½ h. Tetrahydrofuran was evaporated off under vacuum. The residue was dissolved in 50 mL of water and the pH of the solution was adjusted to 10 using 1M Na$_2$CO$_3$ solution. The water phase was extracted with ethyl acetate (3×25 mL), and the combined organic phases were dried over anhydrous sodium sulfate, filtered, and evaporated to dryness. The crude product was purified by column chromatography (silica gel, heptane/ethyl acetate, 7:3).

¹H NMR (MeOD, c6363): 2.02-2.13 (m, 2H), 2.61-3.12 (m, 7H), 3.68 (s, 1.5H), 3.68 (s, 1.5H), 3.91 (dd, 1H), 4.25-4.31 (m, 2H), 6.76-6.85 (m, 4H).

Example 112

[1-(2,3-Dihydro-benzo[1,4]dioxin-2-ylmethyl)-pyrrolidin-3-yl]-methanol

To a solution containing 130 mg (0.45 mmol) of 1-(2,3-dihydro-benzo[1,4]dioxin-2-ylmethyl)-5-oxo-pyrrolidine-3-carboxylic acid methyl ester in dry tetrahydrofuran (4 mL) was added 68 mg (1.79 mmol) of LiAlH$_4$. The reaction mixture was stirred at room temperature for 2½ h, and subsequently refluxed for 2 h. After the reaction mixture was cooled to room temperature, it was quenched with water and 1 M NaOH. The solution was filtered through celite and the filtrate was evaporated to dryness. Purification by column chromatography (silica gel, triethylamine/ethyl acetate, 1:99) afforded the title compound.
¹H NMR (MeOD, c6802): 1.48-1.56 (m, 1H), 1.91-2.01 (m, 1H), 2.31-2.49 (m, 2H), 2.57-2.90 (m, 5H), 3.44-3.53 (m, 2H), 3.94 (dd, 1H), 4.26-4.39 (m, 2H), 6.77-6.85 (m, 4H).

Example 113

2-[1-(2,3-Dihydro-benzo[1,4]dioxin-2-ylmethyl)-pyrrolidin-3-ylmethoxy]-ethanol

To a solution containing 50 mg (0.19 mmol) of [1-(2,3-dihydro-benzo[1,4]dioxin-2-ylmethyl)-pyrrolidin-3-yl]-methanol in dichloromethane (1.5 mL), 1.5 mL of cold aqueous NaOH-solution (50%, w/w) and 6 mg (0.02 mmol) of tert-butylammonium bromide were added at 0° C. The reaction mixture was stirred for ½ h at 0° C. After adding 28 L (0.19 mmol) of tert-butylbromoacetate the stirring was continued for 3 h at 10° C. Subsequent addition of water (10 mL) and dichloromethane (40 mL) was followed by stirring the mixture for additional 10 min at room temperature. The phases were separated, and the organic phase was washed with 5% NaHCO$_3$ (1×20 mL), dried over anhydrous sodium sulfate, filtered, and evaporated to dryness. The crude product was dried under high vacuum and redissolved in dry tetrahydrofuran (4 mL) and reduced with 15 mg (0.40 mmol) of LiAlH$_4$ using the same procedure as above. The crude product was purified by column chromatography (silica gel, methanol/triethylamine/ethyl acetate, 1:1:99).
¹H NMR (MeOD, c6936): 1.49-1.58 (m, 1H), 1.93-2.00 (m, 1H), 2.42-2.90 (m, 7H), 3.38-3.46 (m, 2H), 3.51 (t, 2H), 3.65 (t, 2H), 3.91-3.96 (m, 1H), 4.26-4.32 (m, 2H), 6.77-6.85 (m, 4H).

Example 114

1-(2,3-Dihydro-benzo[1,4]dioxin-2-ylmethyl)-3-methyl-pyrrolidine-3-carboxylic acid methyl ester To a solution containing 80 mg (0.29 mmol) of 1-(2,3-dihydro-benzo[1,4]dioxin-2-ylmethyl)-pyrrolidine-3-carboxylic acid methyl ester in dry tetrahydrofuran (4.5 mL) at −78° C. under nitrogen was added 0.3 mL (0.58 mmol) of lithium diisopropylamine (2.0 M solution in heptane/tetrahydrofuran/ethylbenzene). The reaction mixture was stirred at −78° C. for 1 h and subsequently 0.04 mL (0.58 mmol) of iodomethane was added. The reaction mixture was allowed to warm to room temperature and the stirring was continued for 3 h. The reaction was quenched with 15 mL of saturated aqueous NH$_4$Cl-solution and the tetrahydrofuran was evaporated off under vacuum. Water (50 mL) was added and the pH was adjusted to 10 using 1M Na$_2$CO$_3$. The water phase was extracted with ethyl acetate (3×25 mL), and the combined organic phases were dried over anhydrous sodium sulfate, filtered, and evaporated to dryness, and the residue was dried under high vacuum.
¹H NMR (MeOD, c6744): 1.34 (s, 3H), 1.64-1.71 (m, 1H), 2.37-2.44 (m, 1H), 2.51 (dd, 1H), 2.68-2.83 (m, 4H), 3.17 (dd, 1H), 3.68 (s, 1.5H), 3.69 (s, 1.5H), 3.94 (ddd, 1H), 4.24-4.29 (m, 2H), 6.76-6.85 (m, 4H).

Example 115

[1-(2,3-Dihydro-benzo[1,4]dioxin-2-ylmethyl)-3-methyl-pyrrolidin-3-yl]-methanol

The reduction of 84 mg (0.28 mmol) of 1-(2,3-dihydro-benzo[1,4]dioxin-2-ylmethyl)-3-methyl-pyrrolidine-3-carboxylic acid methyl ester with 20 mg (0.53 mmol) of LiAlH$_4$ was performed using the procedure described above. Purification by column chromatography (silica gel, methanol/triethylamine/dichloromethane, 1:1:99) yielded the desired pure alcohol.
¹H NMR (MeOD, c6807): 1.10 (s, 3H), 1.47-1.53 (m, 1H), 1.69-1.77 (m, 1H), 2.31 (dd, 1H), 2.60-2.80 (m, 5H), 3.36 (AB d, 1H), 3.38 (AB d, 1H), 3.92 (dd, 1H), 4.24-4.29 (m, 2H), 6.73-6.84 (m, 4H).

Example 116

2-[1-(2,3-Dihydro-benzo[1,4]dioxin-2-ylmethyl)-3-methyl-pyrrolidin-3-ylmethoxy]-ethanol 38 mg (0.14 mmol) of [1-(2,3-dihydro-benzo[1,4]dioxin-2-ylmethyl)-3-methyl-pyrrolidin-3-yl]-methanol was treated with 21 μL (0.14 mmol) of tert-butylbromoacetate using the same procedure as described for example 112. Purification by column chromatography (silica gel, triethylamine/ethyl acetate/heptane, 1:10:90) yielded the desired intermediate. The reduction of 30 mg (0.08 mmol) of the intermediate was performed with 6 mg (0.16 mmol) of LiAlH$_4$ using the same procedure as described for example 112. Purification by column chromatography (silica gel, triethylamine/ethyl acetate, 1:99) yielded the desired pure alcohol.
¹H NMR (MeOD): 1.13 (s, 3H), 1.47-1.54 (m, 1H), 1.75-1.82 (m, 1H), 2.34 (dd, 1H), 2.64-2.79 (m, 5H), 3.27 (AB d, 1H), 3.32 (AB d, 1H), 3.52 (t, 1H), 3.52 (t, 1H), 3.66 (t, 2H), 3.67 (t, 1H), 3.93 (dd, 1H), 4.25-4.30 (m, 2H), 6.76-6.85 (m, 4H).

Example 117

1-(2,3-Dihydro-benzo[1,4]dioxin-2-ylmethyl)-3-methoxymethyl-3-methyl-pyrrolidine A solution of 56 mg (0.21 mmol) of [1-(2,3-Dihydro-benzo[1,4]dioxin-2-ylmethyl)-3-methyl-pyrrolidin-3-yl]-methanol in 1.5 ml of tetrahydrofuran was added to a flask containing 58 mg (2.40 mmol) of sodium hydride, previously washed with heptane under argon. The reaction mixture was stirred at 60° C. for 2 h, cooled to 0° C. followed by dropwise addition of a solution containing 16 μl (0.25 mmol) of iodomethane in tetrahydrofuran (0.5 ml). The reaction mixture was allowed to warm to room temperature and the stirring was continued for 1½ h. Water was slowly added and tetrahydrofuran was evaporated off and the water phase was extracted with dichloromethane (3×25 ml). The combined organic phases were dried over anhydrous sodium sulfate, filtered, and evaporated to dryness. Purification by column chromatography (silica gel, ethyl acetate/heptane, 7:13) yielded the desired pure methyl ether.

$^1$H NMR (MeOD, c9843): 1.11 (s, 3H), 1.46-1.53 (m, 1H), 1.69-1.76 (m, 1H), 2.34 (dd, 1H), 2.55-2.74 (m, 5H), 3.16-3.23 (m, 2H), 3.33 (s, 1.5H), 3.34 (s, 1.5H), 3.93 (dd, 1H), 4.21-4.30 (m, 2H), 6.78-6.84 (m, 4H).

Example 118

3-[(R)-1-((S)-7-Nitro-2,3-dihydro-benzo[1,4]dioxin-2-ylmethyl)-piperidin-3-yl]-phenol (S)-2-[(R*)-3-(3-Hydroxy-phenyl)-piperidin-1-ylmethyl]-2,3-dihydro-benzo[1,4]dioxin-5-ol 4-Nitrobenzene-1,2-diol (12.9 mmol, 2.0 g) was dissolved in dry DMF (15 ml). Anhydrous potassium carbonate (15.5 mmol, 2.1 g) was added and reaction mixture was warmed to 50° C. (2R)-(-)-glycidyl tosylate (13.5 mmol, 3.2 g) was dissolved to DMF (2 ml) and added drop wise at 50° C. The reaction mixture was heated to 120° C. for 2 h. After cooling the mixture was quenched with water and filtered. The water layer was extracted twice with ethyl acetate. The organic phases were combined and washed twice with water and saturated sodium chloride solution. The organic phase was dried ($Na_2SO_4$), filtered and evaporated to dryness. This gave 2.1 g of the title compound as a mixture of isomers (20/80). Purification was done by crystallizations ($CHCl_3$ and chlorobenzen) to give 0.6 g of the title compound.

$^1$H NMR (DMSO): δ 3.62-3.71 (m, 2H), 4.14-4.19 (m, 1H), 4.25-4.47 (m, 1H), 4.47-4.50 (m, 1H), 5.13 (t, 1H), 7.10 (d, 1H), 7.12-7.78 (m, 2H).

Methanesulfonic acid (R)-7-nitro-2,3-dihydro-benzo[1,4]dioxin-2-ylmethyl ester (S)-2-[(R*)-3-(3-Hydroxy-phenyl)-piperidin-1-ylmethyl]-2,3-dihydro-benzo[1,4]dioxin-5-ol (2.84 mmol, 0.60 g) was dissolved in dry dichloromethane. Triethylamine (0.43 ml) was added and the mixture was cooled to 0° C. Methanesulfonyl chloride (2.94 mmol, 0.34 g) was added drop wise at 0° C. The mixture was allowed to warm to RT and stirred over night. 1M Hydrogen chloride solution (10 ml) was added. Water phase was extracted twice with DCM and the organic phases were combined. The organic phase was extracted with water and brine and evaporated to dryness. The crude product was purified by crystallization (EtOH) to give 0.48 g of the title compound.

$^1$H NMR ($CDCl_3$): δ 3.11 (s, 3H), 4.19-4.24 (m, 1H), 4.43-4.54 (m, 4H), 6.69 (d, 1H), 7.81-7.84 (m, 2H).

3-[(R)-1-((S)-7-Nitro-2,3-dihydro-benzo[1,4]dioxin-2-ylmethyl)-piperidin-3-yl]-phenol Methanesulfonic acid (R)-7-nitro-2,3-dihydro-benzo[1,4] dioxin-2-ylmethyl ester (0.98 mmol, 0.28 g) was dissolved in the mixture of DMF (2.8 ml) and acetonitrile (2.8 ml). $NaHCO_3$ (2.92 mmol, 0.25 g) and (R*)-3-(piperidin-3-yl) phenol hydrochloride was added. The mixture was refluxed 4 h and after cooling water (15 ml) was added. The water phase was extracted twice with ethyl acetate and washed with water and brine. Evaporation to dryness gave 0.36 g of the crude product. Flash chromatography, using heptane/EtOAc as eluent and crystallisation ($CHCl_3$) gave 83 mg of the desired product.

$^1$H NMR ($CDCl_3$): δ 1.25-1.28 (m, 1H), 1.72-1.78 (m, 2H), 1.92-1.94 (m, 1H), 2.16-2.25 (m, 2H), 2.61-2.83 (m, 3H), 2.95-3.07 (m, 2H), 4.09 (dd, 1H), 4.33-4.34 (m, 1H), 4.42 (dd, 1H), 4.94 (s, 1H), 6.66-6.73 (m, 2H), 6.80 (d, 1H), 6.91-6.95 (m, 1H), 7.17 (t, 1H), 7.75-7.78 (m, 2H). As already mentioned hereinbefore, the compounds of formula I show interesting pharmacological properties, namely they exhibit an improved selectivity for the alpha2C adrenoceptor subtype and/or an enhanced potency. Said properties are demonstrated with the pharmacological test presented below.

Experiment 1

Determination of Alpha2A and Alpha2C Antagonistic Activity In Vitro

Chinese hamster ovary (CHO) cells stably transfected with human alpha2A and alpha2C or rodent alpha2D receptors (University of Turku, Finland) were cotransfected with the expression vector pCEP-Gα16 (Molecular Devices, CA, USA) and CHO cells stably transfected with human adrenergic alpha2B receptors and mitochondrially targeted aequorin (Euroscreen, Belgium) were used in this experiment. The cells were maintained at 37° C. in a 5% $CO_2$/95% air atmosphere. The cells were cultured in HAM F-12 medium supplemented with 10% FCS, 25 mM HEPES, 100 IU/ml penicillin, 100 g/ml streptomycin, 500 μg/ml geneticin and 240 g/ml hygromycin B. The cells were subcultured twice weekly with 0.25% trypsin and 1 mM EDTA. The subculture ratio was 1:5-1:20. The growth medium was changed every 2 or 3 days. All cell culture reagents were from Gibco. The day before the experiment the cells were plated into black-walled, clear bottom 96-well plates at a density of 30,000-45,000 cells/well.

The growth medium was removed and the cells were incubated with the test compounds and the FLIPR Calcium 3 Assay reagent (Molecular Devices, CA, USA) for 1 h at 37° C. in dark. The test compounds (concentrations in cells 100 μM-10 μM) were dissolved in Probenecid-Ringer consisting of 150 mM NaCl, 3 mM KCl, 1.2 mM $MgCl_2$, 1 mM $CaCl_2$, 5 mM glucose, 20 mM HEPES and 2.5 mM probenecid (pH 7.4 adjusted with 1.0 M NaOH). The osmolarity was adjusted to 322 milliosmoles with Osmostat® OM-6020 osmometer (DIC Kyoto Daiichi Kagagu Co. Ltd, Japan). The changes in intracellular calcium were monitored using FLEXstation benchtop scanning fluorometer with integrated fluid transfer workstation (Molecular Devices, CA, USA) and displayed using SOFTmax PRO version 3.2 software. All experiments were performed at 37° C. The test compounds dissolved in Probenecid-Ringer were applied by FLEX station at 17 s time point. The $IC_{50}$ value for a given test compound was determined from dose-response curves, which ranged from 0.01 nM to 10 μM. In order to determine antagonism, the cells were stimulated either with 100 nM adrenaline or 200 nM noradrenaline and the test compounds were added to the cells at least 5 min before the experiment. Typically, there were four replicates at each concentration and seven different dose levels. For example, if the number of plates from which results were obtained was three, 84 (4*7*3) wells were thus measured to construct dose-response relationship. The samples were excited at 485 nm and emission was detected at 525 nm with a 515 nm cut-off filter. Reading time was 60 s per well and the photomultiplier sensitivity value was set to 15. The minimum fluorescence value subtracted from the maximum value for each well was used in the calculations. SOFTmax PRO version 3.2 software was used for analyzing the results. Fitting of the antagonist dose-response results was performed with the free Hill equation and the $IC_{50}$ values were fitted with Michaelis-Menten equation in Sigma Plot 8.0.

The results are shown in Table 1.

TABLE 1

Alpha2A and alpha2C antagonistic activity in vitro.

| Compound | $IC_{50}$/nM | |
|---|---|---|
| | Alpha2A | Alpha2C |
| Compound of example 2 | 3780.6 | 11.4 |
| Compound of example 12 | 374.1 | 19.6 |
| Compound of example 18 | >10000 | 69.5 |
| Compound of example 29 | 4357.3 | 5.4 |
| Compound of example 48 | 1470.4 | 7.4 |
| Compound of example 58 | 776.2 | 9.5 |
| Compound of example 61 | 2874.0 | 2.4 |
| Compound of example 63 | 2726.4 | 0.8 |
| Compound of example 69 | 1286.2 | 1.7 |
| Compound of example 71 | 1154.0 | 1.1 |
| Compound of example 72 | 635.4 | 0.9 |
| Compound of example 74 | 345.7 | 7.4 |
| Compound of example 86 | 8423.6 | 10.7 |
| Compound of example 89 | 2141.0 | 0.6 |
| Compound of example 96 | 5444.6 | 4.6 |

In vivo effects of the compounds of formula I can be demonstrated with the pharmacological tests as described in WO 03/082866.

The compounds of formula I exhibit alpha2C antagonistic activity. The present invention thus provides compounds for use as a medicament. Compounds for use in the treatment of diseases or conditions where an alpha2C antagonist is indicated to be useful are also provided. Furthermore, a method for the treatment of diseases or conditions where an alpha2C antagonist is indicated to be useful is provided. In said method an effective amount of at least one compound of formula I is administered to a mammal, e.g. human, in need of such treatment. The use of the compounds of formula I for the manufacture of a medicament for the treatment of diseases or conditions where an alpha2C antagonist is indicated to be useful is also provided.

In one embodiment of the invention the aforementioned disease or condition where an alpha2C antagonist is indicated to be useful is a mental disorder propagated by stress, Parkinson's disease, depression, schizophrenia, attention deficit hyperactivity disorder, post-traumatic stress disorder, obsessive compulsive disorder, Tourette's syndrome, blepharospasm or other focal dystonias, temporal lobe epilepsy with psychosis, a drug-induced psychosis, Huntington's disease, a disorder caused by fluctuation of the levels of sex hormones, panic disorder, Alzheimer's disease or mild cognitive impairment; for example, a mental disorder propagated by stress, Parkinson's disease, depression, schizophrenia, attention deficit hyperactivity disorder, obsessive compulsive disorder or Alzheimer's disease; such as a mental disorder propagated by stress, depression or schizophrenia.

Representative examples of drug-induced psychoses include, but are not limited to, psychosis caused by chronic use of dopaminergic agents.

Representative examples of disorders caused by fluctuation of the levels of sex hormones include, but are not limited to, premenstrual syndrome and hot flashes.

The compounds of the invention can be administered, for example, enterally, topically or parenterally by means of any pharmaceutical formulation useful for said administration and comprising at least one active compound of formula I in pharmaceutically acceptable and effective amounts together with pharmaceutically acceptable diluents, carriers and/or excipients known in the art. The manufacture of such pharmaceutical formulations is known in the art.

The therapeutic dose to be given to a subject in need of the treatment will vary depending on the compound being administered, the species, the age and the sex of the subject being treated, the particular condition being treated, as well as the route and method of administration, and is easily determined by a person skilled in the art. Accordingly, the typical dosage for oral administration is from 10 ng/kg to 100 mg/kg per day and for parenteral administration from 1 ng/kg to 10 mg/kg for an adult mammal.

The compounds of the invention are given to the subject as such or in combination with one or more other active ingredients, each in its own composition or some or all of the active ingredients combined in a single composition, and/or suitable pharmaceutical excipients. Suitable pharmaceutical excipients include conventionally used excipients and formulation aids, such as fillers, binders, disintegrating agents, lubricants, solvents, gel forming agents, emulsifiers, stabilizers, colorants and/or preservatives.

The compounds of the invention are formulated into dosage forms using commonly known pharmaceutical manufacturing methods. The dosage forms can be, for example, tablets, capsules, granules, suppositories, emulsions, suspensions or solutions. Depending on the route of administration and the galenic form, the amount of the active ingredient in a formulation can typically vary between 0.01% and 100% by weight.

A person skilled in the art will appreciate that the embodiments described in this application can be modified without departing from the inventive concept. A person skilled in the art also understands that the invention is not limited to the particular embodiments disclosed but is intended to also cover modifications of the embodiments that are within the scope of the invention.

The invention claimed is:

1. A method for the treatment of a disease or a condition of the peripheric nervous system or the central nervous system, wherein the disease or condition is a mental disorder propagated by stress, Parkinson's disease, depression, schizophrenia, attention deficit hyperactivity disorder, post-traumatic stress disorder, obsessive compulsive disorder, Tourette's syndrome, blepharospasm or other focal dystonias, temporal lobe epilepsy with psychosis, a drug-induced psychosis, Huntington's disease, a disorder caused by fluctuation of the levels of sex hormones, panic disorder, Alzheimer's disease, and/or mild cognitive impairment comprising administering to a mammal in need of such treatment an effective amount of at least one compound of formula I,

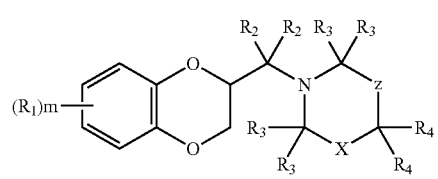

wherein
X is $C(R_5)(R_6)$ or $C(R_7)(R_8)$;
z is $-[C(R_4)_2]_n-$ or a single bond;

$R_1$ is, independently at each occurrence, hydroxy, $(C_1-C_6)$alkyl, $(C_1-C_6)$alkoxy, halogen, halo$(C_1-C_6)$alkyl, phenyl$(C_1-C_6)$alkoxy, $(C_1-C_6)$alkoxy-(C=O)—, CN, NO$_2$, NH$_2$, mono- or di$(C_1-C_6)$alkylamino or carboxy;

$R_2$ is, independently at each occurrence, H or $(C_1-C_6)$alkyl;

$R_3$ is, independently at each occurrence, H or $(C_1-C_6)$alkyl;

$R_4$ is, independently at each occurrence, H, hydroxy, $(C_1-C_6)$alkyl, $(C_2-C_6)$alkenyl, hydroxy$(C_1-C_6)$alkyl, hydroxy$(C_2-C_6)$alkenyl, $(C_1-C_6)$alkoxy$(C_1-C_6)$alkyl, $(C_2-C_6)$alkenyloxy$(C_1-C_6)$alkyl, $(C_1-C_6)$alkyl-(C=O)—, $(C_1-C_6)$alkoxy-(C=O)—, hydroxy$(C_1-C_6)$alkoxy$(C_1-C_6)$alkyl or $(C_1-C_6)$alkoxy$(C_1-C_6)$alkoxy$(C_1-C_6)$alkyl;

or $R_4$ and $R_4$ both attached to the same carbon ring atom form, together with the carbon ring atom to which they are attached, a —(C=O)— group;

$R_5$ is H or hydroxy;

or $R_4$ and $R_5$ attached to adjacent carbon ring atoms form a bond between the carbon ring atoms to which they are attached;

$R_6$ is phenyl unsubstituted or substitute with 1 or 2 substituent(s) $R_9$;

$R_7$ is H, $(C_1-C_6)$alkyl, hydroxy$(C_1-C_6)$alkyl, $(C_1-C_6)$alkoxy$(C_1-C_6)$alkyl or $(C_1-C_6)$alkoxy-(C=O)—;

or $R_4$ and $R_7$ attached to adjacent carbon ring atoms form a bond between the carbon ring atoms to which they are attached;

$R_8$ is hydroxy, $(C_1-C_6)$alkyl, $(C_2-C_6)$alkenyl, $(C_1-C_6)$alkoxy, halogen, hydroxy$(C_1-C_6)$alkyl, halo$(C_1-C_6)$alkyl, hydroxy$(C_2-C_6)$alkenyl, hydroxy$(C_1-C_6)$alkoxy, halo$(C_1-C_6)$alkoxy, phenyl$(C_1-C_6)$alkoxy, $(C_1-C_6)$alkoxy$(C_1-C_6)$alkyl, $(C_2-C_6)$alkenyloxy$(C_1-C_6)$alkyl, $(C_1-C_6)$alkyl-(C=O)—, $(C_1-C_6)$alkoxy-(C=O)—, $(C_1-C_6)$alkoxy-(C=O)—$(C_1-C_6)$alkyl, $(C_1-C_6)$alkyl-S—, $(C_1-C_6)$alkyl-(C=O)—O—, $(C_1-C_6)$alkyl-(C=O)—O—$(C_1-C_6)$alkyl, hydroxy-(C=O)—$(C_1-C_6)$alkoxy, hydroxy-(C=O)—$(C_1-C_6)$alkoxy$(C_1-C_6)$alkyl, $(C_1-C_6)$alkoxy-(C=O)—$(C_1-C_6)$alkoxy$(C_1-C_6)$alkyl, $(C_1-C_6)$alkyl-S—$(C_1-C_6)$alkyl, hydroxy$(C_1-C_6)$alkyl-S—$(C_1-C_6)$alkyl, $(C_1-C_6)$alkoxy$(C_1-C_6)$alkyl-S—$(C_1-C_6)$alkyl, $(C_1-C_6)$alkyl-(C=O)—S—$(C_1-C_6)$alkyl, $(C_1-C_6)$alkoxy-(C=O)—$(C_1-C_6)$alkyl-S—$(C_1-C_6)$alkyl, $(C_1-C_6)$alkyl-S—$(C_1-C_6)$alkoxy$(C_1-C_6)$alkyl, hydroxy$(C_1-C_6)$alkyl-S—$(C_1-C_6)$alkoxy, $(C_1-C_6)$alkoxy$(C_1-C_6)$alkyl-S—$(C_1-C_6)$alkoxy$(C_1-C_6)$alkyl, $(C_1-C_6)$alkyl-(O=S=O)—$(C_1-C_6)$alkyl, hydroxy$(C_1-C_6)$alkyl-(O=S=O)—$(C_1-C_6)$alkyl, $(C_1-C_6)$alkoxy$(C_1-C_6)$alkyl-(O=S=O)—$(C_1-C_6)$alkyl, $(C_1-C_6)$alkyl-(O=S=O)—$(C_1-C_6)$alkoxy$(C_1-C_6)$alkyl, hydroxy$(C_1-C_6)$alkyl-(O=S=O)—$(C_1-C_6)$alkoxy$(C_1-C_6)$alkyl, $(C_1-C_6)$alkoxy$(C_1-C_6)$alkyl-(O=S=O)—$(C_1-C_6)$alkoxy$(C_1-C_6)$alkyl, $(C_1-C_6)$alkyl-O—(O=S=O)—$(C_1-C_6)$alkyl, hydroxy$(C_1-C_6)$alkyl-O—(O=S=O)—$(C_1-C_6)$alkyl, $(C_1-C_6)$alkyl-(O=S=O)—O—$(C_1-C_6)$alkyl, hydroxy$(C_1-C_6)$alkyl-(O=S=O)—$(C_1-C_6)$alkyl, $(C_1-C_6)$alkyl-(O=S=O)—N(R$_{10}$)—$(C_1-C_6)$alkyl, hydroxy$(C_1-C_6)$alkoxy$(C_1-C_6)$alkyl, $(C_1-C_6)$alkoxy$(C_1-C_6)$alkoxy$(C_1-C_6)$alkyl, halo$(C_1-C_6)$alkoxy$(C_1-C_6)$alkyl, CN, NO$_2$, (R$_{10}$)$_2$N—, (R$_{10}$)$_2$N—$(C_1-C_6)$alkyl-S—$(C_1-C_6)$alkyl, (R$_{10}$)$_2$N—(C=O)—$(C_1-C_6)$alkyl-(O=S=O)—$(C_1-C_6)$alkyl, carboxy, R$_{11}$—(O=S=O)—, R$_{11}$—(O=S=O)—O— or $(C_1-C_6)$alkoxy-$(C_1-C_6)$alkoxy;

or $R_4$ and $R_8$ attached to adjacent carbon ring atoms form, together with the carbon ring atom to which they are attached, a condensed phenyl ring, wherein said phenyl ring is unsubstituted or substituted with 1 or 2 substituent(s) each independently is hydroxy, $(C_1-C_6)$alkyl, $(C_1-C_6)$alkoxy, hydroxy$(C_1-C_6)$alkyl, halo$(C_1-C_6)$alkyl, $(C_1-C_6)$alkoxy$(C_1-C_6)$alkyl, $(C_1-C_6)$alkyl-(C=O)— or $(C_1-C_6)$alkoxy-(C=O)—;

or $R_4$ and $R_8$ attached to adjacent carbon ring atoms form, together with the carbon ring atoms to which they are attached, a condensed 5 or 6 membered saturated or unsaturated carbocyclic ring or a condensed 5 or 6 membered saturated or unsaturated heterocyclic ring containing 1 or 2 heteroatom(s) chosen from N, O, and S, wherein said carbocyclic or heterocyclic ring is unsubstituted or substituted with 1 or 2 substituent(s) each independently is hydroxy, $(C_1-C_6)$alkyl, $(C_1-C_6)$alkoxy, hydroxy$(C_1-C_6)$alkyl, halo$(C_1-C_6)$alkyl, $(C_1-C_6)$alkoxy$(C_1-C_6)$alkyl, $(C_1-C_6)$alkyl-(C=O)—, $(C_1-C_6)$alkoxy-(C=O)— or oxo;

or $R_7$ and $R_8$ form, together with the carbon ring atom to which they are attached, a 5 or 6 membered saturated carbocyclic ring or a 5 or 6 membered saturated heterocyclic ring containing 1 or 2 heteroatom(s) chosen from N, O, and S, wherein said carbocyclic or heterocyclic ring, is unsubstituted or substituted with 1 or 2 substituent(s) each independently is hydroxy, $(C_1-C_6)$alkyl or oxo;

$R_9$ is, independently at each occurrence, hydroxy, $(C_1-C_6)$alkyl, $(C_2-C_6)$alkenyl, $(C_1-C_6)$alkoxy, halogen, hydroxy$(C_1-C_6)$alkyl, halo$(C_1-C_6)$alkyl, hydroxy$(C_1-C_6)$alkenyl, hydroxy$(C_1-C_6)$alkoxy, halo$(C_1-C_6)$alkoxy, phenyl$(C_1-C_6)$alkoxy, $(C_1-C_6)$alkoxy$(C_1-C_6)$alkyl, $(C_2-C_6)$alkenyloxy$(C_1-C_6)$alkyl, $(C_1-C_6)$alkyl-(C=O)—, $(C_1-C_6)$alkoxy-(C=O)—, $(C_1-C_6)$alkoxy-(C=O)—$(C_1-C_6)$alkyl, $(C_1-C_6)$alkyl-S—, $(C_1-C_6)$alkyl-(C=O)—O—, $(C_1-C_6)$alkyl-(C=O)—O—$(C_1-C_6)$alkyl, hydroxy-(C=O)—$(C_1-C_6)$alkoxy, hydroxy-(C=O)—$(C_1-C_6)$alkoxy$(C_1-C_6)$alkyl, $(C_1-C_6)$alkoxy-(C=O)—$(C_1-C_6)$alkoxy$(C_1-C_6)$alkyl, $(C_1-C_6)$alkyl-S—$(C_1-C_6)$alkyl, hydroxy$(C_1-C_6)$alkyl-S—$(C_1-C_6)$alkyl, $(C_1-C_6)$alkoxy$(C_1-C_6)$alkyl-S—$(C_1-C_6)$alkyl, $(C_1-C_6)$alkyl-(C=O)—S—$(C_1-C_6)$alkyl, $(C_1-C_6)$alkoxy-(C=O)—$(C_1-C_6)$alkyl-S—$(C_1-C_6)$alkyl, $(C_1-C_6)$alkyl-S—$(C_1-C_6)$alkoxy$(C_1-C_6)$alkyl, hydroxy$(C_1-C_6)$alkyl-S—$(C_1-C_6)$alkoxy$(C_1-C_6)$alkyl, $(C_1-C_6)$alkoxy$(C_1-C_6)$alkyl-S—$(C_1-C_6)$alkoxy$(C_1-C_6)$alkyl, $(C_1-C_6)$alkyl-(O=S=O)—$(C_1-C_6)$alkyl, hydroxy$(C_1-C_6)$alkyl-(O=S=O)—$(C_1-C_6)$alkyl, $(C_1-C_6)$alkoxy$(C_1-C_6)$alkyl-(O=S=O)—$(C_1-C_6)$alkyl, $(C_1-C_6)$alkyl-(O=S=O)—$(C_1-C_6)$alkoxy$(C_1-C_6)$alkyl, hydroxy$(C_1-C_6)$alkyl-(O=S=O)—$(C_1-C_6)$alkoxy$(C_1-C_6)$alkyl, $(C_1-C_6)$alkoxy$(C_1-C_6)$alkyl-(O=S=O)—$(C_1-C_6)$alkoxy$(C_1-C_6)$alkyl, $(C_1-C_6)$alkyl-O—(O=S=O)—$(C_1-C_6)$alkyl, hydroxy$(C_1-C_6)$alkyl-(O=S=O)—$(C_1-C_6)$alkyl, $(C_1-C_6)$alkyl-(O=S=O)—O—$(C_1-C_6)$alkyl, hydroxy$(C_1-C_6)$alkyl-(O=S=O)—O—$(C_1-C_6)$alkyl, $(C_1-C_6)$alkyl-(O=S=O)—N(R$_{10}$)—$(C_1-C_6)$alkyl, hydroxy$(C_1-C_6)$alkoxy$(C_1-C_6)$alkyl, $(C_1-C_6)$alkoxy$(C_1-C_6)$alkoxy$(C_1-C_6)$alkyl, halo$(C_1-C_6)$alkoxy$(C_1-C_6)$alkyl, CN, NO$_2$, (R$_{10}$)$_2$N—, (R$_{10}$)$_2$N—$(C_1-C_6)$alkyl, (R$_{10}$)$_2$N—(C=O)—, (R$_{10}$)$_2$N—(C=O)—$(C_1-C_6)$alkoxy$(C_1-C_6)$alkyl, (R$_{10}$)$_2$N—(C=O)—$(C_1-C_6)$alkyl-S—$(C_1-C_6)$alkyl, (R$_{10}$)$_2$N—(C=O)—$(C_1-C_6)$alkyl-(O=S=O)—$(C_1-C_6)$alkyl, carboxy, R$_{11}$—(O=S=O)— or R$_{11}$—(O=S=O)—O—;

or $R_9$ and $R_9$ attached to adjacent carbon ring atoms form, together with the carbon ring atoms to which they are attached, a condensed phenyl ring, a condensed 5 or 6 membered unsaturated carbocyclic ring or a condensed 5 or 6 membered unsaturated heterocyclic ring containing 1 or 2 heteroatom(s) chosen from O and S, wherein said phenyl, carbocyclic or heterocyclic ring is unsubstituted or substituted with 1 or 2 substituent(s) each independently is hydroxy, $(C_1-C_6)$alkyl, $(C_1-C_6)$alkoxy, hydroxy$(C_1-C_6)$alkyl, halo$(C_1-C_6)$alkyl, $(C_1-C_6)$alkoxy$(C_1-C_6)$alkyl, $(C_1-C_6)$alkyl-$(C=O)$— or $(C_1-C_6)$alkoxy-$(C=O)$—;

$R_{10}$ is independently at each occurrence, H, $(C_1-C_6)$alkyl, hydroxy$(C_1-C_6)$alkyl, $(C_1-C_6)$alkyl-$(C=O)$— or $R_{11}$—$(O=S=O)$—;

$R_{11}$ is, independently at each occurrence, hydroxy, $(C_1-C_6)$alkyl, $(C_1-C_6)$alkoxy, halo$(C_1-C_6)$alkyl or mono- or di$(C_1-C_6)$alkylamino;

m is 0, 1 or 2; and n is 1 or 2;

or a pharmaceutically acceptable salt or ester thereof;

with the provisos that the compound is not 1-(6-tert-butyl-2,3-dihydrobenzo[1,4]dioxin-2-ylmethyl)-3,5-dimethyl-piperidine, 1-(7-tert-butyl-2,3-dihydrobenzo[1,4]dioxin-2-ylmethyl-3,5-dimethyl-piperidine, 1-[1-(7-tert-butyl-2,3-dihydrobenzo[1,4]dioxin-2-yl)-ethyl]-3,5-dimethyl-piperidine, 1-(2,3-dihydrobenzo[1,4]dioxin-2-ylmethyl)-3,5-dimethyl-piperidine, 1-(7-tertbutyl-2,3-dihydrobenzo[1,4]dioxin-2-ylmethyl)-3,3-dimethyl-piperidine, 1-(6-tert-butyl-2,3-dihydrobenzo[1,4]dioxin-2-ylmethyl)-3,3-dimethyl-piperidine, 1-(7-tert-butyl-2,3-dihydrobenzo[1,4]dioxin-2-ylmethyl)-3-methyl-piperidine, 1-(6-tert-butyl-2,3-dihydrobenzo[1,4]dioxin-2-ylmethyl)-3-methyl-piperidine, 1-[1-(6-tert-butyl-2,3-dihydrobenzo[1,4]dioxin-2-yl-ethyl]-3,5-dimethyl-piperidine, 1-(2,3-dihydrobenzo[1,4]dioxin-2-ylmethyl)piperidine-3-carboxylic acid methyl ester, 1-(2,3-dihydrobenzo[1,4]dioxin-2-ylmethyl)-4-oxo-piperidine-3-carboxylic acid methyl ester, 1-(2,3-dihydrobenzo[1,4]dioxin-2-ylmethyl)-1,2,5,6-tetrahydro-pyridine-3-carboxylic acid methyl ester, 1-(2,3-dihydrobenzo[1,4]dioxin-2-ylmethyl)-4-hydroxy-1,2,5,6-tetrahydro-pyridine-3-carboxylic acid methyl ester, 2-(2,3-dihydrobenzo[1,4]dioxin-2-ylmethyl)-6,7-dimethoxy-1-methyl-1,2,3,4-tetrahydro-isoquinoline, 2-(2,3-dihydrobenzo[1,4]dioxin-2-ylmethyl)-6,7-dimethoxy-1,2,3,4-tetrahydro-isoquinoline, 2-(2,3-dihydrobenzo[1,4]dioxin-2-ylmethyl)-1,2,3,4-tetrahydro-isoquinoline or 1-(2,3-dihydro-benzo[1,4]dioxin-2-ylmethyl-3-(3-trifluoromethyl-phenyl)-pyrrolidine.

2. The method according to claim 1, wherein the disease or condition is depression, schizophrenia, and/or Alzheimer's disease.

* * * * *

UNITED STATES PATENT AND TRADEMARK OFFICE
CERTIFICATE OF CORRECTION

PATENT NO. : 8,697,723 B2
APPLICATION NO. : 13/917745
DATED : April 15, 2014
INVENTOR(S) : David Din Belle et al.

Page 1 of 1

It is certified that error appears in the above-identified patent and that said Letters Patent is hereby corrected as shown below:

In the Claims:

Col. 71, line 21, "$R_5$ is phenyl unsubstituted or substitute" should read --$R_6$ is phenyl unsubstituted or substituted--.

Col. 71, line 65, "with the carbon ring atom" should read --with the carbon ring atoms--.

Col. 72, lines 27-28, "hydroxy ($C_1$-$C_6$) alkenyl," should read --hydroxy ($C_2$-$C_6$) alkenyl,--.

Col. 73, line 25, "tertbutyl" should read --tert-butyl--.

Signed and Sealed this
Fifth Day of August, 2014

Michelle K. Lee
*Deputy Director of the United States Patent and Trademark Office*